(12) United States Patent
Hsieh et al.

(10) Patent No.: US 7,919,579 B2
(45) Date of Patent: Apr. 5, 2011

(54) IMAGING AND THERAPEUTIC TARGETING OF PROSTATE AND BLADDER TISSUES

(75) Inventors: Jer-Tsong Hsieh, Plano, TX (US); Jian Zhou, Plano, TX (US); Xiankai Sun, Coppell, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 110 days.

(21) Appl. No.: 11/923,388

(22) Filed: Oct. 24, 2007

(65) Prior Publication Data

US 2009/0123381 A1    May 14, 2009

Related U.S. Application Data

(60) Provisional application No. 60/863,281, filed on Oct. 27, 2006.

(51) Int. Cl.
C07K 7/04 (2006.01)
C07K 7/08 (2006.01)
(52) U.S. Cl. ...................................... 530/327
(58) Field of Classification Search ........................ None
See application file for complete search history.

(56) References Cited

U.S. PATENT DOCUMENTS 6,610,657 B1    8/2003    Goueli ........................... 514/14

FOREIGN PATENT DOCUMENTS

WO    WO 0183554 A2 *  11/2001

OTHER PUBLICATIONS

Borley et al., "Laparoscopic pelvic lymph node dissection allows significantly more accurate staging in "high-risk" prostate cancer compared to MRI or CT," *Scand. J. Urol. Nephrol.*, 37:382-386, 2003.
Boswell et al., "Comparative in vivo stability of copper-64-labeled cross-bridged and conventional tetraazamacrocyclic complexes," *J. Med. Chem.*, 47:1465-1474, 2004.
Carter et al., "Nonpalpable prostate cancer: detection with MR imaging," *Radiology*, 178:523-525, 1991.
Derossi et al., "Trojan peptides: the penetratin system for intracellular delivery," *Trends in Cell Biol.*, 8:84-87, 1998.
Deshayes et al., "Cell-penetrating peptides: tools for intracellular delivery of therapeutics," *Cell Mol. Life Sci.*, 62:1839-1849, 2005.
Drin et al., "Peptide delivery to the brain via adsorptive-mediated endocytosis: advances with SynB vectors," *AAPS Pharm. Sci.*, 4:26, 2002.
El-Andaloussi et al., "Cell-penetrating peptides: mechanisms and applications," *Curr. Pharm. Des.*, 11:3597-3611, 2005.
Ferrari, "Cancer nanotechnology: opportunities and challenges," *Nat. Rev. Cancer*, 5:161-171, 2005.
Fischer et al., "A stepwise dissection of the intracellular fate of cationic cell-penetrating peptides," *J. Biol. Chem.*, 279:12625-12635, 2004.
Futaki et al., "Arginine-rich peptides. An abundant source of membrane-permeable peptides having potential as carriers for intracellular protein delivery," *J. Biol. Chem.*, 276:5836-5840, 2001.
Futaki et al., "RNase S complex bearing arginine-rich peptide and anti-HIV activity," *J. Mol. Recognit.*, 18:169-174, 2005.
Gioeli et al., "Activation of mitogen-activated protein kinase associated with prostate cancer progression," *Cancer Res.*, 59:279-284, 1999.
Gupta and Gupta, "Synthesis and surface engineering of iron oxide nanoparticles for biomedical applications," *Biomaterials*, 26:3995-4021, 2005.
Hersh et al., "Newer imaging modalities to assess tumor in the prostate," *Cancer Control*, 11:353-357, 2004.
Jager et al., "Prostate cancer staging: should MR imaging be used?—A decision analytic approach," *Radiology*, 215:445-451, 2000.
Jana and Blaufox, "Nuclear medicine studies of the prostate, testes, and bladder," *Semin. Nucl. Med.*, 36:51-72, 2006.
Mayer, "SH3 domains: complexity in moderation," *J. Cell Sci.*, 114:1253-1263, 2001.
Noguchi et al., "A new cell-permeable peptide allows successful allogeneic islet transplantation in mice," *Nat. Med.*, 10:305-309, 2004.
Pooga et al., "Cell penetration by transportan," *FASEB J.*, 12:67-77, 1998.
Price et al., "Activation of extracellular signal-regulated kinase in human prostate cancer," *J. Urol.*, 162:1537-1542, 1999.
Quinn et al., "MR imaging of prostate cancer with an endorectal surface coil technique: correlation with whole-mount specimens," *Radiology*, 190:323-327, 1994.
Saar et al., "Cell-penetrating peptides: a comparative membrane toxicity study," *Anal. Biochem.*, 345:55-65, 2005.
Schöder and Larson, "Positron emission tomography for prostate, bladder, and renal cancer," *Semin. Nucl. Med.*, 34:274-292, 2004.
Schwarze et al., "In vivo protein transduction: delivery of a biologically active protein into the mouse," *Science*, 285:1569-1572, 1999.
Sumers, "Staging prostate cancer with MR imaging," *Radiology*, 187:875, 1993.
Sun et al., "In vivo behavior of copper-64-labeled methanephosphonate tetraaza macrocyclic ligands," *J. Biol. Inorg. Chem.*, 8:217-225, 2003.
Sun et al., "In vivo evaluation of copper-64-labeled monooxotetraazamacrocyclic ligands," *Nucl. Med. Biol.*, 31:1051-1059, 2004.
Sun et al., "Radiolabeling and in vivo behavior of copper-64-labeled cross-bridged cyclam ligands," *J. Med. Chem.*, 45:469-477, 2002.
Torchilin, "Fluorescence microscopy to follow the targeting of liposomes and micelles to cells and their intracellular fate," *Adv. Drug Deliv. Rev.*, 57:95-109, 2005.

(Continued)

Primary Examiner — Andrew D Kosar
(74) Attorney, Agent, or Firm — Fulbright & Jaworski

(57) ABSTRACT

The present invention provides methods for imaging and the treatment of cancer. In certain embodiments, a polyarginine (e.g., R11) may be used to selectively image prostate or bladder cells (e.g., a metastatic prostate cancer). In other embodiments, a DOC-2/DAB2 peptide, optionally conjugated to a cell permeable peptide (e.g., R11) may be used to treat a cancer, such as prostate cancer.

3 Claims, 27 Drawing Sheets

OTHER PUBLICATIONS

Turner et al., "Cell-penetrating peptide conjugates of peptide nucleic acids (PNA) as inhibitors of HIV-1 Tat-dependent trans-activation in cells," *Nucleic Acids Res.*, 33:6837-6849, 2005.

Vidal et al., "SH2 and SH3 domains as targets for anti-proliferative agents," *Crit. Rev. Oncol. Hematol.*, 40:175-186, 2001.

Vivès et al., "A truncated HIV-1 Tat protein basic domain rapidly translocates through the plasma membrane and accumulates in the cell nucleus," *J. Biol. Chem.*, 272:16010-16017, 1997.

Wadia and Dowdy, "Transmembrane delivery of protein and peptide drugs by TAT-mediated transduction in the treatment of cancer," *Adv. Drug Deliv. Rev.*, 57:579-596, 2005.

Wender et al., "The design, synthesis, and evaluation of molecules that enable or enhance cellular uptake: peptoid molecular transporters," *Proc. Natl. Acad. Sci. USA*, 97:13003-13008, 2000.

Xie et al., "Protein transduction domain of membrane penetrating peptide can efficiently deliver DNA and protein into mouse liver for gene therapy," *Hepatobiliary Pancreat. Dis. Int.*, 4:90-93, 2005.

Zhou and Hsieh, "The inhibitory role of DOC-2/DAB2 in growth factor receptor-mediated signal cascade. DOC-2/DAB2-mediated inhibition of ERK phosphorylation via binding to Grb2," *J. Biol. Chem.*, 276:27793-27798, 2001.

Zhou et al., "Characterization of a novel negative regulator (DOC-2/DAB2) of c-Src in normal prostatic epithelium and cancer," *J. Biol. Chem.*, 278:6936-6941, 2003.

Zhou et al., "Inhibition of mitogen-elicited signal transduction and growth in prostate cancer with a small peptide derived from the functional domain of DOC-2/DAB2 delivered by a unique vehicle," *Cancer Res.*, 66:8954-8958, 2006.

Zhou et al., "Signal transduction targets in androgen-independent prostate cancer," *Cancer & Met. Rev.*, 20:351-362, 2001.

Zhou et al., "Synergistic induction of DOC-2/DAB2 gene expression in transitional cell carcinoma in the presence of GATA6 and histone deacetylase inhibitor," *Cancer Res.*, 65:6089-6096, 2005.

Ziegler et al., "The cationic cell-penetrating peptide CPP(TAT) derived from the HIV-1 protein TAT is rapidly transported into living fibroblasts: optical, biophysical, and metabolic evidence," *Biochemistry*, 44:138-148, 2005.

\* cited by examiner

IMAGING AND THERAPEUTIC TARGETING OF PROSTATE AND BLADDER TISSUES

This application claims benefit of priority to U.S. Provisional Application Ser. No. 60/863,281, filed Oct. 27, 2006.

This invention was made with government support under Grant No. DAMD17-03-2-0033 awarded by the United States Army. The government has certain rights in the invention.

BACKGROUND OF THE INVENTION

1. Field of the Invention

The present invention relates generally to the fields of molecular biology and medicine. More particularly, it concerns imaging and the diagnosis and treatment of cancer.

2. Description of Related Art

In the United States, prostate cancer (PCa) has been the most commonly diagnosed cancer in males and is consistently among the leading causes of cancer-related deaths of men. According to the "2006 Cancer Facts and Figures" published by the American Cancer Society, an estimated 234,460 new cases of prostate cancer will be diagnosed and 27,350 men will die of prostate cancer in the United States alone in 2006. Most of the deaths from prostate cancer are related to advanced disease, in which patients present with bone metastasis and soft-tissue involvement. The risk of extraprostatic disease in patients with clinically localized disease typically remains high (30-60%), despite definite local therapy. The skeleton is the most common site for metastases in a variety of cancers, among which breast and prostate cancers account for over 80% of cases causing the great morbidity due to intractable bone pain, pathological fractures, hypercalcemia and nerve compression (Cole et al., 2000; Coleman, 2001). Once the tumor spreads to bone, it can become unresponsive to standard therapeutic treatments, and there is presently no effective treatment of bone metastases.

Whole-body bone scan using $^{99m}$Tc-MDP (methylene diphosphonate) is currently the standard procedure for the detection of bone metastases after bone symptoms appear, although problems are associated with this approach. In clinical practice, the bone involvement may not be observed in the bone scan until 5 years after micrometastasis has occurred; therefore, a bone scan with negative results does not prove the absence of metastasis. Due to the limited specificity, $^{99m}$Tc-MDP bone scan is often aided by other imaging modalities, such as X-ray radiography, MRI, CT, PET scans, and/or bone marrow biopsy for a final diagnosis. Thus, there exists a strong need to develop new agents that allow for the early diagnosis of the extraprostatic spread of PCa.

SUMMARY OF THE INVENTION

The present invention overcomes deficiencies in the art by providing compositions and methods for the imaging, diagnosis, and treatment of a cancer (e.g., prostate cancer). The inventors surprisingly found that certain cell permeable proteins (e.g., R11) facilitate selective uptake by bladder and prostate tissues. Thus, the present invention allows for the selective targeting of prostate cells (e.g., for imaging or the treatment of a hyperproliferative disease such as cancer). Additionally, the present invention also provides approaches for treating cancer via the use of certain bioactive peptides (e.g., PPL, a DOC-2/DAB2 peptide), optionally conjugated to a cell permeable peptide (CPP).

In one aspect, the present invention provides a pharmaceutical composition comprising R11 conjugated to a DOC/DAB2 peptide. The DOC/DAB2 peptide may comprise or consist essentially of PPL (SEQ ID NO:6).

In another aspect, the present invention provides a method of imaging a prostate or bladder cell comprising contacting the prostate cell with an imaging agent conjugated to a polyarginine or an arginine-rich peptide. The polyarginine or arginine-rich peptide may be 7-30 residues and in certain embodiments is R11. The prostate or bladder cell may be a cancerous cell (e.g., a metastatic or non-metastatic cancerous cell, recurrent cancerous cell, multi-drug resistant cancer cell).

In various embodiments, the prostate or bladder cell is located in a subject, and wherein the imaging agent conjugated to the polyarginine or arginine-rich peptide is administered to the subject. The administration may be intravenous, intraspinal, intracranial or intraperitoneal. The subject may be a human. The method may comprise contacting the prostate or bladder cell with the imaging agent conjugated to a polyarginine or arginine-rich peptide in vitro. The imaging agent may comprise a SPECT or PET imaging agent. The PET imaging agent may comprise $^{64}$Cu or $^{18}$F. The PET imaging agent may further comprise a chelator (e.g., DOTA). In some embodiments, the imaging agent comprises a visually detectable label or a radioisotope. For example, the visually detectable label may be a fluorescent imaging agent.

In yet another aspect, the present invention provides a method of inhibiting the growth of a prostate or bladder cancer cell comprising contacting the prostate cancer cell with an anti-cancer compound conjugated to a polyarginine or an arginine-rich peptide. The polyarginine may be 7-30 residues. In various embodiments, the polyarginine is R11. The anti-cancer compound may comprise a DOC/DAB2 peptide. The DOC/DAB2 peptide may comprise PPL (SEQ ID NO:6). In some embodiments, the DOC/DAB2 peptide consists essentially of PPL (SEQ ID NO:6). R11 may be conjugated to the PPL (R11-PPL). The prostate or bladder cancer cell may be a metastatic or non-metastatic cancerous cell, recurrent cancerous cell, or multi-drug resistant cancer cell.

In certain embodiments, the prostate or bladder cancer cell is comprised in a subject and the anti-cancer compound is administered to the subject. The administration may be intravenous, intraperitoneal, intranasal, intradermal, intraarterial, intralesional, intracranial, intraarticular, intraprostatic, intrapleural, intratracheal, intranasal, intravitreal, intravaginal, intrarectal, topically, intramuscularly, subcutaneous, subconjunctival, intravesicular, mucosal, intrapericardial, intraumbilical, intraoculoral, oral, topical, local, inhalation, aerosol inhalation, injection, infusion, continuous infusion, localized perfusion bathing target cells directly, via a catheter, via a lavage, in a lipid composition, in a liposome, intratumoral, into the tumor vasculature or resected tumor bed. The prostate or bladder cancer may be metastatic cancer or a non-metastatic cancer. The anticancer compound may be a radiopharmaceutical or a chemotherapeutic. The conjugation may comprise covalent bonding.

"Conjugated," as used herein, refers to the association of two moieties, preferably via a covalent bond. The moieties (e.g., peptide, polypeptide, small molecule, etc.) may or may not be directly associated with each other, and some additional region of a molecule may reside between the moieties. For example, as described below, a R11 group may be conjugated with any bifunctional chelator. In one embodiment R11 is conjugated to a bifunctional chelator to form a $^{64}$Cu-labeled R11.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, the uptake of CPPs by PCa cells. Different concentrations of each CPP were incubated with cells for 30 minutes prior to cell harvesting. Relative FITC intensity was determined by normalizing fluorescence intensity of each treatment with its cell numbers. FIG. 1B, time course of R11 uptake by PCa cells. R11 (5 μM) was incubated with cells at the indicated time. Relative FITC intensity was determined by normalizing fluorescence intensity of each treatment with its cell numbers. FIG. 1C, in vitro half-life of R11 in PCa cells. Cells were pulsed with R11 (5 μM) chased for the indicated time and the percentage of uptake was used time zero (=100%). Each column or data point represents mean±SD in triplicate. All the experiments were repeated at least twice.

FIG. 2A, different concentrations of each R11, R11AAL and R11PPL were incubated with cells for 30 minutes prior to cell harvesting. Relative FITC intensity was determined by normalizing fluorescence intensity of each treatment with its cell numbers. Each column or data point represents mean±SD in triplicate. All the experiments were repeated at least twice. FIG. 2B, cells were incubated with 5 μM of indicated peptide for 30 minutes. After fixation, cells were counterstained with DAPI. The cellular distribution of each peptide was visualized with fluorescence microscope.

(FIG. 9A) In vitro uptake by bladder cancer cell lines 30 min after incubation. Relative uptake was determined by fluorometer and normalized using R11 5 μM (=1) in each cell line. (FIG. 9B) Animal study (n=3; 24 h post injection). The peptides (5 nmole/gram body weight) were administered via intravenous (IV) route. SV: seminal vesicle; CG: coagulation gland. (FIG. 9C) The tissue localization of FITC-R11 in mouse bladder.

FIG. 10B: Toxin B) 2 h and then incubated with 5 µM CPPs for 30 min before harvesting cell for determining cellular uptake. For competition assay, various concentrations of GAG's and 5 µM R9, R11, or R13 were added into cells for 30 min before harvesting cell for determining cellular uptake (FIG. 10C). Relative uptake was determined based on control (=1).

DESCRIPTION OF ILLUSTRATIVE EMBODIMENTS

Figure 1A:
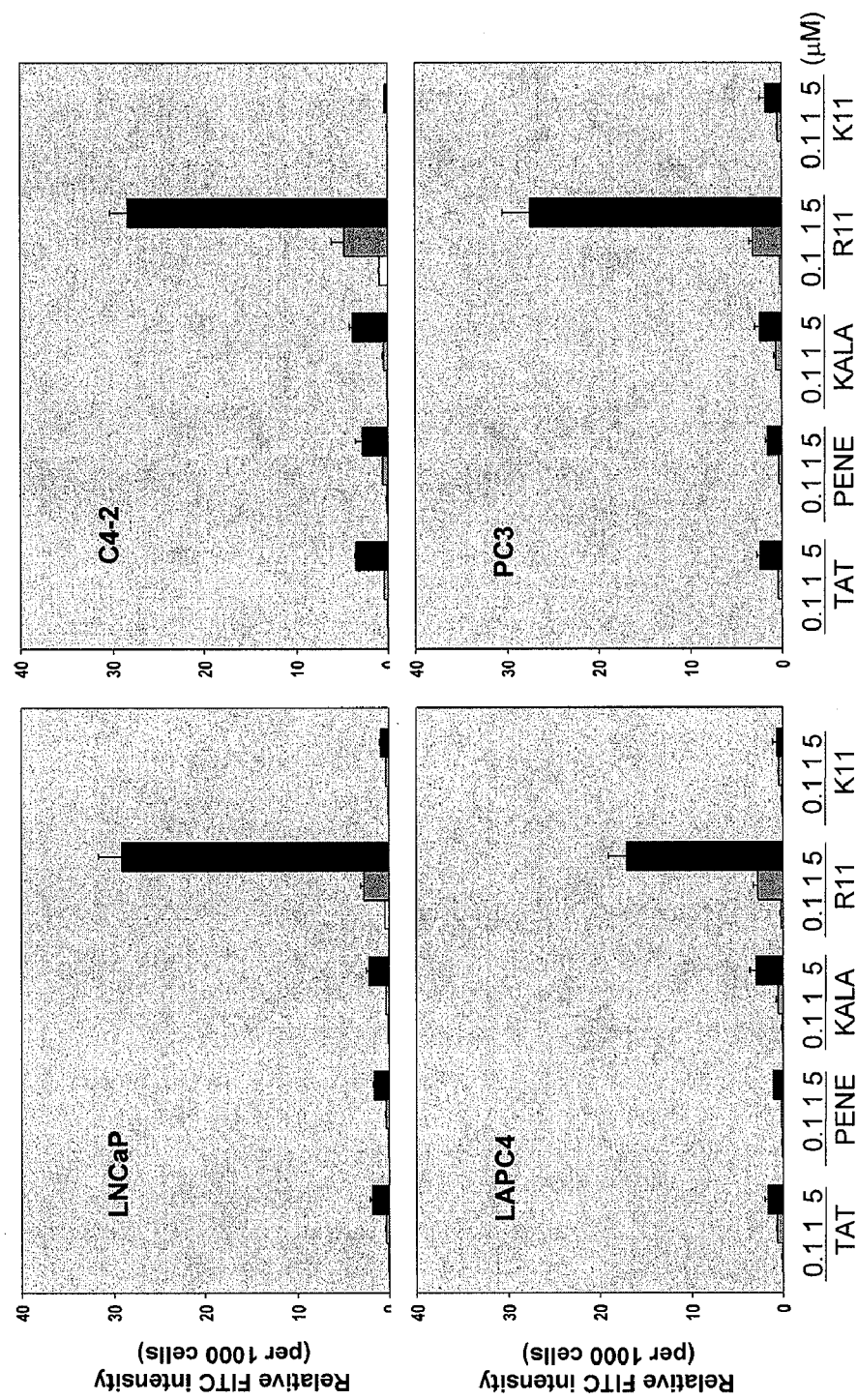
FIGS. 1A-C—Characterization of R11 in PCa cells. The fluorescence-labeled CPPs (TAT, Penetratin (PENE), KALA, R11 & K11) were synthesized and tested in a variety of PCa cells (LNCaP, C4-2, LAPC4 and PC3 cells).

The present invention provides compositions and methods for imaging and the diagnosis and treatment of cancer. The inventors have made the surprising discovery that certain cell permeable proteins (e.g., R11) result in selective uptake by bladder and prostate tissues. Additionally, the present invention also provides approaches for treating cancer via the use of certain bioactive peptides (e.g., PPL, a DOC-2/DAB2 peptide) optionally conjugated to a cell-permeable peptide.

I. Cell-Permeable Peptides

Cell-permeable peptides (CPP) have drawn considerable interest in the field of intracellular drug delivery (Ziegler et al., 2005; Xie et al., 2005; Wadia and Dowdy, 2005; Turner et al., 2005; Torchilin, 2005; Saar et al., 2005; Futaki et al., 2005; El-Andaloussi et al., 2005; Deshayes et al., 2005). To the inventors surprise, an arginine-rich peptide (R11) showed highly preferential accumulations in prostate and bladder. As shown below, this peptide clearly exhibits preferential uptake in prostate and bladder, thus indicating applications for both imaging techniques and therapeutic approaches.

A CPP, as used herein, refers to an arginine-rich peptide, a polyarginine or a polylysine sequence that induces uptake or can be used to enhance cellular uptake of the peptide into cells. The cell-permeable peptide may comprise 7-30, 7-26, 8-20, 9-15, 10-12, or 11 positively-charged amino acid residues, preferably arginine residues. In certain embodiments, the CCP (e.g., a polyarginine) may be, for example, 7, 8, 9, 10, 11, 12, 13, 14, 15, 16, 17, 18, 19, 20, 21, 22, 23, 24, or 25 amino acids long.

The cell permeable peptide is preferably positively-charged under physiological conditions, although in some instances it may be possible to use an negatively-charged amino acid to achieve a similar effect. In certain embodiments, the cell-permeable peptide $pK_a$ of about 12.3, 12.4, 12.5, 12.6, 12.7 or 12.8.

Several CPP's have been identified. HIV TAT protein, a transcription factor required for reproduction of the HIV virus, has been shown to enter cells spontaneously (Green and Loewenstein, 1988); the sequence derived from TAT (amino acid 49-57; RKKRRQRRR; SEQ ID NO:1) has protein transduction ability and is highly basic. Several proteins have also been reported to have a similar property including Antennapedia and Galparan (transportan) (Derossi et al., 1998; Pooga et al., 1998). In addition, other homopolymers of cationic amino acids such as lysine and arginine have also been found to have such function (Wender et al., 2000). Typically, a short amino acid sequence cell permeable peptide (CPP) can enter cells rapidly in vitro and in vivo (Wadia and Dowdy, 2005). CPP can be used for delivering different cargos such as proteins/peptides, DNA/RNA, liposomes and nanoparticles (Wadia and Dowdy, 2005). Also, recent studies using a preclinical animal model (Noguchi et al., 2004; Schwarze et al., 1999) indicate that CPP delivery did not cause undesirable side effects, suggesting that CPP have applications in cancer therapies. Examples of CPP's include transferin, lactoferrin, TGF-β, nerve growth factor, albumin, HIV tat peptide, RGD peptide, and insulin, as well as others (Gupta et al., 2005; Ferrari, 2005). Cell-penetrating peptides are also described in, e.g., U.S. Pat. No. 6,610,657 and Drin, et al., 2002.

The inventors have identified an efficient CPP delivery system in prostate cancer (PCa) cells. Furthermore, the inventors designed a unique small peptide by conjugating a CPP with a functional PR domain from DOC-2/DAB2 and tested for its activity as a growth suppressor. Data presented in the below Examples provide support for using bioactive peptides delivered via a CPP as a therapeutic agent for cancers and prostate cancer in particular.

A. Polyarginine and Arginine-Rich Peptides

An arginine-rich sequence refers to a peptide that contains at least about 80%, at least about 85%, at least about 90%, at least about 95%, and up to 100% arginine residues. Where 100% arginine (i.e., polyarginine), the polyarginine typically contains 7-30, 7-25, 7-20, 7-16, 8-14, 9-13, 10-12 or 11 arginine residues. Where less than 100%, the arginine residues are preferably contiguous, although it is recognized that another amino acid (e.g., a lysine or other amino acid) may be included (terminally or internally) in the peptide and still achieve the same effect.

In certain embodiments the polyarginine may be represented by the formula $(Arg)_x$, wherein x=7, 8, 9, 10, 11, 12, 13, 14, 15, 16, 17, 18, 19, 20, 21, 22, 23, 24, 25, 26, 27, 28, 29 30, or ranges of 7-30, 8-26, 8-20, 9-15, and 10-12. "R11" refers to the polyarginine wherein x=11. In certain embodiments, the CPP (e.g., a polyarginine) may be 7, 8, 9, 10, 11, 12, 13, 14, 15, 16, 17, 18, 19, 20, 21, 22, 23, 24, 25, 26, 27, 28, 29, or amino acids long.

L- and/or D-isomers of arginine may be included in a polyarginine. In certain embodiments, only L-arginine may be used for the peptide synthesis. However, in certain embodiments, D-homopolymers have the advantage of additional in vivo stability for various (e.g., cancer therapy, imaging) applications. Thus, D-arginine may be used to prepare D-polyarginines or mixed D- and L-polyarginines may also be used.

B. Other Methods for Facilitating Cellular Uptake

Although a CPP (e.g., a polyarginine, R11) may be used in certain embodiments of the present invention, other moieties may be used in addition to or in place of a CPP to enhance cellular uptake (e.g., in a prostate tissue). Examples of moieties for enhancing cellular uptake include but are not limited to: a hydrophobic group (e.g., a lipid or fatty acid) and certain metal chelates. In certain embodiments, the moiety is conjugated to an anti-cancer compound, such as a bioactive peptide or chemotherapeutic, for delivery to a certain tissue type, such as prostate tissue.

Generally, a fatty acid is a molecule comprising a carbon chain with an acidic moiety (e.g., carboxylic acid) at an end of the chain. In certain embodiments, the length of the carbon chain is from 4 to 18 carbon atoms in the chain portion of the fatty acid. In specific embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated. The fatty acid may be branched, though in certain embodiments of the present invention, it is unbranched. Specific fatty acids include, but are not limited to, linoleic acid, oleic acid, palmitic acid, linolenic acid, stearic acid, lauric acid, myristic acid, arachidic acid, palmitoleic acid, arachidonic acid.

radiotherapeutic isotope in the prostate and/or bladder tissue can result in a therapeutic destruction of the cells (e.g., a killing of a metastatic prostate cancer). It is anticipated that a composition of the present invention comprising a radiotherapeutic may be administered to a subject (e.g., a human patient) by means including parenteral administration (e.g., intraperitoneal injection, intravenous administration, etc.).

It is anticipated that the present invention may be used with regard to virtually any imaging technique. These imaging techniques include positron emission tomography (PET), single photon emission tomography (SPECT), and magnetic resonance imaging (MRI). For example, a CPP may be conjugated to an imaging or contrast agent to allow for imaging of a prostate cell or tissue. Table 1 lists various radiotracers that may be used with certain imaging techniques. In various embodiments, radioisotopes (e.g. $^{18}$F, $^{64/62}$Cu, $^{111}$In, $^{177}$Lu, $^{186/188}$Re, and $^{123}$I, etc.) may be utilized in various imaging agents present invention.

TABLE 1

| Radiotracers | Isotope source | Molecular targets | Disease | Indications |
|---|---|---|---|---|
| | | Water-soluble | | |
| $^{18}$F-FDG | Cyclotron (PET) | Glucose metabolism Tumor localization | Neurology, Cardiology Oncology | Lung cancer Myocardial viability Alzheimer's disease |
| $^{18}$F Fluorodopa (18F-DOPA) | Cyclotron (PET) | Metabolism, neurotransmission and cell processes | Neurology | Parkinson's disease |
| $^{18}$F-MISO | Cyclotron (PET) | Hypoxia | Oncology, Cardiology | Tumor hypoxia, Myocardial infarction, Stroke |
| $^{64}$Cu-ATSM $^{62}$Cu-ATSM | Cyclotron (PET) Generator (PET) | Hypoxia | Oncology, Cardiology | Tumor hypoxia, Myocardial infarction, Stroke |
| $^{188}$Re-guanine | Generator (SPECT) | Tumor therapeutic | Oncology | Cancer therapy |
| | | Oil-soluble | | |
| $^{18}$F-Fluorotamoxifen | Cyclotron (PET) | Estrogen receptor | Oncology, Cardiology | Breast cancer |
| $^{123}$I-Iodotamoxifen | Unit-dose (SPECT) | Estrogen receptor | Oncology | Breast cancer |
| $^{123}$I-Iodomisonidazole | Unit-dose (SPECT) | Hypoxia | Oncology, Cardiology | Tumor hypoxia, Myocardial infarction, Stroke |

II. Imaging and Radiotherapies

One aspect of the present invention relates to methods for the imaging of a prostate or bladder tissue (e.g., a prostate cancer) using a CPP. In particular, the inventors have discovered that certain polyarginines (e.g., the R11 CPP) can selectively facilitate uptake by prostate cells including prostate cancer (PCa) cells. This approach may be used to selectively identify or test for the presence or absence of PCa cells (e.g., metastatic PCa tumors) in a subject, such as a human. In certain embodiments, the present invention may be used to perform imaging on a subject who does not have cancer; for example, a subject may be imaged as a diagnostic tool to determine if the subject has a cancer or other disorder.

The present invention also provides methods for the selective delivery of a radiotherapeutic isotope to a prostate or bladder tissue (e.g., a prostate cancer) using a CPP. For example, a radiotherapeutic isotope (e.g., $^{131}$I, $^{177}$Lu, $^{188}$Re, $^{90}$Y, etc.) may be conjugated to a CPP and administered to a subject (e.g., a human patient). The accumulation of the The approaches of the present invention have particular advantages for imaging of PCa, as compared to traditional approaches which have been utilized with limited success. Besides $^{99m}$Tc-MDP bone scan (planar gamma scintigraphy), X-ray and computed tomography (CT) has traditionally been used to evaluate the extent of distal cancer proliferation, more recently magnetic resonance imaging (MRI) has also joined the clinical practices for more accurate staging of PCa (Hersh et al., 2004; Borley et al., 2003) as MRI techniques rapidly evolve (Carter et al., 1991; Jager et al., 2000; Quinn et al., 1994; Sumers, 1993).

Functional/metabolic imaging modalities, such as PET and SPECT, have the advantage of improved specificity and sensitivity as compared with other imaging modalities. Thus PET has drawn considerable attention in the diagnostic imaging of PCa and its distal spread (Bender et al., 1997; Dimitrakopoulos-Strauss and Strauss, 2003; Hain and Maisey, 2003; Hofer et al., 2001; Hoh et al., 1998; Hricak et al., 2003; Karam et al., 2003; Kumar et al., 2004; Kwee et al., 2005;

Maecke et al., 2005; Mathews and Oz, 2002; Oyama et al., 2004; Oyen et al., 2004; Shvarts et al., 2002; Sun et al., 2005; Toth et al., 2005; Varagnolo et al., 2000). However, the most popular PET tracer, $^{18}$F-FDG (2-$^{18}$F-fluoro-2-deoxy-D-glucose), is not quite as successful at identifying PCa as it is in the detection of other tumors and metastases (Hersh et al., 2004; Kumar et al., 2004; Alavi et al., 2004a; Alavi et al., 2004b; Sanz et al., 2004; Scheffel and Pomper, 2004). In breast, lung, and other carcinomas with predominantly osteolytic metastasis, FDG-PET has shown higher specificity and sensitivity than $^{99m}$Tc-MDP bone scan in the detection of distant tumor spread due to the glucose avidity of lytic metastases; whereas in PCa with predominantly osteoblastic lesions where the viable tumors are relatively small and dormant, FDG-PET performance has not been optimal (Fogelman et al., 2005; Langsteger et al., 2006). As a result, other PET tracers have been introduced based on different molecular mechanisms, such as $^{18}$F-labeled FLT (3'-deoxy-3'-$^{18}$F-fluorothymidine) (Oyama et al., 2004), FDHT (16β-$^{18}$F-fluoro-5α-dihydrotestosterone), FMAU (1-(2'-deoxy-2'-$^{18}$F-β-D-arabinofuranosyl)thymine) (Sun et al., 2005), choline (Kwee et al., 2005), and acetate (Matthies et al., 2004); $^{11}$C-labeled choline (Zheng et al., 2004), acetate (Dimitrakopoulos-Strauss and Strauss, 2003; Mathews and Oz, 2002; Fricke et al., 2003; Hautzel et al., 2002; Kotzerke et al., 2003; Oyama et al., 2002; Oyama et al., 2003), and methionine (Toth et al., 2005); $^{64}$Cu-labeled bombesin analogs (Chen et al., 2004; Rogers et al., 2003); and $^{68}$Ga-labeled somatostatin analogs (Maecke et al. 2005; Meyer et al., 2004; Riccabona and Decristoforo, 2003). However, to the knowledge of the inventors, successful methods employing PET in the diagnosis of localized or advanced PCa has not been previously established.

The present invention also provides advantages for imaging as compared with the previous use of antibodies for imaging. Prostate specific membrane antigen (PSMA) has also been exploited to develop targeted imaging agents for PCa (Ghosh and Heston, 2004; Huang et al., 2004; Lamb and Faulds, 1998). Indeed, the only FDA approved PCa imaging agent is an $^{111}$In-labeled PSMA monoclonal antibody (7E11-C5.3) (Ghosh and Heston, 2004; Huang et al., 2004; Lamb and Faulds, 1998), which is a SPECT tracer. Previously, clinical trials showed that this agent has improved sensitivity over CT or MRI, and could be used for staging localized PCa and metastases in conjunction with CT or MRI (Lamb and Faulds, 1998). However, more recent reports expose problems of specificity and sensitivity because the antibody (7E11-C5.3) only recognizes an internal epitope of PSMA (Ghosh and Heston, 2004). As a result, several research groups have developed antibodies (e.g., J591, J533, J415, and E99, etc.) that recognize epitopes within the extracellular PSMA domain (Smith-Jones, 2003; Chang, 2004; Liu et al., 1997; Murphy et al., 1998). Although these antibodies have shown improved sensitivity and specificity in preclinical or clinical studies, as Lange put it in an editorial (Lange, 2001), the development of such diagnostic/therapeutic agents "has been a cycle of initial enthusiasm and good results, followed by less sanguine data with loss of enthusiasm or silence."

One may optionally conjugate a fluorescent tag to a polyarginine or other composition of the present invention. For example, a peptide (e.g., an anti-cancer compound conjugated to a polyarginine) may be tagged with FITC for evaluation in vitro (e.g., effective internalization to LNCaP and PC-3 cell lines and long intracellular retention) and/or in vivo (e.g., prostate tissue specificity).

A. PET

Two positron-emission radioisotopes, $^{64}$Cu ($t_{1/2}$=12.7 h; β$^+$: 0.653 MeV, 17.4%) and $^{18}$F ($t_{1/2}$: 109.7 min; β$^+_{max}$: 0.635 MeV, 97%), may be used as labels for prostate tissue-specific peptides. $^{64}$Cu has certain advantages. First, it possesses a relatively long half-life. Second, $^{64}$Cu represents an excellent PET radionuclide for imaging purposes due to its decay characteristics, especially the low β$^+$-energies (Sun and Anderson, 2004; Snyder and Kilbourn, 2003) that render their PET images superior resolutions. $^{18}$F and $^{64}$Cu are available from suppliers including PETnet (Texas, U.S.A.) and MDS Nordion (Canada), respectively.

Peptides may be radiolabeled with $^{18}$F or $^{64}$Cu for in vitro and in vivo PET imaging evaluations. The peptides may be prepared using standard F-moc chemistry on an automated peptide synthesizer. Pharmacokinetic parameters of $^{64}$Cu-labeled R11, the lead peptide, were evaluated by the inventors in preliminary experiments by using a two-compartment model. The elimination half-life of $^{64}$Cu-DOTA-R11 from the blood (primary compartment) was about 10.7 min (ln 2/α). This approach allowed the inventors to clearly see a small subcutaneous tumor (4.7-mg) with the PET tracer at 1 h post injection. However, due to the unknown mechanism of the peptide specificity, it is reasonable to assume that a longer circulation time in the blood is preferable to enhance the image contrast. It is well known that peptides typically have short half lives in the blood circulation, which limit their uptake in targets, due to the degradation in plasma by endogenous peptidases and proteases and the rapid clearance from the blood (Benedetti et al., 2004).

Several approaches may be used to increase the half-life and improve the pharmacokinetics of a CPP of the present invention. While most peptides can be molecularly engineered to minimize the enzymatic degradation (e.g. using D- or mixed L/D amino acids), blood clearance is typically predominated by molecular size and hydrophilicity. Several approaches have been developed to effectively improve the PK and preserve the functions of peptides, e.g. PEGylation, glycosylation, and multimerization, etc. Multimerization of peptides can improve cell-specific binding affinity by more than two orders of magnitude (Haubner and Wester, 2004) and cellular internalization events can be initiated by surface receptor oligomerization (King and Feener, 1998).

To prolong the peptide half-life in blood, the multiple equivalent side-arms at nitrogen atoms of the macroring of DOTA may be used to build a simplified but versatile multifunctional scaffold for multimeric peptide presentation (Scheme 3). This scaffold features a bifunctional chelator, multiple PEG chains and functional groups for the attachment of CPP peptides. The PEG chains can be incorporated to increase the conformational flexibility and water solubility of the peptides and as spacers to minimize the interference of the chelating moiety on the peptides and the possible steric hindrance.

1. Radiochemistry Procedures of Labeling Peptides with $^{18}$F

Although there are considerable interests in developing peptide radiopharmaceuticals as molecular imaging probes, a limited number of $^{18}$F-labeled peptides have been reported for in vivo imaging (Snyder and Kilbourn, 2003; Poethko et al., 2004). Currently the common method for labeling peptides with $^{18}$F is through conjugation of peptides with a small $^{18}$F-labeled prosthetic group, which, in most cases, is an aryl $^{18}$F-fluoride. The reaction is usually either acylation (Snyder and Kilbourn, 2003; Downer et al., 1997; Herman et al., 1994; Jagoda et al., 2002; Kilbourn et al., 1987; Lang and Eckelman, 1994; Lang and Eckelman, 1997; Vaidyanathan et al., 2003; Vaidyanathan and Zalutsky, 1992; Vaidyanathan and Zalutsky, 1994; Vaidyanathan and Zalutsky, 1995; Wester et al., 1996) or oxime formation (Poethko et al., 2004; Bure et al., 2000; Hamma and Miller, 2003; Renaudet and Dumy, 2003; Schottelius et al., 2004; Thumshirn et al., 2003; Wester et al., 2004; Zatsepin et al., 2002). To preserve the specific binding affinity of peptides, protected peptide precursors are usually required in $^{18}$F-acylation, which mandates the subsequent deprotection and thus prolongs the radiolabeling time. Due to the oxime formation specificity of the aminooxy group that is attached to the N-terimus of the peptides, an unprotected peptide can be used in the radiolabeling route via oxime formation so that the radiolabeling time could be minimized.

$^{18}$F-labeling of peptides may be performed via synthesis routes as shown in Schemes 1 (acylation) and 2 (oxime formation). In the acylation route (Scheme 1), the peptide may be modified with the addition of a lysine to the C-terminus, while in the other approach, an aminoxy group is attached to the N-terminus (Scheme 2). Both modifications can be routinely performed using a solid phase peptide synthesizer (Poethko et al., 2004; Schottelius et al., 2004; Bloomberg et al., 1993; Sewald and Jakubke, 2002). Radiolabeling conditions may be optimized with respect to the pH of reaction media, temperature, reaction time, and peptide concentration, while the specific binding of peptides to prostate tissue is maintained. For a specific peptide, its $^{18}$F-labeling method may be chosen judiciously from experiments.

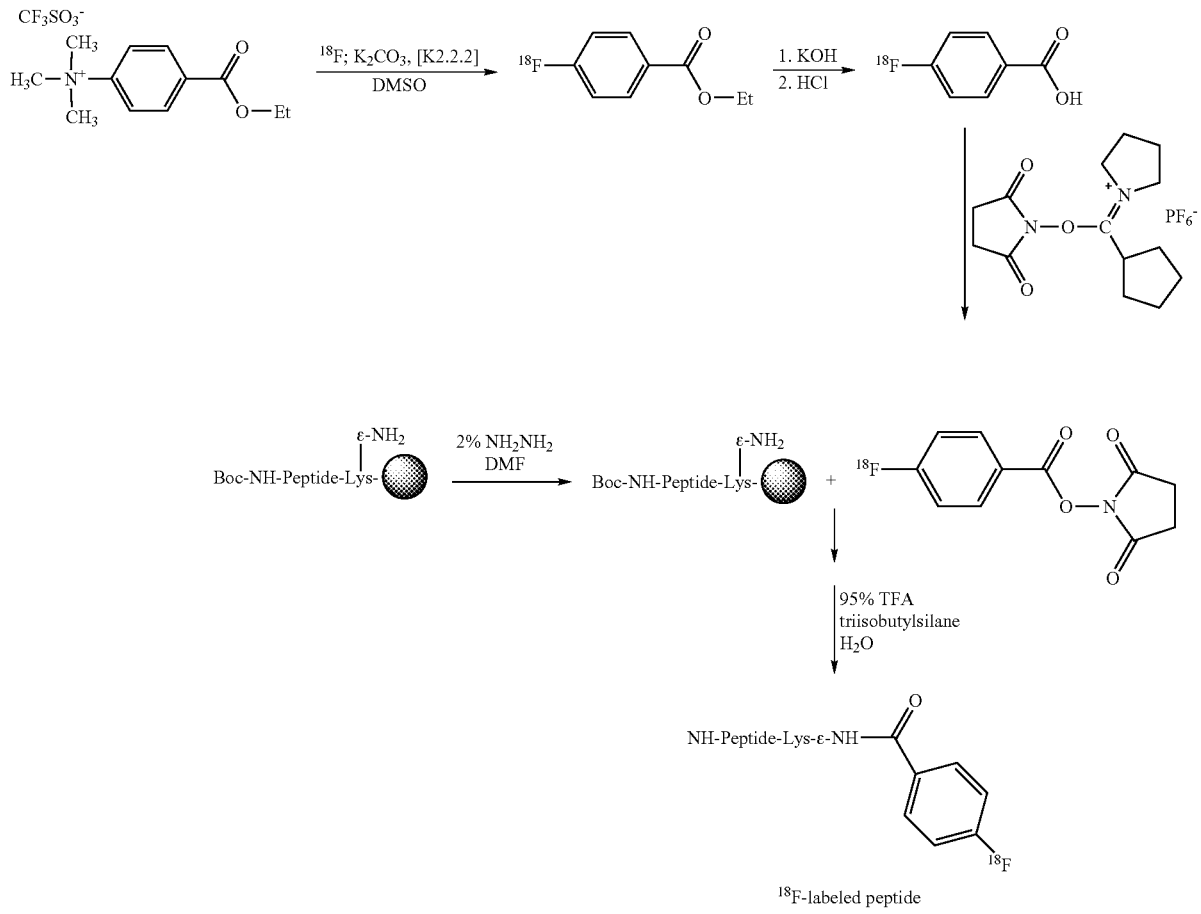

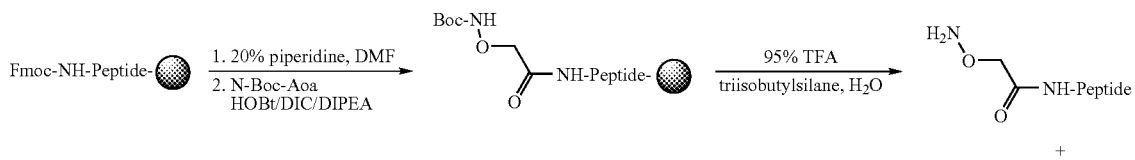

-continued

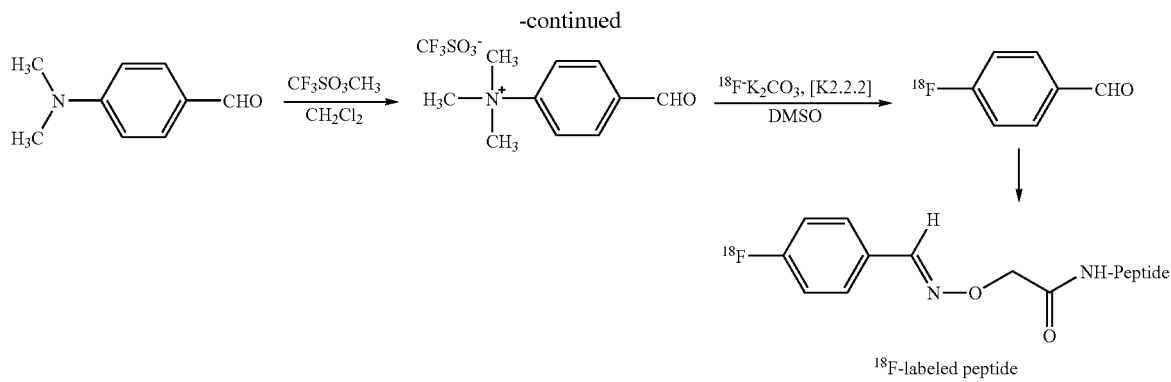

 Resin

N-Boc-Aoa: N-Boc-aminooxyacetic acid
HOBt: 1-Hydroxybenzotriazole
DIC: N,N'-diisopropylcarbodiimide
DIPEA: N-ethyldiisopropylamine
K2.2.2: Kryptofix 2.2.2

The corresponding "cold" products may be synthesized using the similar approaches outlined in Schemes 1 and 2. After the full characterization (NMR, MS, CHN, etc.), they may be used as standards to obtain optimal HPLC conditions for the quality control of $^{18}$F-labeling.

$^{18}$F-labeled peptides often exhibit high hepatic and intestinal uptake (Poethko et al., 2004; Schottelius et al., 2004; Wester et al., 2004; Vaidyanathan and Zalutsky, 1997; Wester et al., 1997). If this is the case for the $^{18}$F-labeled peptides, it could impose a drawback for the imaging of metastatic PCa. However, glycosylation of peptides may be used to effectively overcome this problem by decreasing the lipophilicity and thus optimizing the pharmacokinetics of the peptides (Poethko et al., 2004; Schottelius et al., 2004; Wester et al., 2004; Albert et al., 1993; Haubner et al., 2004). Glycosylation may be used to optimize in vivo distribution of the peptides.

2. Radiochemistry Procedures of Labeling Peptides with $^{64}$Cu

If the rapid in vivo kinetics of the peptides is not a concern for the imaging application, a bifunctional chelator (e.g., DOTA) may be conjugated with the peptides for $^{64}$Cu labeling, e.g., as shown in the below Examples. Otherwise, the peptides may be conjugated with either DOTA-(PEG-COOH)$_4$ or DOTA-(PEG-NH$_2$)$_4$ depending on the peptide chemistry to prepare tetrameric peptides for the following evaluations. The chemistry involved in the synthetic routes (Scheme 3) to DOTA-(PEG-COOH)$_4$ or DOTA-(PEG-NH$_2$)$_4$ are well established (Chavez et al., 2004; Engelhardt et al., 2002; Sun et al., 2006).

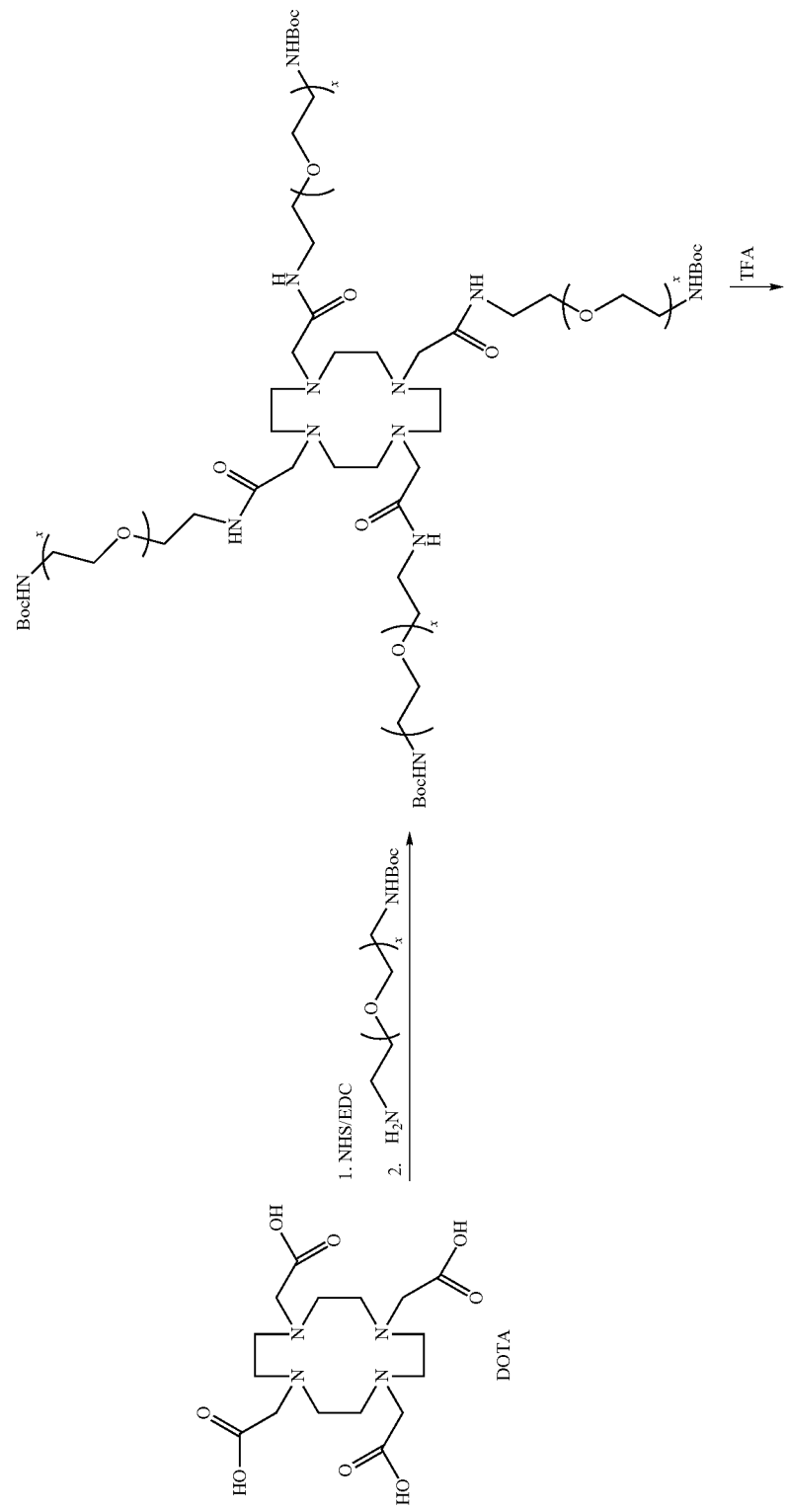
Scheme 3. The synthetic route to DOTA-(PEG-COOH)$_4$ or DOTA-(PEG-NH$_2$)$_4$.

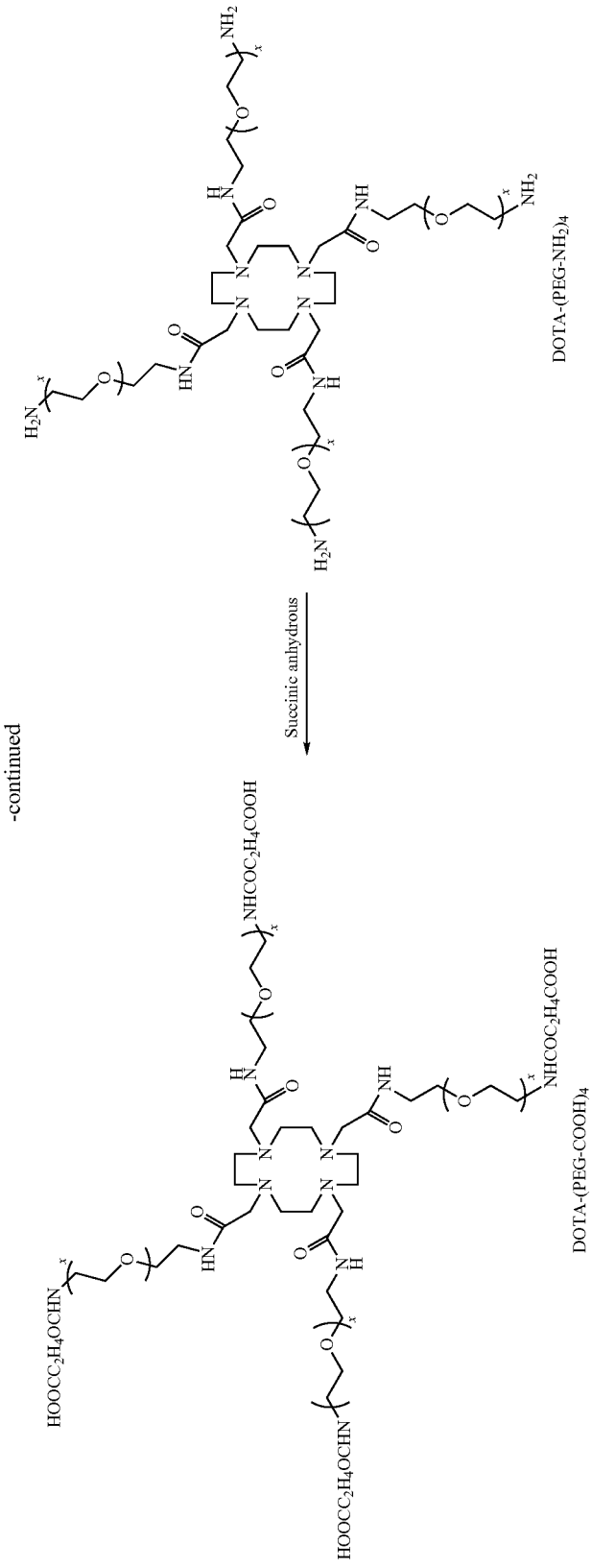

The PEG chain length (x) can be varied so that the scaffolds with different PK parameters could be provided. In certain embodiments x=10. In other embodiments x may be 1-100 or more, 1-75, 1-50, 1-25, 1-10 or any number derivable therein. Radiolabeling of the DOTA-peptide conjugates with $^{64}$Cu is straightforward, and separation and purification may be carried out by either C-18 cartridge or HPLC.

3. In Vitro Evaluation of the Radiolabeled Peptides

Evaluation of the stability of the radiolabeled peptides or peptide conjugates in vitro may be performed by incubation at 37° C. in fresh mammalian serum over 4 hr ($^{18}$F-labeled) or 24 hr ($^{64}$Cu-labeled). The volume of the complex added may not exceed 5% of the total volume. Degradation of the radiolabeled compounds may be assessed at given time points by the removal of an aliquot of sample for radio-TLC analysis ($C_{18}$ or silica gel solid phase), radio-HPLC (size-exclusion chromatography) and/or ethanol precipitation. On radio-HPLC, radioactivity that is not associated with the peptides can be used as a measure of the degradation of radiolabeled agents.

4. In Vivo Evaluation of the Radiolabeled Peptides

The tissue distribution of the radiolabeled peptides or peptide conjugates may be evaluated in normal nude mice. Radiolabeled compounds may be diluted with saline and be injected into mice via the tail vein. The animal number at each time point may be chosen for statistical analysis based on previous work (Boswell et al., 2004; Sun et al., 2004; Sun et al., 2003; Sun et al., 2002). Time points can be selected according to the physical half-life of the respective radioisotope (e.g., $^{18}$F-labeled compounds: 10-min, 20-min, 1-h, and 4-h; $^{64}$Cu-labeled compounds: 30-min, 1-h, 4-h, and 24-h). The injected volume of activity per animal may not exceed 150 µL. At selected time points post-injection, animals may be sacrificed, and organs of interest removed, weighed, and counted. The percent injected dose per gram (% ID/g) and percent injected dose per organ (% ID/organ) can be calculated by comparison to a weighed, counted, standard. Pharmacokinetic parameters can be estimated by a two-compartment model using the same animals. Specifically, blood (10-20-µL) can be drawn from the retroorbital sinus of the animals at 5-min, 10-min, 20-min, and 40-min, and counted on a gamma counter.

Biodistribution experiments may be performed. Urine excretion experiments may be carried out with the animal groups at the last time points in the above biodistribution studies. Mouse urine may be collected from metabolic cages at selected time points post-injection and counted in a gamma counter. In addition, the urine may be concentrated under nitrogen so that radio-TLC analysis can be performed to determine the percentage of intact complexes. The metabolic fate of $^{64}$Cu-labeled compounds may be evaluated by experiments in normal nude mice using previously described methods (Boswell et al., 2004; Sun et al., 2003). Non-target tissues (liver or blood) and decomposition may be evaluated at 1 h and 4 h post injection by determining the amount of radioactivity dissociated from the peptides or peptide conjugates using radio-HPLC.

5. PET Imaging Evaluation of the Radiolabeled Peptides in PCa Tumor-Bearing Mice Early detection of metastatic PCa tumor growth may be evaluated. Tumor cell lines (osteolytic PC-3-Luc and osteoblastic C4-2-Luc) may be used to establish tumor-bearing animal models (subcutaneous and intra-femur) to simulate the extraprostatic spread of PCa. A small animal PET system with a spatial resolution of <1 mm and reasonably high sensitivity (<200 µCi of injection dose ($^{18}$F) is needed) may be used, which is especially useful for investigating the intra-femur bone metastasis model in mice. Mice bearing tumors at three different stages (e.g. 2, 4, and 6 weeks after tumor-cell injection) may be used to evaluate each compound in each animal model. Prior to the PET imaging studies, the animals may be imaged by BLI to assess the tumor growth. Images may be analyzed quantitatively to evaluate the potential application of the radiolabeled compounds for the early detection of extraprostatic PCa. After imaging the final time point, the animals may be sacrificed to perform post-PET biodistribution studies. To evaluate PET imaging probes, FDG may be used as a standard in this project.

PCa detection specificity as compared to other carcinomas can be determined via the following method. The subcutaneous tumor model may be used to evaluate the PCa specificity of imaging probes. The left flank of animals may be implanted with LNCaP or PC-3 tumor cells, while the right flank with other cancer cell lines. The cancer cells may be lung cancer cell lines (H1299 and A549), kidney cancer cell lines (SW839 and A-498), bladder cancer cell lines (T24 and 253J), and liver cancer cell lines (HepG2). Starting from 1 week post tumor implantation, the PET imaging studies may be performed weekly with i.v. injection of imaging probes. The images may be analyzed quantitatively to evaluate the specificity of the imaging probes in the detection of PCa as compared to other tumors. The inventors anticipate that extraprostatic PCa spread will be differentiated from other cancer metastases by the imaging probes of the present invention.

B. SPECT

Single photon emission computed tomography (SPECT) is a nuclear medicine tomographic imaging technique using gamma rays (Daldrup-Link et al., 2006; Denoyer et al., 2006). SPECT can be used to obtain 3-D distribution information of a radionuclide, and this technique can be helpful for treating and diagnosing cancer. Radionuclides that may be used with SPECT include Technetium-99m ($^{99m}$Tc), Iodine-123 ($^{123}$I), and Indium-111 ($^{111}$In).

In certain embodiments a CPP may be conjugated with a bifunctional chelator to prepare a SPECT imaging or radiotherapeutic agent (with a radioisotope, such as $^{90}$Y, $^{131}$I, $^{188}$Re, and $^{177}$Lu etc.). In certain embodiments, SPECT may be used to selectively image a prostate tissue (e.g., a prostate cancer).

C. Magnetic Resonance Imaging

Certain aspects of the present invention also relate to magnetic resonance imaging (MRI). In certain embodiments, a CPP of the present invention may be conjugated to a MRI contrast agent (e.g., Gadolinium or iron oxide nanoparticle) in order to selectively image a prostate tissue (e.g., a prostate cancer). MRI uses the property of nuclear spin to collect image data. Nuclei with unpaired nucleons (protons or neutrons) possess a property known as spin, which results in a non-zero magnetic moment that can be used to conduct MRI (see, e.g., U.S. Pat. No. 5,397,987). Hydrogen nuclei have a single proton, and many MRI techniques utilize hydrogen nuclei since they are pervasive in human tissue. When a subject is placed in a main magnetic field, its nuclei align in the direction of the field (i.e., along the "magnetization axis"); the orientation of the nuclei can be represented by a magnetization vector (see, e.g., Horowitz, 1995). In the classical physical description of magnetic resonance, these spinning nuclei can precess in a conical manner around the magnetization axis, generally out-of-phase with respect to each other.

To induce in-phase spinning at the resonance frequency of particular nuclei, a high-powered radio frequency excitation pulse, frequently in the kilowatt range, is broadcast at that resonance frequency. This RF pulse also causes the nuclei in a sample (e.g., a human brain) to rotate with respect to the magnetization vector created by the main magnetic field (see, e.g., Horowitz, 1995). The spinning nuclei in the sample generate RF signals, which decay over time. Time-varying gradient magnetic fields are applied after the RF excitation pulse to permit spatial resolution of the decaying RF signals. Thus, the RF excitation pulse and the time-varying gradient magnetic fields together cause the sample to emit time-varying MR RF signals known as "free induction decay" (FID) signals. An antenna in the magnetic resonance (MR) scanner receives these FID signals, and these MR imaging signals are transmitted to a processor. The processor uses these signals to generate MR images that reflect the spatial distribution or chemical environment of the spinning nuclei. Contrast agents are used to increase the difference in signal between an area of interest to the background.

III. DOC-2/DAB2 Peptides to Inhibit Cell Growth

The present invention provides bioactive peptides useful for the treatment of hyperproliferative diseases such as cancer; in particular, the inventors have identified specific DOC-2/DAB2 peptides which may be used to treat specific cancers, such as prostate cancer (PCa). The inventors have demonstrated that loss of DOC-2/DAB2 expression is associated with PCa cells derived from later stage of cancer patients and DOC-2/DAB2 is a potent growth inhibitor for PCa cells by suppressing exogenous mitogens-elicited signal pathways (Zhou et al., 2001; Zhou and Hsieh, 2001; Zhou et al., 2003; Zhou et al., 2005). The structure-functional analysis of DOC-2/DAB2 protein unveils that the proline-rich (PR) domain in the C-terminus of DOC-2/DAB2 is the key functional motif, and the interaction between PR domain and src homologue 3 (SH3) domain from several adaptor or effector molecules, such as c-Src, Grb2 is the underlying mechanism. Such interaction can lead to the suppression of activated downstream MAP kinase critical for the growth of PCa (Gioeli et al., 1999; Price et al., 1999). Thus, restoring DOC-2/DAB2 protein function in PCa cells should have a therapeutic benefit.

DOC-2/DAB2 protein, often lost in PCa and other cancer types, has been shown to be a part of homeostatic machinery in normal prostate epithelium. In general, DOC-2/DAB2 modulates mitogens-elicited signal transduction by sequestering several adaptor or effector molecules such as such as Grb2 and c-Src, which results in the suppression of downstream MAP kinase activity. The results show that the proline-rich (PR) sequence in DOC-2/DAB2 is the key functional domain for this action.

As shown there, the inventors further explored the biologic function of these PR peptides in PCa using CPP as a delivery system. From screening of several CPPs, a polyarginine peptide (R11) displayed selective uptake, in vitro half-life and cellular location using four different PCa cell lines. By conjugating a PR sequence (PPL) or control sequence (AAL) derived from DOC-2/DAB2 to the C-terminus of R11, these studies demonstrated that R11PPL but not R11 or R11AAL was able to suppress either serum or androgen-induced cell proliferation in PCa cells with the loss of DOC-2/DAB2 expression. Consistently, the activation status of MAP kinase elicited by these mitogens was significantly inhibited by R11PPL but not by R11AAL or R11. Taken together, these studies demonstrate that a functional peptide derived from PR domain in DOC-2/DAB2 has growth inhibitory activity as its native protein and CPP appears to be an efficient delivery system in PCa cells; these approaches allow for a new therapeutic strategy for PCa.

IV. Bioactive Peptides

Certain aspects of the present invention involve the use of a peptide or polypeptide (e.g., a DOC/DAB2 peptide). As used herein, the term "polypeptide" means either a protein or a peptide. A "peptide" is considered to have from 3 to 100 amino acids. A protein is considered to have more than 100 amino acids.

In certain embodiments the size of the peptide molecule (e.g., a DOC/DAB2 peptide) may comprise, but is not limited to, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, and any range derivable therein. The bioactive peptide may be conjugated to another peptide (e.g., a targeting peptide such as a polyarginine or R11), an imaging agent (e.g., $^{64}$Cu-labeled DOTA, a PET imaging agent, a MRI imaging agent) and/or a radiotherapeutic.

As used herein, an "amino molecule" refers to any amino acid, amino acid derivative or amino acid mimic as would be known to one of ordinary skill in the art. In certain embodiments, the residues of the polypeptide are sequential, without any non-amino molecule interrupting the sequence of amino molecule residues. In other embodiments, the sequence may comprise one or more non-amino molecule moieties. In particular embodiments, the sequence of residues of the polypeptide may be interrupted by one or more non-amino molecule moieties.

In certain embodiments, a nanoparticle-polypeptide complex is provided comprising a biocompatible polypeptide. As used herein, the term "biocompatible" refers to a substance which produces little or no significant untoward effects when applied to, or administered to, a given organism according to the methods and amounts described herein. Such untoward or undesirable effects are those such as significant toxicity or adverse immunological reactions. In preferred embodiments, biocompatible polypeptides or nanoparticle-polypeptide complexes will generally be mammalian proteins or peptides or synthetic proteins or peptides each essentially free from toxins, pathogens and harmful immunogens.

Peptides may be made by any technique known to those of skill in the art, including the expression of proteins and peptides through standard molecular biological techniques, the isolation of proteins and peptides from natural sources, or the chemical synthesis of proteins and peptides. The nucleotide and polypeptide sequences for various genes have been previously disclosed, and may be found at computerized databases known to those of ordinary skill in the art. One such database is the National Center for Biotechnology Information's Genbank and GenPept databases, found on the World Wide Web at ncbi.nlm.nih.gov. The coding regions for these known genes may be amplified and/or expressed using the techniques disclosed herein or as would be known to those of ordinary skill in the art. Alternatively, various commercial preparations of proteins and peptides are known to those of skill in the art.

In certain embodiments a polypeptide may be isolated or purified. Generally, "isolated" or "purified" will refer to a specific polypeptide composition that has been subjected to fractionation to remove various other polypeptides, and which composition substantially retains its activity, as may be assessed, for example, by the protein assays, as would be known to one of ordinary skill in the art for the specific or desired protein or peptide.

In certain embodiments, a therapeutically effective amount of a polypeptide or nanoparticle-polypeptide complex is used to treat a tumor in a subject. A therapeutically effective amount is an amount that will result in an improvement or a desired change in condition for which an active ingredient is administered, when the ingredient is administered once or over a period of time. As is known, the amount will vary depending on such particulars as the type of condition being treated, the specific active ingredient, the severity of the condition, and the characteristics of the patient.

A. Variants

The terms "polypeptide," "protein" and "peptide" also encompass amino acid sequence variants of a protein or peptide. Amino acid sequence variants of the polypeptides of the present invention can be substitutional, insertional or deletion variants. Deletion variants lack one or more residues of the native protein that are not essential for function or immunogenic activity, as exemplified by variants of integral membrane proteins that lack a transmembrane sequence. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the polypeptide, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of a bioactive polypeptide are within the scope of the invention provided the biological activity of the polypeptide is maintained.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence and nevertheless produce a protein with like properties. It is thus contemplated by the inventors that various changes may be made in the amino acid sequences of the polypeptides described herein without appreciable loss of their biological utility or activity, as discussed below. Table 2 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent polypeptide. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See e.g., Johnson et al., 1993. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of the polypeptides described herein, but with altered and even improved characteristics.

In another embodiment, peptides contain D-amino acids rather than the L-amino acids typically found in biological proteins. The D-amino acids can be substituted during chemical synthesis of the peptides. Further, reverse-D peptides are contemplated. Reverse-D peptides retain the same tertiary conformation, and therefore the same activity, as the L-amino acid peptides, but are more stable to enzymatic degradation in vitro and in vivo, and thus have greater therapeutic efficacy than the original peptide Brady and Dodson, 1994; Jameson et al., 1994).

Proteins and peptides can be conjugated with fluorescent, chemiluminescent or other types of tags or labels for detection, as is well known in the art.

B. Fusion Proteins

A specialized kind of insertional variant is a fusion protein. This molecule generally has all or a substantial portion of the native molecule, linked at the N- or C-terminus, to all or a portion of a second polypeptide. For example, fusions can employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions. Particularly preferred fusions involve linking a cell-penetrating peptide to a polypeptide to promote uptake of the polypeptide by the cell.

For example, a polyarginine or other CPP (e.g., R11, a peptide from the HIV Tat polypeptide, the third helix of the *Drosophila* Antennapedia homeobox gene "Antp," the Influenza virus hemagglutinin and/or the herpes virus VP22 polypeptide) may be used with the present invention to create fusion proteins. These proteins contain positively charged domains enriched for arginine and lysine residues, and hydrophobic peptides derived from signal sequences and fusion sequences have been identified as cell-penetrating peptides. These peptides may be used to deliver proteins to a wide spectrum of cell types both in vitro and in vivo. In the present invention, these peptides can be used to promote the cellular uptake of bioactive proteins and peptides.

C. Polypeptide Purification

It may be desirable to purify or isolate a the polypeptides considered herein. Protein purification techniques are well known to those of skill in the art. These techniques involve, at one level, the crude fractionation of the cellular milieu to polypeptide and non-polypeptide fractions. Having separated the polypeptide from other proteins and peptides, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Particularly efficient methods of purifying peptides are fast protein liquid chromatography and HPLC.

Where the term "substantially purified" or "substantially isolated" is used, this designation will refer to a composition in which the protein or peptide forms the major component of the composition, such as constituting about 50%, about 60%, about 70%, about 80%, about 90%, about 95% or more of the proteins in the composition.

V. Cancer

Certain aspects of the present invention relate to the treatment and imaging of cancer. For example, a CPP conjugated to an anti-cancer compound (e.g., R11-PPL) may also be used to treat a cancer, hyperproliferative disease, or other disease characterized by an undesirable proliferation of cells. In certain embodiments, the cancer has originated in the bladder, blood, bone, bone marrow, brain, colon, esophagus, gastrointestine, head, kidney, liver, lung, nasopharynx, neck, pancreas, prostate, skin, stomach, testis, tongue, or uterus. The cancer may be a premalignant, a malignant or a metastatic cancer.

Various other anti-cancer compounds may be conjugated to a cell permeable peptide (e.g., R11) of the present invention. These anti-cancer compounds include, but are not limited to, traditional small molecules, radiotherapeutics, anti-angiogenic compounds, pro-apoptotic compounds, and bioactive polypeptides. An anti-cancer compound of the present invention is preferably comprised in a pharmaceutical preparation.

A. Prostate Cancer

Certain preferred embodiments of the present invention relate to the treatment and imaging of prostate cancer (PCa). In particular, certain compositions of the present invention (e.g., R11 conjugated to an anti-cancer compound or peptide) may be used to treat and/or image a prostate cancer.

Clinical observations indicate that PCa is a typical androgen-dependent disease and pre-pubertal castrates in eunuchs do not develop PCa (Hamilton and Mestler, 1969; Lipsett, 1979; Wagenseil, 1933; Zhou et al., 2001; Huggins and Hodges, 1972; Huggins and Hodges, 2002a; Huggins and Hodges, 2002b; Miyamoto et al., 2004; Yeh et al., 1998). This suggests that all the steps of PCa carcinogenesis are prevented by prostatic atrophy associated with early castration or androgen deprivation. Animal models, first developed (Noble, 1977; Pollard and Luckert, 1984; Lucia et al., 1998; Pollard, 1980; Pollard and Luckert, 1985) in which chronic administration of androgen and/or estrogen to certain strains of intact male rats caused PCa, further support these observations. Current effective therapeutic modalities, first developed by Huggins and Hodges (1941), interrupt the positive effect of growth stimulation by androgen. Androgen thus appears to be a "pure" mitogen for the growth of PCa cells. In contrast, the morphogenic effect of androgen on normal prostatic epithelium must be impaired during the malignant process (Zhou et al., 2001).

Despite the initial responsiveness of PCa toward androgen ablation, tumor cells invariably relapse to an androgen-refractory state that ultimately leads to mortality (Zhou et al., 2001); Bruchovsky et al., 1990). Works by a series of investigators suggest that PCa is a multifocal disease, which represents a heterogeneous cell population with a mixture of AD (dependent on androgen for survival), androgen-sensitive (stimulated by androgen but not dying in their absence), and AI (neither stimulated nor dying in the presence or absence of androgen) cells (Zhou et al., 2001). Treatment by androgen withdrawal would only affect AD cells and would not eliminate androgen-sensitive or AI cells.

Cell lines including C4-2 and PC-3 cells are useful for evaluating PCa responses because C4-2, an androgen responsive cell expressing PSMA, causes osteoblastic lesions (Chen et al., 1998; Lin et al., 2001; Liu et al., 2004); and PC-3, a PSMA-devoid AIPCa cell with a neuroendocrine phenotype, causes osteolytic lesions (Lee et al., 1993; Webber et al., 1996; Webber et al., 1997a; Webber et al., 1997b). These two cell lines represent a spectrum of PCa progression.

1. Diagnostics

Prostate cancer screening is an attempt to find unsuspected cancers. Screening tests may lead to more specific follow-up tests such as a biopsy, where small pieces of the prostate are removed for closer study. As of 2006 prostate cancer screening options include the digital rectal exam and the prostate specific antigen (PSA) blood test. Screening for prostate cancer is controversial because it is not clear if the benefits of screening outweigh the risks of follow-up diagnostic tests and cancer treatments.

Prostate cancer is a slow-growing cancer, very common among older men. In fact, most prostate cancers never grow to the point where they cause symptoms, and most men with prostate cancer die of other causes before prostate cancer has an impact on their lives. The PSA screening test may detect these small cancers that would never become life threatening. Doing the PSA test in these men may lead to overdiagnosis, including additional testing and treatment. Follow-up tests, such as prostate biopsy, may cause pain, bleeding and infection. Prostate cancer treatments may cause urinary incontinence and erectile dysfunction. Therefore, it is essential that the risks and benefits of diagnostic procedures and treatment be carefully considered before PSA screening.

Prostate cancer screening generally begins after age 50, but this can vary due to ethnic backgrounds. Thus, the American Academy of Family Physicians and American College of Physicians recommend the physician discuss the risks and benefits of screening and decide based on individual patient preference. Although there is no officially recommended cut-off, many health care providers stop monitoring PSA in men who are older than 75 years old because of concern that prostate cancer therapy may do more harm than good as age progresses and life expectancy decreases.

Digital rectal examination (DRE) is a procedure where the examiner inserts a gloved, lubricated finger into the rectum to check the size, shape, and texture of the prostate. Areas which are irregular, hard or lumpy need further evaluation, since they may contain cancer. Although the DRE only evaluates the back of the prostate, 85% of prostate cancers arise in this part of the prostate. Prostate cancer which can be felt on DRE is generally more advanced. The use of DRE has never been shown to prevent prostate cancer deaths when used as the only screening test.

The PSA test measures the blood level of prostate-specific antigen, an enzyme produced by the prostate. Specifically, PSA is a serine protease similar to kallikrein. Its normal function is to liquify gelatinous semen after ejaculation, allowing spermatazoa to more easily navigate through the uterine cervix.

PSA levels under 4 ng/mL (nanograms per milliliter) are generally considered normal, however in individuals below the age of 50 sometimes a cutoff of 2.5 is used for the upper limit of normal, while levels over 4 ng/mL are considered abnormal (although in men over 65 levels up to 6.5 ng/mL may be acceptable, depending upon each laboratory's reference ranges). PSA levels between 4 and 10 ng/mL indicate a risk of prostate cancer higher than normal, but the risk does not seem to rise within this six-point range. When the PSA level is above 10 ng/mL, the association with cancer becomes stronger. However, PSA is not a perfect test. Some men with prostate cancer do not have an elevated PSA, and most men with an elevated PSA do not have prostate cancer.

PSA levels can change for many reasons other than cancer. Two common causes of high PSA levels are enlargement of the prostate (benign prostatic hypertrophy (BPH)) and infection in the prostate (prostatitis). It can also be raised for 24 hours after ejaculation and several days after catheterization. PSA levels are lowered in men who use medications used to treat BPH or baldness. These medications, finasteride (marketed as Proscar or Propecia) and dutasteride (marketed as Avodart), may decrease the PSA levels by 50% or more.

Several other ways of evaluating the PSA have been developed to avoid the shortcomings of simple PSA screening. The use of age-specific reference ranges improves the sensitivity and specificity of the test. The rate of rise of the PSA over time, called the PSA velocity, has been used to evaluate men with PSA levels between 4 and 10 ng/ml, but as of 2006, it has not proven to be an effective screening test. Comparing the PSA level with the size of the prostate, as measured by ultrasound or magnetic resonance imaging, has also been studied. This comparison, called PSA density, is both costly and, as of 2006, has not proven to be an effective screening test. PSA in the blood may either be free or bound to other proteins. Measuring the amount of PSA which is free or bound may provide additional screening information, but as of 2006, questions regarding the usefulness of these measurements limit their widespread use.

When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

If cancer is suspected, a biopsy is offered. During a biopsy a urologist obtains tissue samples from the prostate via the rectum. A biopsy gun inserts and removes special hollow-core needles (usually three to six on each side of the prostate) in less than a second. Prostate biopsies are routinely done on an outpatient basis and rarely require hospitalization. Fifty-five percent of men report discomfort during prostate biopsy.

The tissue samples are then examined under a microscope to determine whether cancer cells are present, and to evaluate the microscopic features of any cancer found. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastisis—opposite to what is found in many other cancers that metastisize.

2. Prostate Cancer Therapies

Prostate cancer can be treated with surgery, radiation therapy, hormonal therapy, occasionally chemotherapy, proton therapy, or some combination of these. The age and underlying health of the man as well as the extent of spread, appearance under the microscope, and response of the cancer to initial treatment are important in determining the outcome of the disease. Since prostate cancer is a disease of older men, many will die of other causes before a slowly advancing prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life.

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.). Most men who choose watchful waiting for early stage tumors eventually have signs of tumor progression, and they may need to begin treatment within three years. Although men who choose watchful waiting avoid the risks of surgery and radiation, the risk of metastasis (spread of the cancer) may be increased. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy.

Clinically insignificant prostate tumors are often found by accident when a doctor incorrectly orders a biopsy not following the recommended guidelines (abnormal DRE and elevated PSA). The urologist must check that the PSA is not elevated for other reasons, Prostatitis, etc. An annual biopsy is often recommended by a urologist for a patient who has selected watchful waiting when the tumor is clinically insignificant (no abnormal DRE or PSA). The tumors tiny size can be monitored this way and the patient can decide to have surgery only if the tumor enlarges which may take many years or never.

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radical prostatectomy is effective for tumors which have not spread beyond the prostate; cure rates depend on risk factors such as PSA level and Gleason grade. However, it may cause nerve damage that significantly alters the quality of life of the prostate cancer survivor. The most common serious complications are loss of urinary control and impotence. Reported rates of both complications vary widely depending on how they are assessed, by whom, and how long after surgery, as well as the setting (e.g., academic series vs. community-based or population-based data). Although penile sensation and the ability to achieve orgasm usually remain intact, erection and ejaculation are often impaired. Medications such as sildenafil (Viagra), tadalafil (Cialis), or vardenafil (Levitra) may restore some degree of potency. For most men with organ-confined disease, a more limited "nerve-sparing" technique may help avoid urinary incontinence and impotence.

Radical prostatectomy has traditionally been used alone when the cancer is small. In the event of positive margins or locally advanced disease found on pathology, adjuvant radiation therapy may offer improved survival. Surgery may also be offered when a cancer is not responding to radiation therapy. However, because radiation therapy causes tissue changes, prostatectomy after radiation has a higher risk of complications.

Transurethral resection of the prostate, commonly called a "TURP," is a surgical procedure performed when the tube from the bladder to the penis (urethra) is blocked by prostate enlargement. TURP is generally for benign disease and is not meant as definitive treatment for prostate cancer. During a TURP, a small tube (cystoscope) is placed into the penis and the blocking prostate is cut away.

In metastatic disease, where cancer has spread beyond the prostate, removal of the testicles (called orchiectomy) may be done to decrease testosterone levels and control cancer growth.

Radiation therapy, also known as radiotherapy, uses ionizing radiation to kill prostate cancer cells. When absorbed in tissue, ionizing radiation such as $\gamma$ and x-rays damage the DNA in cells, which increases the probability of apoptosis. Two different kinds of radiation therapy are used in prostate cancer treatment: external beam radiation therapy and brachytherapy.

External beam radiation therapy uses a linear accelerator to produce high-energy x-rays which are directed in a beam towards the prostate. A technique called Intensity Modulated Radiation Therapy (IMRT) may be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center. New types of radiation therapy may have fewer side effects then traditional treatment, one of these is Tomotherapy.

Permanent implant brachytherapy is a popular treatment choice for patients with low to intermediate risk features, can be performed on an outpatient basis, and is associated with good 10-year outcomes with relatively low morbidity. It involves the placement of about 100 small "seeds" containing radioactive material (such as iodine-125 or palladium-103) with a needle through the skin of the perineum directly into the tumor while under spinal or general anesthetic. These seeds emit lower-energy X-rays which are only able to travel a short distance. Although the seeds eventually become inert, they remain in the prostate permanently. The risk of exposure to others from men with implanted seeds is generally accepted to be insignificant.

Radiation therapy is commonly used in prostate cancer treatment. It may be used instead of surgery for early cancers, and it may also be used in advanced stages of prostate cancer to treat painful bone metastases. Radiation treatments also can be combined with hormonal therapy for intermediate risk disease, when radiation therapy alone is less likely to cure the cancer. Some radiation oncologists combine external beam radiation and brachytherapy for intermediate to high risk situations. One study found that the combination of six months of androgen suppressive therapy combined with external beam radiation had improved survival compared to radiation alone in patients with localized prostate cancer. Others use a "triple modality" combination of external beam radiation therapy, brachytherapy, and hormonal therapy.

Less common applications for radiotherapy are when cancer is compressing the spinal cord, or sometimes after surgery, such as when cancer is found in the seminal vesicles, in the lymph nodes, outside the prostate capsule, or at the margins of the biopsy.

Radiation therapy is often offered to men whose medical problems make surgery more risky. Radiation therapy appears to cure small tumors that are confined to the prostate just about as well as surgery. However, as of 2006 some issues remain unresolved, such as whether radiation should be given to the rest of the pelvis, how much the absorbed dose should be, and whether hormonal therapy should be given at the same time.

Side effects of radiation therapy might occur after a few weeks into treatment. Both types of radiation therapy may cause diarrhea and rectal bleeding due to radiation proctitis, as well as urinary incontinence and impotence. Symptoms tend to improve over time. Men who have undergone external beam radiation therapy will have a higher risk of later developing colon cancer and bladder cancer.

Cryosurgery is another method of treating prostate cancer. It is less invasive than radical prostatectomy, and general anesthesia is less commonly used. Under ultrasound guidance, metal rods are inserted through the skin of the perineum into the prostate. Highly purified Argon gas is used to cool the rods, freezing the surrounding tissue at $-196°$ C. ($-320°$ F.). As the water within the prostate cells freeze, the cells die. The urethra is protected from freezing by a catheter filled with warm liquid. Cryosurgery generally causes fewer problems with urinary control than other treatments, but impotence occurs up to ninety percent of the time. When used as the initial treatment for prostate cancer and in the hands of an experienced cryosurgeon, cryosurgery has a 10 year biochemical disease free rate superior to all other treatments including radical prostatectomy and any form of radiation Cryosurgery has also been demonstrated to be superior to radical prostatectomy for recurrent cancer following radiation therapy.

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It may also be given to certain men undergoing radiation therapy or surgery to help prevent return of their cancer.

Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

There are several forms of hormonal therapy. Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Antiandrogens are medications such as flutamide, bicalutamide, nilutamide, and cyproterone acetate which directly block the actions of testosterone and DHT within prostate cancer cells.

Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using antiandrogens.

GnRH action can be interrupted in one of two ways. GnRH antagonists suppress the production of LH directly, while GnRH agonists suppress LH through the process of down-regulation after an initial stimulation effect. Abarelix is an example of a GnRH antagonist, while the GnRH agonists include leuprolide, goserelin, triptorelin, and buserelin. Initially, GnRH agonists increase the production of LH. However, because the constant supply of the medication does not match the body's natural production rhythm, production of both LH and GnRH decreases after a few weeks.

As of 2006 the most successful hormonal treatments are orchiectomy and GnRH agonists. Despite their higher cost, GnRH agonists are often chosen over orchiectomy for cosmetic and emotional reasons. Eventually, total androgen blockade may prove to be better than orchiectomy or GnRH agonists used alone.

Each treatment has disadvantages which limit its use in certain circumstances. Although orchiectomy is a low-risk surgery, the psychological impact of removing the testicles can be significant. The loss of testosterone also causes hot flashes, weight gain, loss of libido, enlargement of the breasts (gynecomastia), impotence and osteoporosis. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer.

Bone pain due to metastatic disease is treated with opioid pain relievers such as morphine and oxycodone. External beam radiation therapy directed at bone metastases may provide pain relief. Injections of certain radioisotopes, such as strontium-89, phosphorus-32, or samarium-153, also target bone metastases and may help relieve pain.

High Intensity Focused Ultrasound (HIFU) for prostate cancer utilizes ultrasonic waves to ablate/destroy the tissue of the prostate. During the HIFU procedure, sound waves are used to heat the prostate tissue thus destroying the cancerous cells. Essentially, ultrasonic waves are precisely focused on specific areas of the prostate to eliminate the prostate cancer with minimal risks of effecting other tissue or organs. Temperatures at the focal point of the sound waves can exceed 100° C. The ability to focus the ultrasonic waves leads to a relatively low occurrence of both incontinence and impotence. (0.6% and 0-20%, respectively). According to international studies, when compared to other procedures, HIFU has a high success rate with a reduced risk of side effects. Studies using the Sonablate 500 HIFU machine have shown that 94% of patients with a pretreatment PSA (Prostate Specific Antigen) of less than 10 g/ml were cancer-free after three years. However, many studies of HIFU were performed by manufacturers of HIFU devices, or members of manufacturers' advisory panels.

HIFU was first used in the 1940's and 1950's in efforts to destroy tumors in the central nervous system. Since then, HIFU has been shown to be effective at destroying malignant tissue in the brain, prostate, spleen, liver, kidney, breast, and bone. Today, the HIFU procedure for prostate cancer is performed using a transrectal probe. This procedure has been performed for over ten years and is currently approved for use in Japan, Europe, Canada, and parts of Central and South America.

Although not yet approved for use in the Unites States, many patients have received the HIFU procedure at facilities in Canada, and Central and South America. Currently, therapy is available using the Sonablate 500 or the Ablatherm. The Sonablate 500 is designed by Focus Surgery of Indianapolis, Ind. and is used in international HIFU centers around the world.

Several medications and vitamins may also help prevent prostate cancer. Two dietary supplements, vitamin E and selenium, may help prevent prostate cancer when taken daily. Estrogens from fermented soybeans and other plant sources (called phytoestrogens) may also help prevent prostate cancer. The selective estrogen receptor modulator drug toremifene has shown promise in early trials. Two medications which block the conversion of testosterone to dihydrotestosterone, finasteride and dutasteride, have also shown some promise. As of 2006 the use of these medications for primary prevention is still in the testing phase, and they are not widely used for this purpose. The problem with these medications is that they may preferentially block the development of lower-grade prostate tumors, leading to a relatively greater chance of higher grade cancers, and negating any overall survival improvement. Green tea may be protective (due to its polyphenol content), though the data is mixed. A 2006 study of green tea derivatives demonstrated promising prostate cancer prevention in patients at high risk for the disease. In 2003, an Australian research team led by Graham Giles of The Cancer Council Australia concluded that frequent masturbation by males appears to help prevent the development of prostate cancer. Recent research published in the Journal of the National Cancer Institute suggests that taking multivitamins more than seven times a week can increase the risks of contracting the disease. This research was unable to highlight the exact vitamins responsible for this increase (almost double), although they suggest that vitamin A, vitamin E and beta-carotene may lie at its heart. It is advised that those taking multivitamins never exceed the stated daily dose on the label. Scientists recommend a healthy, well balanced diet rich in fiber, and to reduce intake of meat. A 2007 study published in the Journal of the National Cancer Institute found that men eating cauliflower, broccoli, or one of the other cruciferous vegetables, more than once a week were 40% less likely to develop prostate cancer than men who rarely ate those vegetables. Scientists believe the reason for this phenomenon has to do with a phytochemical called Diindolylmethane in these vegetables that has anti-androgenic and immune modulating properties. This compound is currently under investigation by the National Cancer Institute as a natural therapeutic for prostate cancer.

B. Bladder Cancer

Bladder cancer refers to any of several types of malignant growths of the urinary bladder, with over 65,000 new cases and some 13,750 attributed deaths reported in 2007 alone. It is a disease in which abnormal cells multiply without control in the bladder. The bladder is a hollow, muscular organ that stores urine; it is located in the pelvis. The most common type of bladder cancer begins in cells lining the inside of the bladder and is called urothelial cell or transitional cell carcinoma (UCC or TCC).

Bladder cancer characteristically causes blood in the urine, this may be visible to the naked eye (frank haematuria) or detectable only be microscope (microscopic haematuria). Other possible symptoms include pain during urination, frequent urination or feeling the need to urinate without results. These signs and symptoms are not specific to bladder cancer, and are also caused by non-cancerous conditions, including prostate infections and cystitis.

Exposure to environmental carcinogens of various types is responsible for the development of most bladder cancers. Tobacco use (specifically cigarette smoking) is thought to cause 50% of bladder cancers discovered in male patients and 30% of those found in female patients. Thirty percent of bladder tumors probably result from occupational exposure in the workplace to carcinogens such as benzidine. Occupations at risk are metal industry workers, rubber industry workers, workers in the textile industry and people who work in printing. Hairdressers are thought to be at risk as well because of their frequent exposure to permanent hair dyes. It has been proposed that hair dyes are a risk factor, and some have shown an odds ratio of 2.1 to 3.3 for risk of developing bladder cancer among women who use permanent hair yes, while others have shown no correlation between the use of hair dyes and bladder cancer. Certain drugs such as cyclophosphamide and phenacetin are known to predispose to bladder TCC. Chronic bladder irritation (infection, bladder stones, catheters, bilharzia) predisposes to squamous cell carcinoma of the bladder. Approximately 20% of bladder cancers occur in patients without predisposing risk factors. Bladder cancer is not currently believed to be heritable.

Like virtually all cancers, bladder cancer development involves the acquisition of mutations in various oncogenes and tumor suppressor genes. Genes which may be altered in bladder cancer include FGFR3, HRAS, RB1 and P53. Several genes have been identified which play a role in regulating the cycle of cell division, preventing cells from dividing too rapidly or in an uncontrolled way. Alterations in these genes may help explain why some bladder cancers grow and spread more rapidly than others.

A family history of bladder cancer is also a risk factor for the disease. Many cancer experts assert that some people appear to inherit reduced ability to break down certain chemicals, which makes them more sensitive to the cancer-causing effects of tobacco smoke and certain industrial chemicals.

1. Diagnosis

The gold standard of diagnosing bladder cancer is urine cytology and transurethral (through the urethra) cystoscopy. Urine cytology can be obtained in voided urine or at the time of the cystoscopy ("bladder washing"). Cytology is very specific (a positive result is highly indicative of bladder cancer) but suffers from low sensitivity (a negative result does not exclude the diagnosis of cancer). There are newer urine bound markers for the diagnosis of bladder cancer. These markers are more sensitive but not as specific as urine cytology. They are much more expensive as well. Many patients with a history, signs, and symptoms suspicious for bladder cancer are referred to a urologist or other physician trained in cystoscopy, a procedure in which a flexible tube bearing a camera and various instruments is introduced into the bladder through the urethra. Suspicious lesions may be biopsied and sent for pathologic analysis.

Ninety percent of bladder cancer are transitional cell carcinomas (TCC) that arise from the inner lining of the bladder called the urothelium. The other 10% of tumours are squamous cell carcinoma, adenocarcinoma, sarcoma, small cell carcinoma and secondary deposits from cancers elsewhere in the body.

TCCs are often multifocal, with 30-40% of patients having a more than one tumour at diagnosis. The pattern of growth of TCCs can be papillary, sessile (flat) or carcinoma-in-situ (CIS). The 1973 WHO grading system for TCCs (papilloma, G1, G2 or G3) is most commonly used despite being superseded by the 2004 WHO grading (papillary neoplasm of low malignant potential (PNLMP), low grade and high grade papillary carcinoma. CIS invariably consists of cytologically high grade tumour cells.

Bladder TCC is staged according to the 1997 TNM system:
Ta—non-invasive papillary tumour
T1—invasive but not as far as the muscular bladder layer
T2—invasive into the muscular layer
T3—invasive beyond the muscle into the fat outside the bladder
T4—invasive into surrounding structures like the prostate, uterus or pelvic wall The following stages are used to classify the location, size, and spread of the cancer, according to the TNM (tumor, lymph node, and metastases) staging system:
Stage 0: Cancer cells are found only on the inner lining of the bladder.
Stage I: Cancer cells have proliferated to the layer beyond the inner lining of the urinary bladder but not to the muscles of the urinary bladder.
Stage II: Cancer cells have proliferated to the muscles in the bladder wall but not to the fatty tissue that surrounds the urinary bladder.
Stage III: Cancer cells have proliferated to the fatty tissue surrounding the urinary bladder and to the prostate gland, vagina, or uterus, but not to the lymph nodes or other organs.
Stage IV: Cancer cells have proliferated to the lymph nodes, pelvic or abdominal wall, and/or other organs.
Recurrent: Cancer has recurred in the urinary bladder or in another nearby organ after having been treated.

2. Therapy

The treatment of bladder cancer depends on how deep the tumor invades into the bladder wall. Superficial tumors (those not entering the muscle layer) can be "shaved off" using an electrocautery device attached to a cystoscope.

Immunotherapy in the form of BCG instillation is also used to treat and prevent the recurrence of superficial tumors. BCG immunotherapy is effective in up to ⅔ of the cases at this stage. Instillations of chemotherapy into the bladder can also be used to treat superficial disease. Bacillus Calmette-Guerin (BCG) has been in use since the 1980's, and is the most proven and effective form of immunotherapy at this point in time. BCG is an inactivated form of the bacterium *Mycobacterium tuberculosis*, which is given both intravesically mixed in a saline solution and instilled directly into the bladder via a catheter, as well as in the form of a percutaneous vaccine. Although it is not yet totally understood why BCG and other immunotherapies work against cancer, they are thought to elicit an immune response.

It has been shown that BCG induces a variety of cytokines into the urine of patients with superficial TCC, and that some cytokines have antiangiogenic activity. One study demonstrated that interferon-inducible protein 10 (IP-10) and its inducing anti-angiogenic cytokines, interferon-γ and interleukin-12, are increased during intravesical BCG immunotherapy of bladder TCC. These data suggest that, in addition to a cellular immune response, BCG may induce a cytokine-mediated antiangiogenic environment that aids in inhibiting future tumor growth and progression.

Though side effects vary with the individual, the great majority of people find BCG treatments tolerable with side effects being temporary, and some have no adverse reactions at all. Dysuria (pain or difficulty upon urination) and urinary frequency are expected as a consequence of the inflammatory response, and cystitis is the most frequent adverse reaction-occurring in up to 90% of cases. Blood in the urine may occur with cystitis and is seen in one-third of patients. Irritative bladder symptoms are unlikely in the week after the first intravesical BCG. Side effects of BCG are cumulatory, and generally increase with successive treatments. Some people complain of flu like symptoms including fatigue, joint pain and muscle ache.

Untreated, superficial tumors may gradually begin to infiltrate the muscular wall of the bladder. Tumors that infiltrate the bladder require more radical surgery where part or all of the bladder is removed (a cystectomy) and the urinary stream is diverted. In some cases, skilled surgeons can create a substitute bladder (a neobladder) from a segment of intestinal tissue, but this largely depends upon patient preference, age of patient, renal function, and the site of the disease.

A combination of radiation and chemotherapy can also be used to treat invasive disease. It has not yet been determined how the effectiveness of this form of treatment compares to that of radical ablative surgery. There is weak observational evidence from one very small study (n=84) to suggest that the concurrent use of statins is associated with failure of BCG immunotherapy.

VI. Combination Therapies

In order to increase the effectiveness of a bioactive peptide (e.g., PPL) or other anti-cancer compound optionally conjugated to a cell permeable peptide (e.g., R11), it may be desirable to combine these compositions and methods of the invention with an agent effective in the treatment of hyperproliferative disease, such as, for example, an anti-cancer agent. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

More generally, such an agent would be provided in a combined amount with the bioactive peptide effective to kill or inhibit proliferation of a cancer cell. This process may involve contacting the cell(s) with an agent(s) and the bioactive peptide at the same time or within a period of time wherein separate administration of the bioactive peptide and an agent to a cell, tissue or organism produces a desired therapeutic benefit. This may be achieved by contacting the cell, tissue or organism with a single composition or pharmacological formulation that includes both the bioactive peptide and one or more agents, or by contacting the cell with two or more distinct compositions or formulations, wherein one composition includes the bioactive peptide and the other includes one or more agents.

The terms "contacted" and "exposed," when applied to a cell, tissue or organism, are used herein to describe the process by which a therapeutic construct of the bioactive peptide and/or another agent, such as for example a chemotherapeutic or radiotherapeutic agent, are delivered to a target cell, tissue or organism or are placed in direct juxtaposition with the target cell, tissue or organism. To achieve cell killing or stasis, the bioactive peptide and/or additional agent(s) are delivered to one or more cells in a combined amount effective to kill the cell(s) or prevent them from dividing.

The bioactive peptide may precede, be co-current with and/or follow the other agent(s) by intervals ranging from minutes to weeks. In embodiments where the bioactive peptide, and other agent(s) are applied separately to a cell, tissue or organism, one would generally ensure that a significant period of time did not expire between the time of each delivery, such that the bioactive peptide and agent(s) would still be able to exert an advantageously combined effect on the cell, tissue or organism. For example, in such instances, it is contemplated that one may contact the cell, tissue or organism with two, three, four or more modalities substantially simultaneously (i.e. within less than about a minute) as the bioactive peptide. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the bioactive peptide.

Various combination regimens of the bioactive peptide and one or more agents may be employed. Non-limiting examples of such combinations are shown below, wherein a composition of the bioactive peptide is "A" and an agent is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the composition of the bioactive peptide to a cell, tissue or organism may follow general protocols for the administration of chemotherapeutics, taking into account the toxicity, if any. It is expected that the treatment cycles would be repeated as necessary. In particular embodiments, it is contemplated that various additional agents may be applied in any combination with the present invention.

A. Chemotherapeutic Agents

The term "chemotherapy" refers to the use of drugs to treat cancer. A "chemotherapeutic agent" is used to connote a compound or composition that is administered in the treatment of cancer. One subtype of chemotherapy known as biochemotherapy involves the combination of a chemotherapy with a biological therapy.

Chemotherapeutic agents include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference," Goodman & Gilman's "The Pharmacological Basis of Therapeutics," "Remington's Pharmaceutical Sciences," and "The Merck Index, Eleventh Edition," incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Examples of specific chemotherapeutic agents and dose regimes are also described herein. Of course, all of these dosages and agents described herein are exemplary rather than limiting, and other doses or agents may be used by a skilled artisan for a specific patient or application. Any dosage in-between these points, or range derivable therein is also expected to be of use in the invention.

B. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

C. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

D. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

E. Gene Therapy

In yet another embodiment, the secondary treatment is a gene therapy in which a therapeutic polynucleotide is administered before, after, or at the same time as an anti-cancer compound conjugated to a CPP. Delivery of a vector encoding either a full length or truncated anti-cancer gene in conjunction with an anti-cancer compound conjugated to a CPP will have a combined anti-hyperproliferative effect on target tissues. Anti-cancer genes are known in the art and include, e.g., p53, etc.

F. Surgery

As discussed above, surgery is a first line therapy for prostate cancer, and may be combined with other therapies, such as the treatment of the present invention, chemotherapy, radiotherapy, hormonal therapy, gene therapy, immunotherapy and/or alternative therapies. The treatments of the present invention may, in particular, be used to render a tumor more resectable, or to make a non-resectable tumor resectable.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

VII. Pharmaceutical Preparations

Pharmaceutical compositions of the present invention comprise an effective amount of one or more a bioactive peptide (e.g., PPL) or other anti-cancer compound optionally conjugated to a cell permeable peptide (e.g., R11) or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one a bioactive peptide (e.g., PPL) or other anti-cancer compound optionally conjugated to a cell permeable peptide (e.g., R11) or additional active ingredient will be known to those of skill in the art in light of the present disclosure, as exemplified by Remington: The Science and Practice of Pharmacy, $21^{ST}$ Ed. (2005), incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the pharmaceutical compositions is contemplated.

The a bioactive peptide (e.g., PPL) or other anti-cancer compound optionally conjugated to a cell permeable peptide (e.g., R11) may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences (1990), incorporated herein by reference).

The a bioactive peptide (e.g., PPL) or other anti-cancer compound optionally conjugated to a cell permeable peptide (e.g., R11) may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a bioactive peptide (e.g., PPL) or other anti-cancer compound optionally conjugated to a cell permeable peptide (e.g., R11), one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the a bioactive peptide (e.g., PPL) or other anti-cancer compound optionally conjugated to a cell permeable peptide (e.g., R11) may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the a bioactive peptide (e.g., PPL) or other anti-cancer compound optionally conjugated to a cell permeable peptide (e.g., R11) are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitzs et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, a bioactive peptide (e.g., PPL) or other anti-cancer compound optionally conjugated to a cell permeable peptide (e.g., R11) may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intratumoral intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences," 1980). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound a bioactive peptide (e.g., PPL) or other anti-cancer compound optionally conjugated to a cell permeable peptide (e.g., R11) may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch." For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture and peptide incubation. All PCa cell lines (LNCaP, C4-2, LAPC4 and PC3) were maintained as described previously (Zhou et al., 2005). To determine the peptide uptake, $1 \times 10^5$ cells per well were plated in a 12-well plate. Next day, the culture medium was replaced with RPMI medium supplemented with 0.5% FBS (Invitrogen, Carlsbad, Calif.) containing different concentrations fluorescence (FITC)-tagged peptides and incubation was carried out at the indicated time. For determining cellular location of peptide, cells were cultured overnight in slide chamber at a density of $25 \times 10^4/cm^2$. The FITC tagged peptides were incubated for 30 minutes in the presence of RPMI medium supplemented with 0.5% of FBS prior to fluorescence microscopy.

Peptide synthesis. All peptides TAT ($^{FITC}$-G-RKKRRQRRR (SEQ ID NO:1)), PENE ($^{FITC}$-G-RQIKIW-FQNRRMKWKK (SEQ ID NO:2)), KALA ($^{FITC}$-G-KLA-LKLALKALKAALKLA (SEQ ID NO:3)), homopolymers of L-arginine R11 ($^{FITC}$-G-R$_{11}$; SEQ ID NO:6), homopolymers of L-lysine K11 ($^{FITC}$-G-K$_{11}$; SEQ ID NO 10), AAL (FQL-RQAALVASRKGE (SEQ ID NO:4)), PPL (FQLRQP-PLVPSRKGE (SEQ ID NO:5)), R11AAL($^{FITC}$-G-RRRRRRRRRRR -GG-FQLRQAALVASRKGE (SEQ ID NO:11)) and R11ppl ($^{FITC}$-G-RRRRRRRRRRR-GGG-FQL-RQPPLVPSRKGE (SEQ ID NO:12)) were synthesized by automated peptide synthesizer using the standard solid phase chemistry, purified by reverse phase HPLC and analyzed by mass spectrometry. The amount of peptide were determined by mass spectrometry and normalized by fluorescence intensity.

Fluorescence intensity determination and Fluorescence microscopy. To determine the uptake efficiency of each CPP, different concentrations (0.1, 1, 5 µM) of fluorescence (FITC)-tagged peptides were incubated with cells for 30 minutes (or different time for the time course study) then cells were washed twice with PBS and trypsinized. After washing with PBS twice, the total cell number was determined and cells were lysed in Tris Buffer (50 mM Tris-HCl, pH7.5, 150 mM NaCl, 5 mM EDTA, 1% Triton X100). The fluorescence intensity was examined by fluorometer (excitation 490-500 nm; emission 515-525 nm).

To determine the cellular localization of CPP, after 30-minute incubation, cells were fixed with 4% paraformaldehyde in PBS plus DAPI (1 μg/ml) counterstaining (Sigma, St. Louis, Mo.) and cells were examined under fluorescence microscope.

Cell growth assay and cell cycle analysis. Cells were plated in 96-well plate at a density of $10^3$ per well in T-medium supplemented with 5% charcoal-stripped FBS for overnight. Cells were incubated with or without indicated peptides (5 μM) for 3 hours in the presence of T-medium supplemented with 0.5% charcoal-stripped FBS. Subsequently, cells were replaced with T-medium containing either 5% FBS or 10 nM dihydrotestosterone (DHT). The peptides were changed every 2 days. The cell proliferation was determined 4 days after the initial peptide treatment by using 3-(4,5-dimethylthiazol-2-yl)-2,5-diphenyltetrazolium bromide (MTT) assay (Roche, Indianapolis, Ind.).

Western blot analysis. Cells were plated in 6-well plates ($2\times10^5$ per well) with T medium containing 5% FBS. Next day, cells were switched to lower serum condition (0.5% FBS) for another 24 hours. After incubating with indicated peptides (5 μM) for 3 hours, 10 ng/ml EGF (Upstate, Charlottesville, Va.) or FBS was added to the culture and cells were harvested at the indicated time. The cell lysate was prepared using SDS PAGE sample buffer and subjected to 10% SDS-PAGE then probed with primary antibody. The protein intensity was detected using an enhanced chemiluminescence detection kit (Amersham, Piscataway, N.J.). Antibodies used in this study were: phospho-Erk1/2 (αpErk; Cell Signaling, Beverley, Mass.); Erk2 (αErk2; Santa Cruz, Santa Cruz, Calif.).

In vitro pull down assay. As described previously (Zhou et al., 2003), cell lysate was prepared in 0.5 ml of lysis buffer (50 mM Tris-HCl, pH 7.5, 150 mM NaCl, 5 mM EDTA supplemented with 1% Triton X-100, plus protease inhibitors cocktail), after a low speed spin, 0.4 ml of supernatant was collected and incubated with 30 μl of GST-SH3 fusion protein with glutathione-Sepharose overnight at 4° C. The increasing concentrations of peptide (10, 30, 100 μM) for R11PPL or R11AAL were also added during the incubation. Next day, pellet was washed twice with lysis buffer and dissolved in the sample buffer and then subjected to western blot analysis probed with antibodies against SOS (αSOS; Upstate, Charlottesville, Va.).

Example 2

R11-PPL Inhibits Cancer Cell Growth

Screening of the most efficient CPP uptake by prostate cancer (PCa) cell lines. To deliver small peptide into target cells, CPP was employed as a delivery system. Five different CPPs were synthesized including TAT (amino acid 49-57), Penetratin (Antennapedia 43-58) (PENE), KALA peptide, poly-arginine (R11) and poly-lysine (K11). All the CPPs were incorporated with a FITC-labeled glycine at their N-terminal ends. From initial observation under fluorescence microscope, the inventors found that all five CPPs exhibited positive staining on cells without fixation and R11 appeared to have stronger staining than others. To determine the uptake quantitatively, fluorometer was used to measure the intensity of each CPP per cell basis. To rule out the possible artifacts such as CPP only associated with the cell surface and the pH variation from different organelles, cells were trypsinized and washed extensively with PBS, and a buffer with neutral pH was used in this experiment. As shown in FIG. 1A, a dose-dependent CPP uptake by four different PCa cells (i.e., LNCaP, C4-2, LAPC4 and PC3) was observed. Nevertheless, R11 had exhibited the highest uptake (at least 6-fold higher than other CPPs) among four PCa cell lines tested; in contrast, K11 had the lowest uptake efficiency by PCa cells (FIG. 1A). In general, the uptake efficiency of five different CPPs tested can be considered as R11>>KALA≧TAT≧PENE≧K11 among four PCa cells. In addition, using fluorescence-activated cell sorting technique, R11 at the lowest concentration could give rise to 100% cells with positive staining compared with the other four CPPs. Thus, the data indicate that R11 has a specific uptake by PCa cells.

Figure 1B:
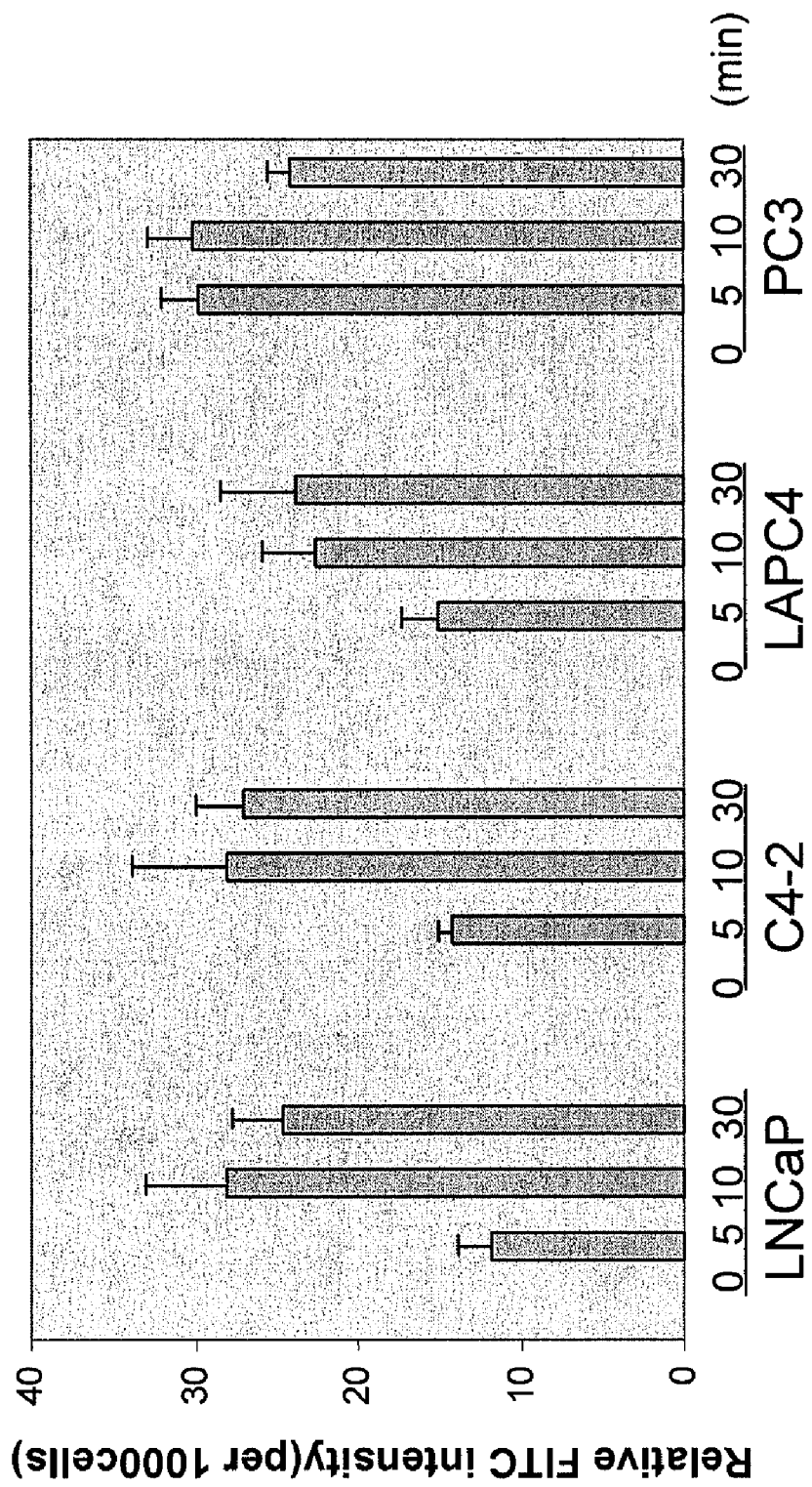
Figure 1C:
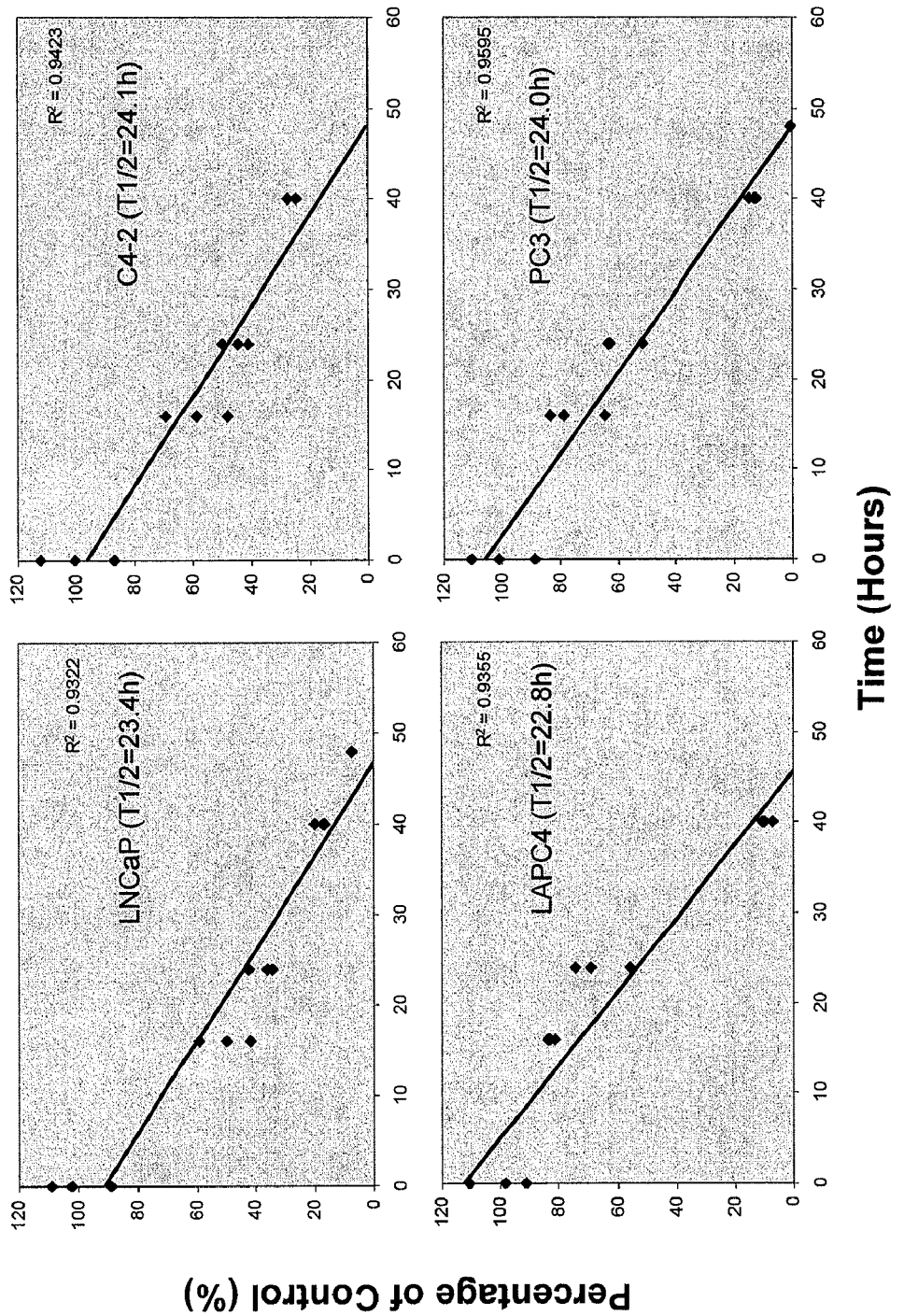

It is known that CPPs can enter cell very rapidly (Wadia and Dowdy, 2005). Therefore, the dynamics of R11 uptake was evaluated by incubating cells with 5 μM R11 for 5, 10 and 30 minutes. As shown in FIG. 1B, the fluorescence intensity reached plateau at 10-minute incubation for four PCa cell lines. The half maximal intensity can be reached at 5-minute incubation for LNCaP, C4-2 and LAPC4 cells. It appeared that PC3 cell had much rapid uptake rate than the other PCa cells; it already reached plateau at 5-minute incubation (FIG. 1B). The half-life of R11 in each cell line was further examined by pulsing cells with FITC-labeled R11 (5 μM) for 30 minutes then removing any free R11. As shown in FIG. 1C, 48 hours after R11 incubation, the fluorescence intensity in each cell returned to the background level. Thus, the half-life of R11 in LNCaP, C4-2, LAPC4 and PC3 is 23.4, 24.1, 22.8 and 24.0 hours respectively using linear regression analysis. These data conclude that R11 is a rapid delivery vehicle for a variety of PCa cells with its in vitro half-life about 23-24 hours.

Design of small peptide conjugated with R11. To engineer small peptide with R11 as a potential tumor inhibitor, DOC-2/DAB2 protein was used as a model. The previous data have clearly indicated that three PR domains in DOC-2/DAB2 have their specific affinity to various SH3-containing proteins (Zhou and Hsieh, 2001; Zhou et al., 2003). Nevertheless, the second PR domain (i.e, PPL) can interact with many SH3-containing proteins tested. R11PPL was synthesized by conjugating FITC-R11 (N-terminus) with PPL in the C-terminus separated by three glycines. On the other hand, the control peptide R11AAL was synthesized identically with R11PPL except that all the proline was replaced with alanine.

Figure 2A:
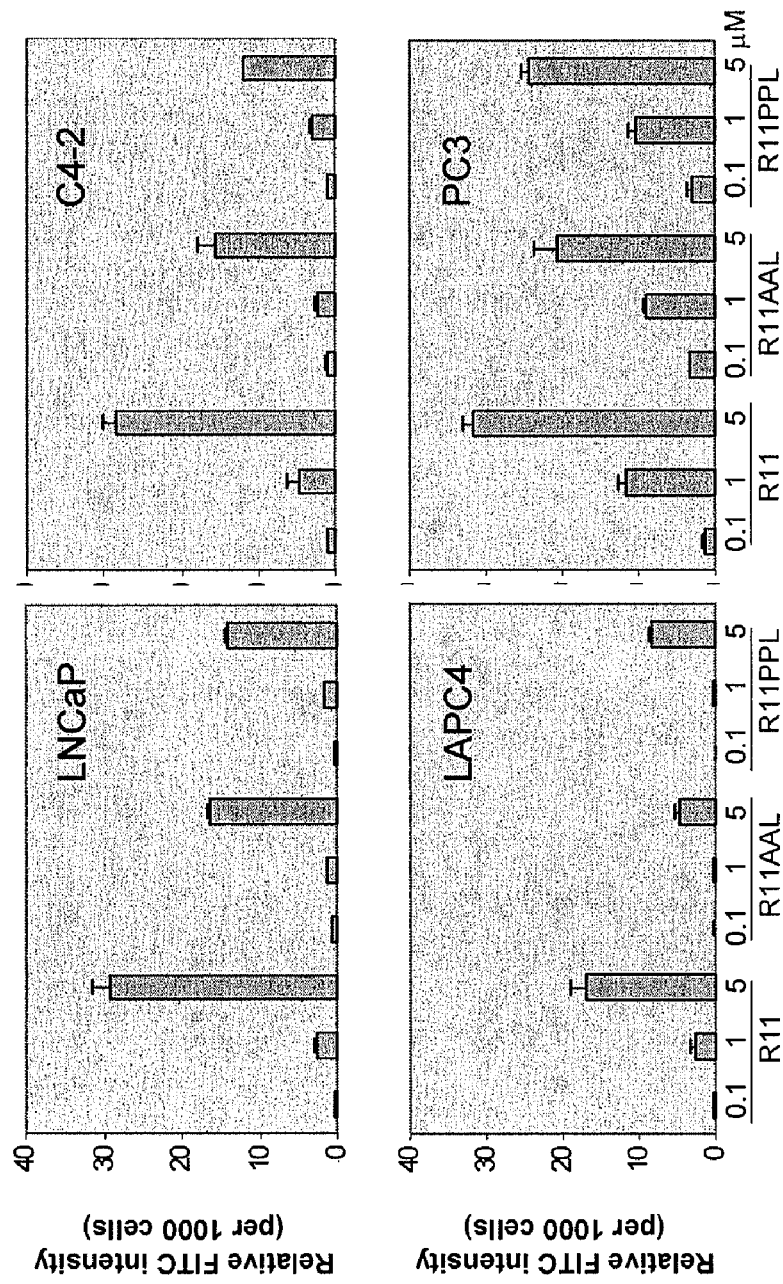
FIGS. 2A-B—Uptake of peptide R11PPL and R11AAL by PCa cells.
Figure 2B:
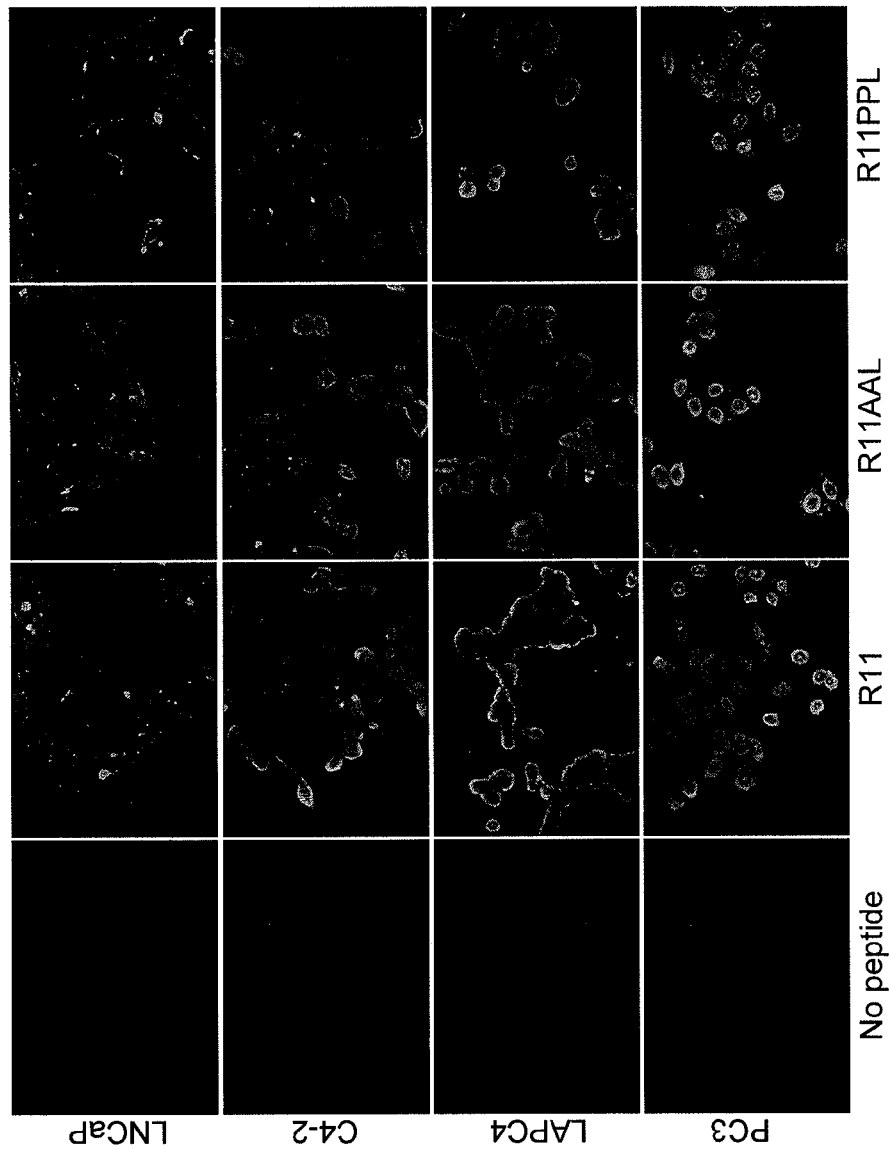

The uptake of R11PPL and R11AAL in four different PCa cells were examined and the data (FIG. 2A) indicated that the uptake of R11AAL and R11PPL by these cells tested was very similar. However, R11 appeared to have higher uptake than R11AAl or R11PPL; it may be due to the length of small peptide and/or charge/mass ratio. To further characterizing the cellular localization of R11AAL and R11PPL in PCa cells, fluorescence images were taken from the cells incubated with these peptides for 30 minutes. Based on this observation, there is no major difference in terms of cellular localization whether cells have been fixed or not. As shown in FIG. 2B, R11AAL and R11PPL exhibited a similar pattern as compared to R11 in these four PCa cells. The majority of peptides were localized in the cytosol with few nuclear staining. Noticeably, in LAPC4 cells, an intense staining of peptides was associated with plasma membrane. In PC3 cells, it seemed to be a perinuclear staining of these peptides. Nevertheless, these data indicate that both R11AAL and R11PPL exhibit the same cellular distribution as R11 although R11 has a higher uptake than R11AAL and R11PPL.

Figure 3A:
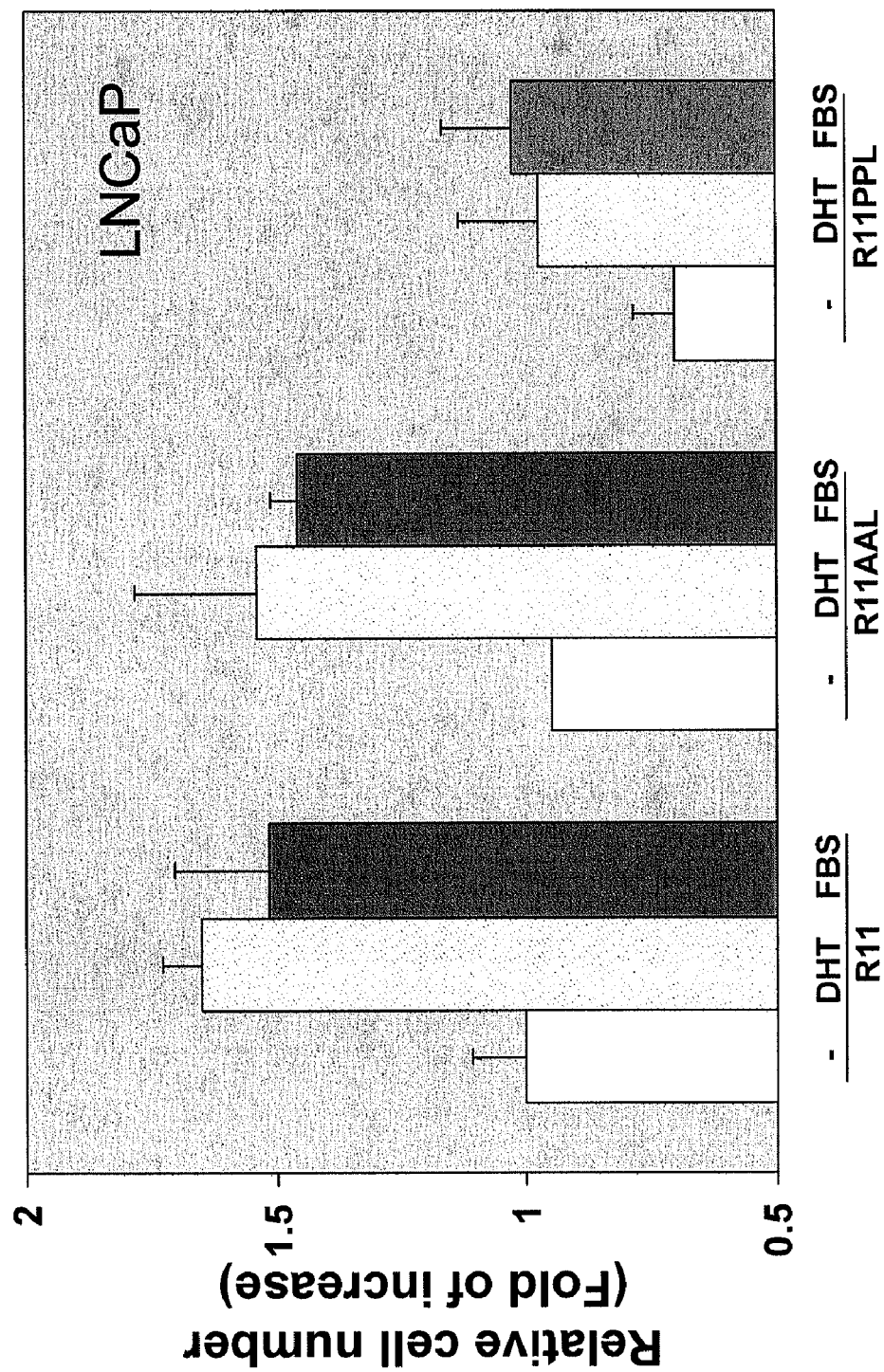
FIGS. 3A-B—Inhibitory effect of R11PPL on serum and androgen-induced cell proliferation of PCa. LNCaP (FIG. 3A) or C4-2 cells (FIG. 3B) were incubated with 5 μM R11PPL, R11AAL or without peptide 3 hours before adding serum or DHT (10 nM) and relative cell number was determined by MTT assay. All the experiments were carried out in quadruplicates and repeated at least twice. Each column represents mean±SD in triplicate.
Figure 3B:
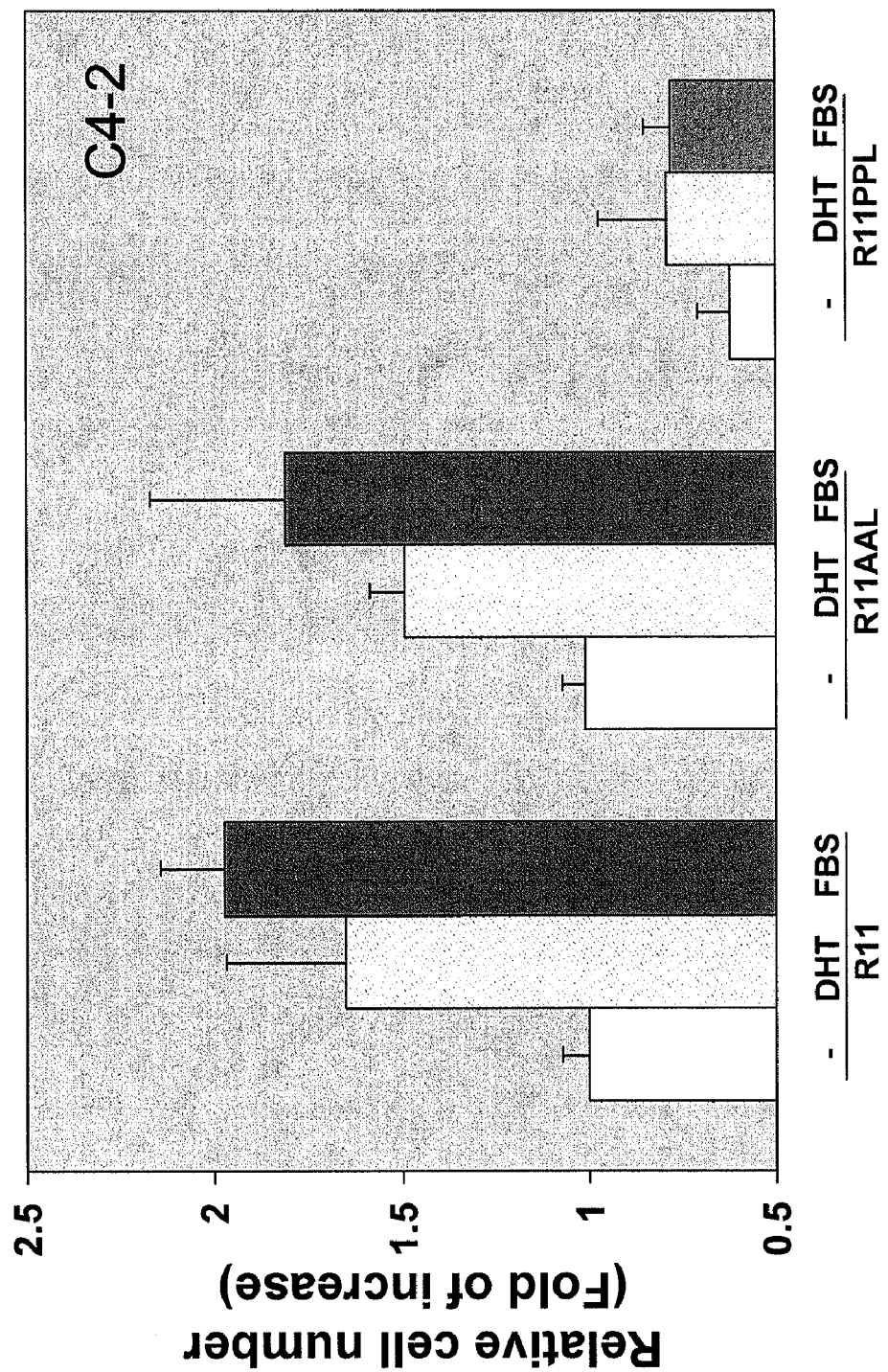

Characterization of biologic function of R11, R11AAL and R11PPL. In a previous publication (Zhou and Hsieh, 2001; Zhou et al., 2003), the inventors have delineated that the second PR domain (i.e., PPL) is able to sequester SH3-containing protein leading to the blockage of mitogen-elicited signal transduction, particularly, MAP kinase activation in these PCa cells. To examine whether R11PPL has a similar growth inhibitory effect as the native protein, both LNCaP and C4-2, DOC-2/DAB2-negative cell lines, were used. As shown in FIG. 3, both serum and DHT were potent mitogens for both cells. In the presence of R11PPL, either serum or DHT-induced cell proliferation of LNCaP and C4-2 cells was suppressed, in contrast, the control peptide R11AAL did not exhibit any effect. The data indicate that R11PPL can function as growth suppressor after uptake by PCa cells to mimic the function of its native protein.

Figure 4A:
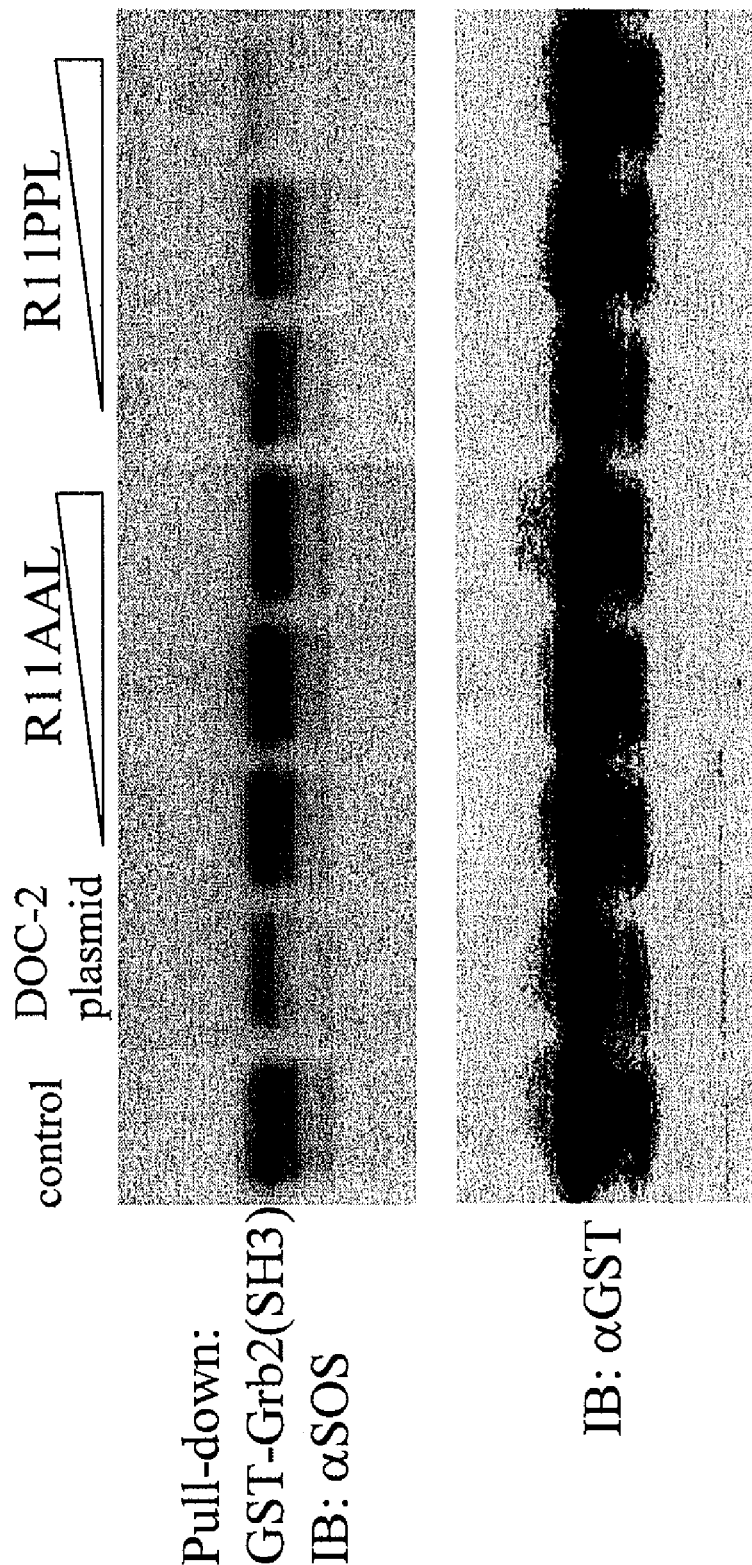
FIGS. 4A-B—Mechanism of action of R11PPL in PCa cells. To determine the function of R11PPL (SEQ ID NO:11) on interaction of Grb2 with SOS, the C4-2 cell lysates were collected after treated with EGF (FIG. 4A). The GST fusion protein with SH3 domain of Grb2 was used for the pull-down assay. The same amount of immobilized GST-Grb2 (SH3) protein (IB:αGST) was incubated with equal amount of cell lysate in addition of no peptide, the increasing amount of control R11AAL (SEQ ID NO:10) or R11PPL (SEQ ID NO:11) peptide as indicated. The binding of SOS was analyzed with Western Blot using SOS1 antibody. DOC-2/DAB2 expression plasmid transfection was used as a positive control. To examine the effect of R11PPL on MAP kinase activity (FIG. 4B), C4-2 cells were incubated with 5 μM R11PPL, R11AAL or R11 (SEQ ID NO:6) peptide 3 hours before adding EGF (10 ng/ml) (top panel) or 5% FBS (bottom panel). Cell lysates were subjected to western blot analysis probed with phosphorylated Erk1 and 2 antibody (αpErk1/2) or total Erk2 antibody (αErk2) used as a loading control. Each experiment has been repeated twice; this graph represents the typical result.

It is known that a underlying mechanism of DOC-2/BAD2 in inhibiting cell growth is to block the interaction of adaptor molecules such as Grb2 and SOS (Zhou and Hsieh, 2001). Thus, it is critical to confirm whether R11PPL has the similar function or not. As showed in FIG. 4A, the interaction between Grb2 and SOS was inhibited by the presence of native DOC-2/DAB2 protein. Consistently, a dose-dependent inhibitory effect was observed in R11PPL treatment but not in R11AAL treatment. These data indicate that R11PPL can mimic the function of its native DOC-2/DAB2 protein to sequester SH3-containing protein during signal transduction.

Figure 4B:
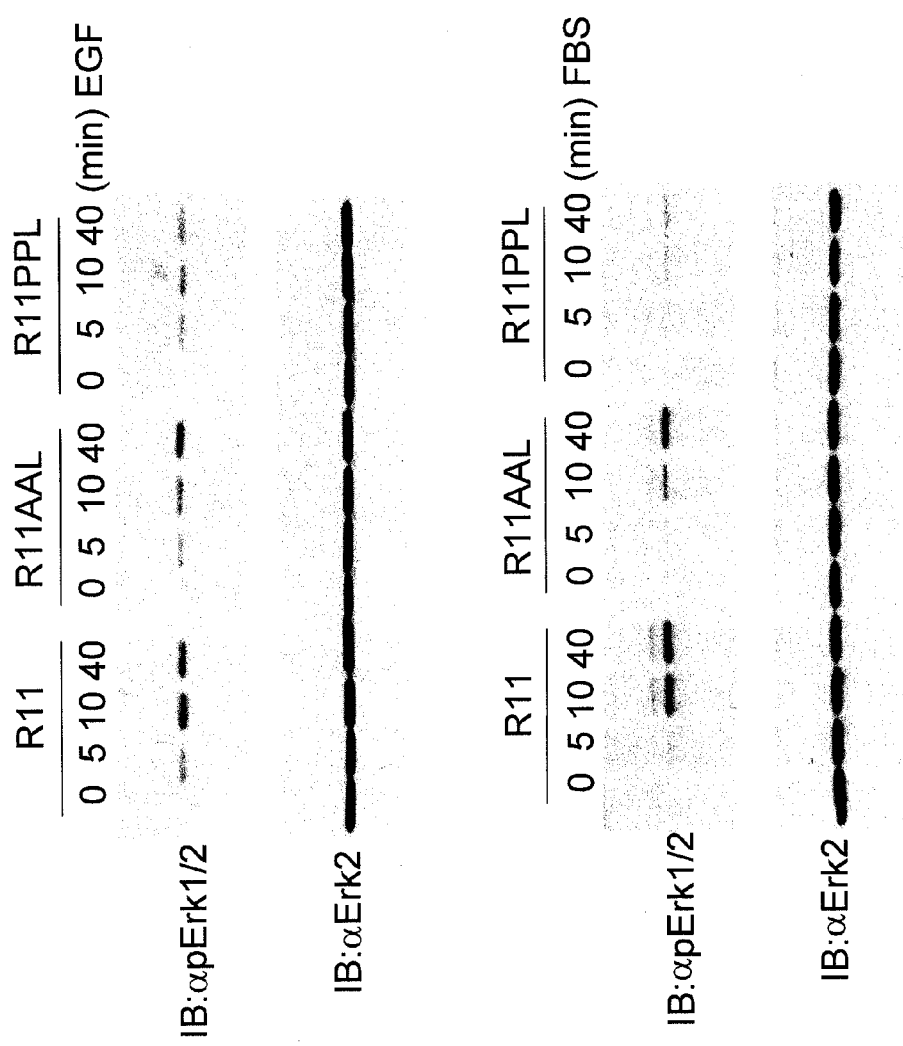
Figure 5:
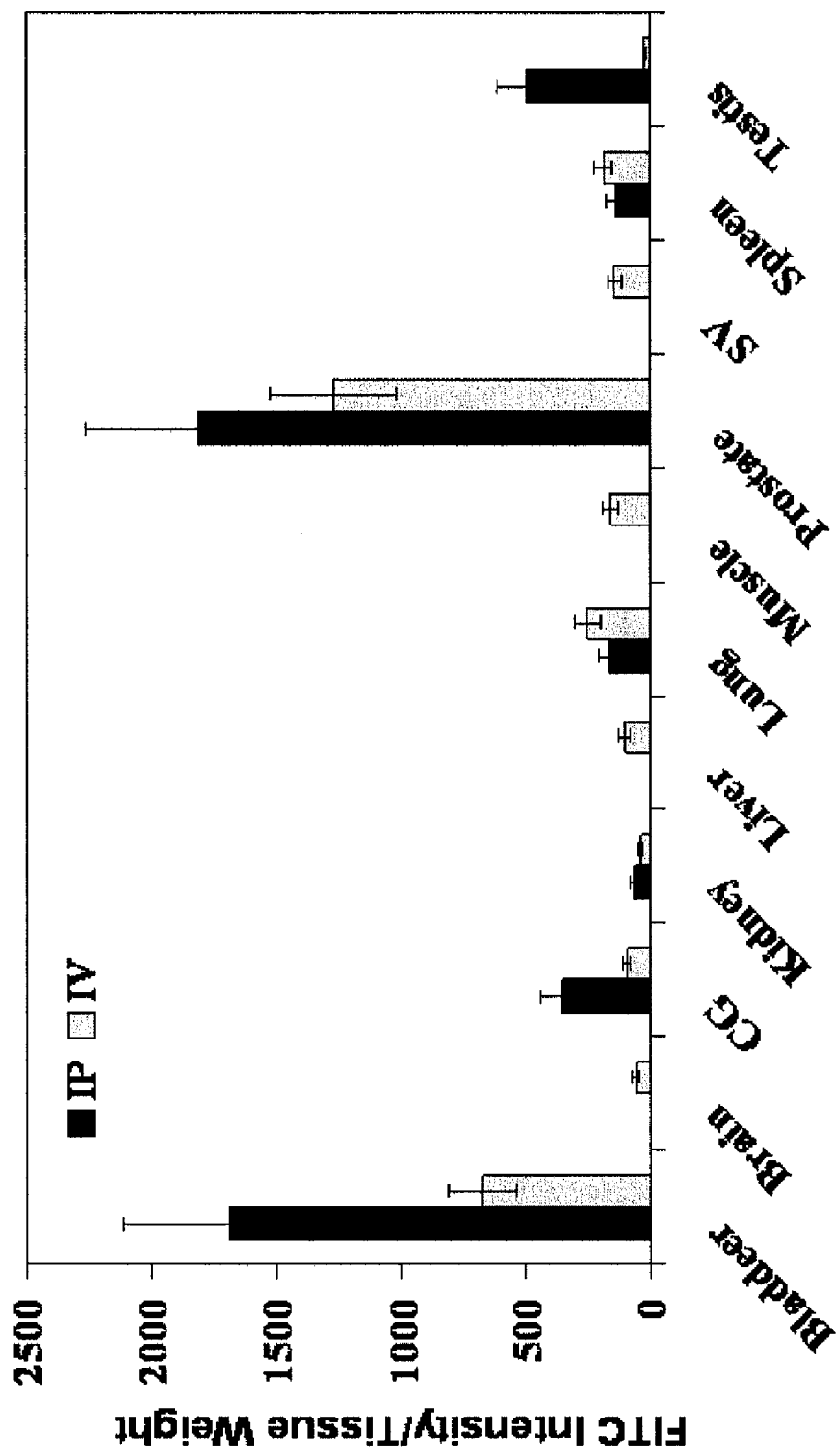
FIG. 5—FITC-tagged R11 in nude mice (n=3; 24 h post injection). The peptide was administered via intra-peritioneally (IP) or intravenously (IV).
Figure 6:
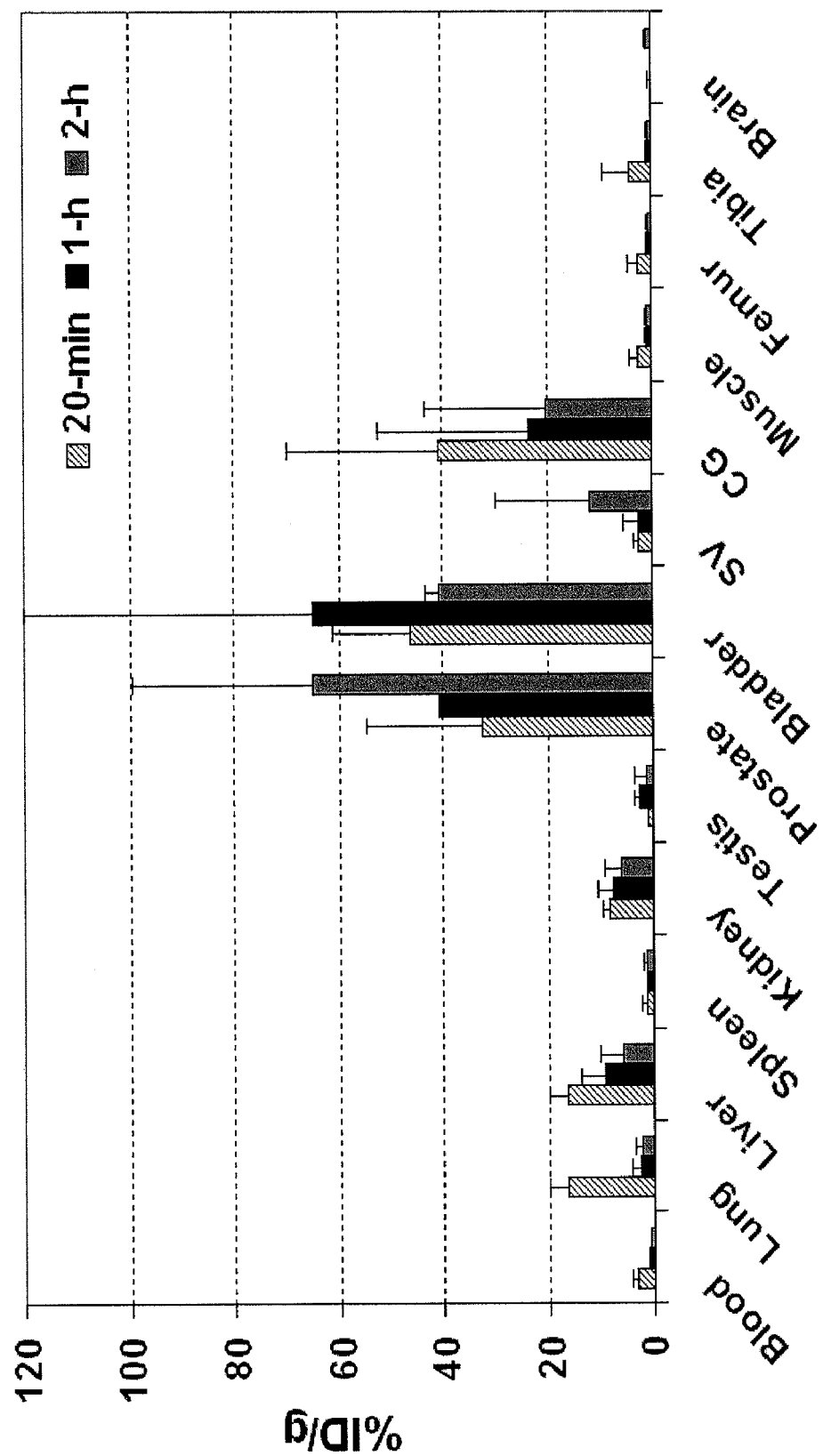
FIG. 6—Biodistribution data of $^{64}$Cu-DOTA-R11 in normal nude mice (n=4). Data are presented as % ID/g±s.d. SV: seminal vesicle; CG: coagulation gland.

To study the effect of R11PPL peptide on the down stream of growth signaling pathway, the inventors examined the time course of Erk2 activation in C4-2 cells induced by treatment of EGF (FIG. 4B, top panel). R11PPL treatment could suppress the EGF induced activation of Erk2 compared with R11 or R11AAL treatment. In addition, serum-induced activation of Erk2 was also studied in C4-2 cells (FIG. 4B, bottom panel). Similarly, serum-induced activation of Erk2 was suppressed in cells treated with R11PPL but not with R11AAL or R11. The data indicated that the treatment of R11PPL peptide could suppress EGF or serum-elicited MAP kinase phosphorylation, which is consistent with its native protein.

Discussion. Several evidences have supported DOC-2/DAB2 as a tumor suppressor from a variety of cancer types: 1) Down-regulation of DOC-2/DAB2 gene has been found in choriocarcinoma, ovarian, mammary, colon and PCa; 2) Re-expression of DOC2-/DAB2 in cancer cells result in suppression of cell, growth; 3) DOC-2/DAB2 can modulate several signal transduction pathways, including growth factor and androgen induced MAP kinase pathway. In PCa cells, loss of DOC-2/DAB2 expression is more frequently detected in PCa cell lines derived from metastatic site, which correlate with the increasing activity on MAP kinase in the high grade PCa (Gioeli et al., 1999; Price et al., 1999). Thus, DOC-2/DAB2 appears to be a potential therapeutic agent for metastatic PCa, the stage that become fatal disease.

In addition to many practical obstacles of delivering the whole protein into target cells, DOC-2/DAB2 is a large protein containing many other functional domains that are not fully characterized. From the structural-function analysis of DOC-2/DAB2, the inventors have shown that DOC-2/DAB2 can selectively bind to the SH3 domains-containing proteins, such as Grb2, c-Src, Fgr and Nck, but not to Crk or Spectrin (Zhou and Hsieh, 2001; Zhou et al., 2003; unpublished observation). The inventors further profiled the specific interaction of each PR domain with each SH3 domains-containing protein. For example, PPL can interact with Grb2 and c-Src but not Nck (Zhou and Hsieh, 2001; Zhou et al., 2003; unpublished observation). EGF-induced phosphorylation of Erk2 can be suppressed if DOC-2/DAB2 is re-expressed in PCa cells with the loss of DOC-2/DAB2 expression (Zhou and Hsieh, 2001; Zhou et al., 2003). The inventors defined the PR domain as the key functional motif of DOC-2/DAB2 in suppressing mitogen-elicited MAP kinas activation (Zhou and Hsieh, 2001; Zhou et al., 2003) often associated with high grade PCa (Gioeli et al., 1999; Price et al., 1999). In this study, the data clearly indicate that the R11PPL but not R11AAL exhibits a similar biological and biochemical activities of its native DOC-2/DAB2 protein in inhibiting cell growth induced by several mitogens (FIG. 3) and blocking Grb2 binding to SOS and the subsequent down stream MAP kinase activation (FIG. 4). Data from this study provide strong evidence that CPP-conjugated PPL can be a unique tool to dissect signal pathway and it can be further developed into a therapeutic agent.

Using small peptide derived from tumor suppressor now becomes an emerging technology for cancer therapy (Wadia and Dowdy, 2005) since small peptide can be engineered to mimic a selected function of tumor suppressors such as p53 (Selivanova et al., 1997; Harbour et al., 2002) and VHL (Datta et al., 2001). In addition, small peptide can avoid undesired function from different part of selected protein (Noguchi et al., 2004) and can potentially evade immune system because it is less immunogenic.

PR domains have been used as a tool to analyze the signal transduction mediated by SH3 domain-containing proteins (Vidal et al., 2001). As a ligand with respect to SH3 domain, two classes of PR sequence have been proposed based on alanine-scanning mutagenesis, phage display, combination of chemistry and high-resolution structure determination. The consensus sequence for class I or class II ligand is defined as RxxPxΦP or PxΦPxR (where x is any amino acid, and Φ is hydrophobic amino acid) respectively (Mayer, 2001). Based on the location of arginine in each class and its binding to the acidic cluster of SH3 domain, it is believed that class I ligand binds SH3 domain in the opposite orientation as class II ligand does. It appears that the PPL sequence (RQPPLVPSR; SEQ ID NO:7) derived from DOC-2/DAB2 has a unique composition because it contains an overlapping consensus sequence from both classes. Although, the functional significance of this unique structure is not completely understood, further study of this structure of PPL peptide should provide better understanding the interaction mode between PR and SH3 domains. For example, it is still unclear that how specific pairwise interaction between PR and SH3 domain can be achieved during each specific signaling transduction, since the binding affinity between RP and SH3 domain is generally low (Ki of $10^{-6}$-$10^{-4}$ M). It is possible that PPL can engage simultaneously in multiple interactions with several SH3 domain-containing proteins and such dynamic equilibrium is necessary to elicit a meaningful biological output (Mayer, 2001). Nevertheless, PPL should be a good model to test this hypothesis since PPL can bind to more SH3 domains from different proteins than two other PR domains from DOC-2/DAB2 (Zhou and Hsieh, 2001; Zhou et al., 2003).

Polyarginine has been found as a cell permeable peptide based on the structural comparison with TAT and other cell permeable peptides (Futaki et al., 2001). It has been found that poly-arginine could be more efficiently taken up into cells (Wender et al., 2000). However, the uptake efficiency of poly-arginine is highly cell type dependent (Mai et al., 2002), indicating that it's important to compare several CPPs for the best candidate in any given cell type. By screening five different CPPs in a variety of PCa cell lines, the data indicated that R11 is the best delivery system in all PCa cells tested, including an immortalized cell line PZ-HPV7 cells. The uptake can be detected within 5 minutes in PCa cells shortly exposed to CPP (FIG. 1B), which is consistent with previous finding (Vives et al., 1997). It has been reported that the majority of poly-arginine peptides remain inside in cells with a little leak out and they appears to be intact (Futaki et al., 2001). From the in vitro half-life study (FIG. 1C), a longer half-life in PCa cells was observed compared with other reports (Futaki et al., 2001; Fischer et al., 2004), suggesting that R11 may be more stable in PCa cells than other cell types.

Taken together, the inventors have documented an efficient CPP delivery system for PCa cells and also demonstrated that a small PR sequence mimicking the native DOC-2/DAB2 protein can function as a growth inhibitor in PCa cells elicited by serum and androgen. The outcome of this study provides a unique tool for analyzing signal transduction pathway in PCa, very likely, this system can be used as a therapeutic agent for PCa.

Example 3

PCA Cell Internalization of the CPPS as Determined by Fluorescence Microscopy

To determine the uptake efficiency of each CPP, different concentrations (0.1, 1, 5 µM) of FITC-tagged peptides were incubated with cells for 30 minutes (or different time for the time course study) then cells were washed twice with PBS and trypsinized. After washing with PBS twice, the total cell number was determined and cells were lysed in Tris Buffer (50 mM Tris-HCl, pH 7.5, 150 mM NaCl, 5 mM EDTA, 1% Triton X100). The fluorescence intensity was examined by fluorometer (excitation 490-500 nm; emission 515-525 nm). To determine the cellular localization of CPPs, after 30-minute incubation, cells were fixed with 4% paraformaldehyde in PBS plus DAPI (1 µg/ml) counterstaining (Sigma, St. Louis, Mo.) and cells were examined under fluorescence microscope. As shown in FIG. 1, a dose-dependent CPP uptake by four different PCa cells (LNCaP, C4-2, LAPC4 and PC3) was observed. Among the five CPPs, R11 exhibited the highest uptake (at least 6-fold higher) in all four PCa cell lines. In addition, using fluorescence-activated cell sorting technique, the inventors were able to confirm that R11 at the lowest concentration could give rise to 100% cells with positive staining compared with the other four CPPs. The inventors further examined the half-life of R11 in each cell line by pulsing cells with FITC-labeled R11 (5 µM) for 30 minutes then removing any free R11. Using linear regression analysis, the half-life of R11 in LNCaP, C4-2, LAPC4 and PC3 is 23.4, 24.1, 22.8 and 24.0 h, respectively. These data showed that R11 is a rapid delivery vehicle for a variety of PCa cells with its in vitro half-life about 23-24 h, indicating its high stability in vitro (or the long intracellular retention of FITC).

Example 4

Prostate and Bladder Tissue-Specificity Exhibited by FITC-Tagged

Although the cell internalization mechanism of CPPs is under debate, they were not supposed to have cell specificity (Ziegler et al., 2005; Xie et al., 2005; Wadia and Dowdy, 2005; Turner et al., 2005; Torchilin, 2005; Saar et al., 2005; Futaki et al., 2005; El-Andaloussi et al., 2005; Deshayes et al., 2005). Interestingly, during the in vivo evaluation of tissue distribution of FITC-tagged R11 in nude mice, the inventors were surprised to find that the R11 peptide exhibited highly preferential uptake in prostate and bladder tissues, while its accumulation in other organs (e.g., liver, lungs, muscle, and kidneys) was much lower (FIG. 2). This observation clearly demonstrates that the CPP, R11, is of tissue specificity in addition to its cell membrane translocation feature.

Example 5

Biodistribution and Pet Imaging of $^{64}$Cu-Labeled DOTA-R11 in Tumor-Bearing Mice In order to explore the application of R11 for the detection of PCa extraprostatic spread via PET, the inventors conjugated this peptide with a bifunctional chelator, DOTA (1,4,7, 10-Tetraazacyclododecane-1,4,7,10-tetraacetic acid), so that R11 could be radiolabeled with $^{64}$Cu. The conjugation was carried out by automated peptide synthesizer and the conjugate, DOTA-G-RRRRRRRRRRR (SEQ ID NO:6) (DOTA-R11), was purified by reverse phase HPLC and characterized by mass spectrometry. DOTA-R11 was then radiolabeled with $^{64}$Cu (MDS Nordion, Canada) in 0.1 M NH$_4$OAc buffer (pH 7.5) at high radiochemical yields (>80%) after 2-h incubation at RT. The radiolabeled peptide was purified via a C-18 cartridge (Millipore) to have >95% radiochemical purity as determined by radio-TLC and HPLC prior to the biodistribution and PET imaging studies. The highest specific activity of $^{64}$Cu-DOTA-R11 achieved was ~650 µCi/nmol.

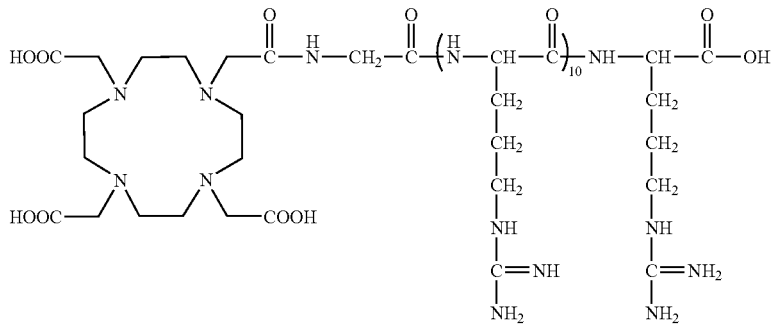

Example 6

Biodistribution of $^{64}$Cu-DOTA-R11 in Normal Nude Mice

The injected dose of $^{64}$Cu-DOTA-R11 in the biodistribution studies was in range of 5-10 µCi. The animals were sacrificed at specific time points (n=4 at each time point). Organs of interest were removed, weighed, and counted.

Standards were prepared and counted along with the samples to calculate the percent injected dose per gram tissue (% ID/g). It is apparent that $^{64}$Cu-DOTA-R11 has a strong tendency to accumulate in prostate and bladder (FIG. 3), despite the large standard deviations likely representing animal individual difference. Further, this peptide exhibited remarkably low uptake in other organs (e.g., blood, lungs, liver, spleen, kidneys, and muscle). This confirms the observation of using FITC tagged R11 in the same animal model and demonstrates that R11 could be a novel biomarker of PET imaging probes development.

The pharmacokinetics of the $^{64}$Cu-labeled peptide was also evaluated by using a two-compartment model. Its half-life of $^{64}$Cu-DOTA-R11 in the blood (the primary compartment) was about 10.7 min (ln 2/α); and the elimination half life from other organs (the secondary compartment) was 17.2 h (ln 2/β).

Example 7

Pet Imaging of $^{64}$Cu-DOTA-R11 in PC-3 Tumor-Bearing Mice

The tumor-bearing animal model was established by injecting into the left flank of each nude mouse subcutaneously with PC-3 cell suspension (2×10$^6$ cells in 100 μL of T medium with 5% FBS). The tumors were allowed to grow for 10 days prior to PET imaging. Two mice were imaged with $^{64}$Cu-DOTA-R11 by a small animal PET system. The injected dose was ~1.5 mCi in 100 μL. The image requisition time was about 60 min. As in FIG. 4, the tumor in the left flank was clearly revealed with $^{64}$Cu-DOTA-R11. Post-PET biodistribution was performed to validate the imaging result. The tumor revealed in FIG. 4 was only 4.7 mg; the tumor in 2$^{nd}$ animal was much bigger (17.8 mg) but the uptake ratio of tumor/muscle was nearly identical in both animals (1$^{st}$ mouse: 8.56; 2$^{nd}$ mouse: 8.74). Coronal images (anterior) of $^{64}$Cu-DOTA-R11 in a PC-3 tumor bearing mouse were obtained. The image was acquired post 1-h injection. The tumor revealed was in the left flank (w/o matrigel).

Example 8

Orthotopic and Metastic Tumor Models for Bladder Cancer

Figure 7A:
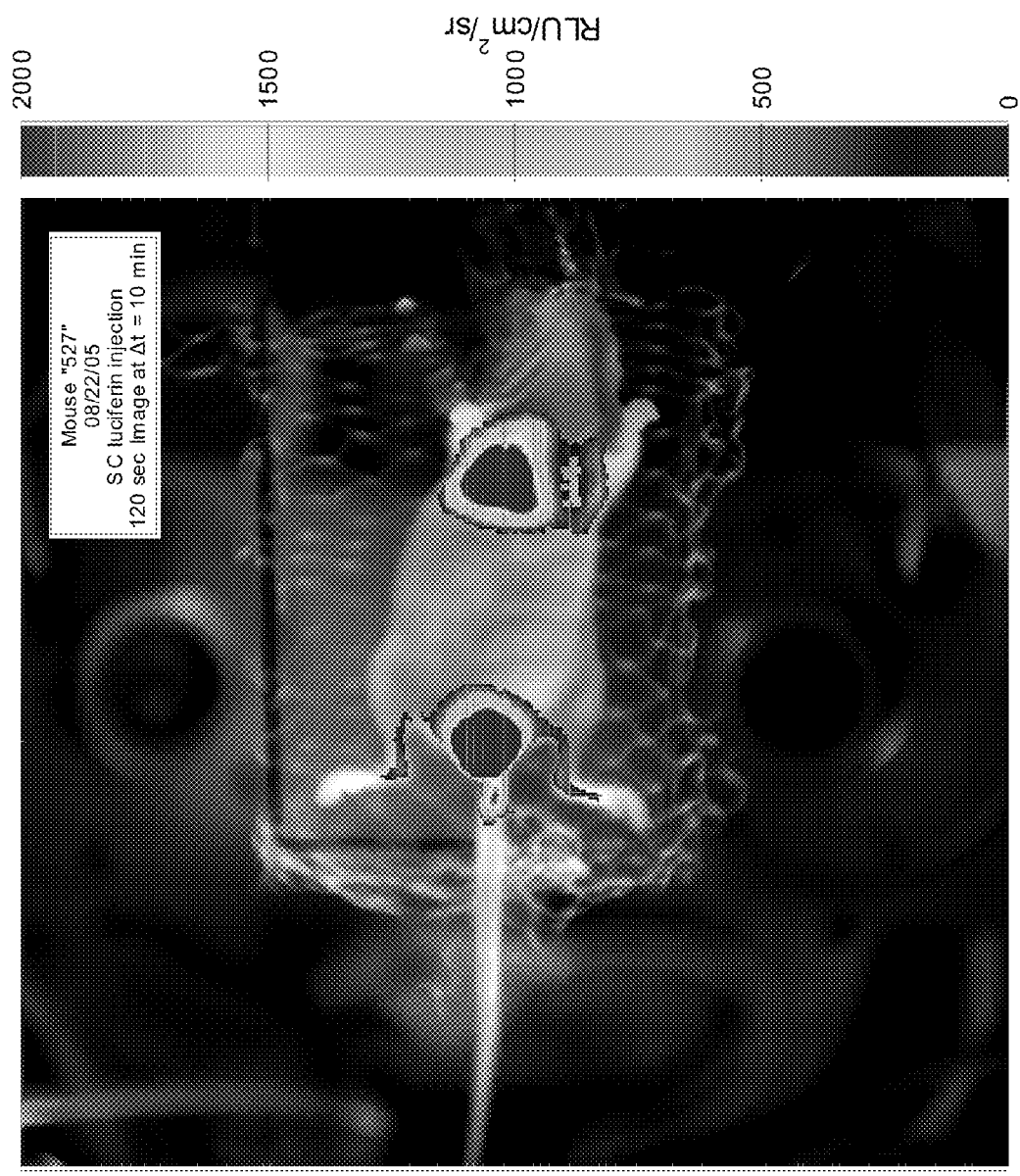
FIGS. 7A-B—Development of orthotopic model (FIG. 7A) and metastatic model (FIG. 7B) using human bladder cancer cells. T24 cells were instilled into bladder using Angiocath®. Two weeks after instillation, BLI imaging was carried out weekly.
Figure 7A:
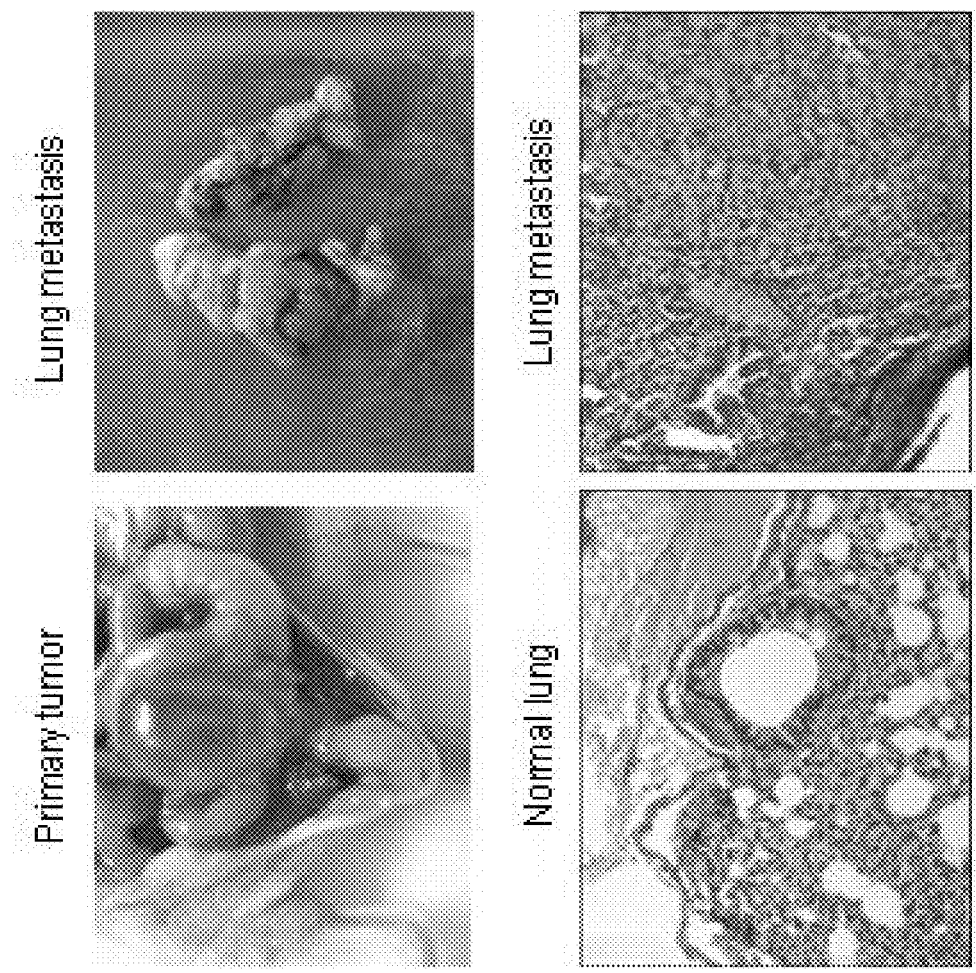
Figure 7B:
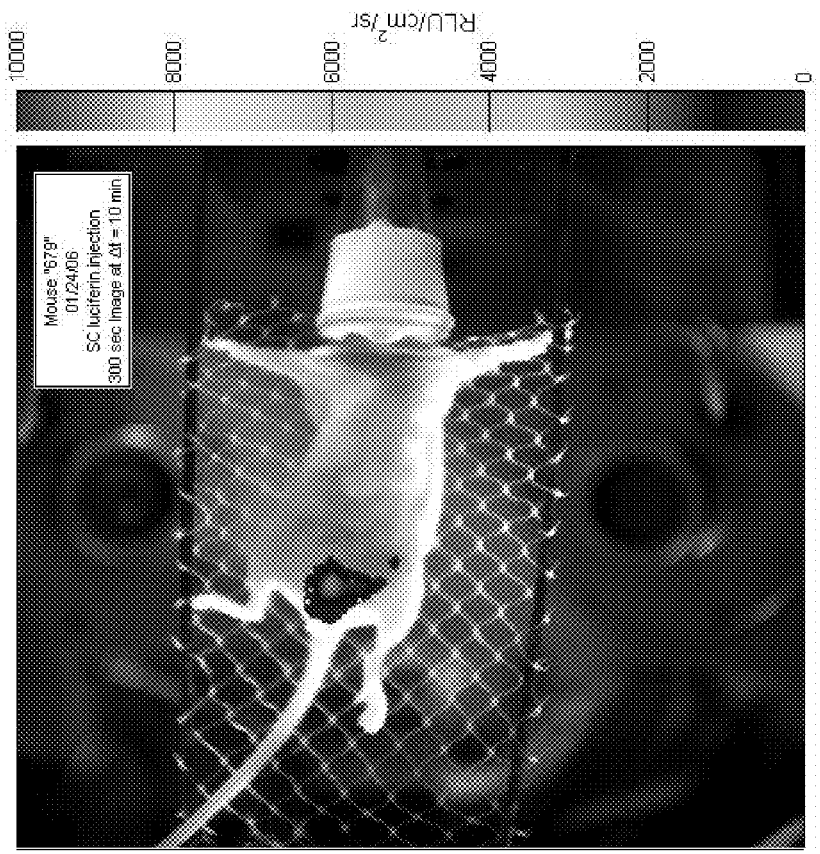
Figure 7B:
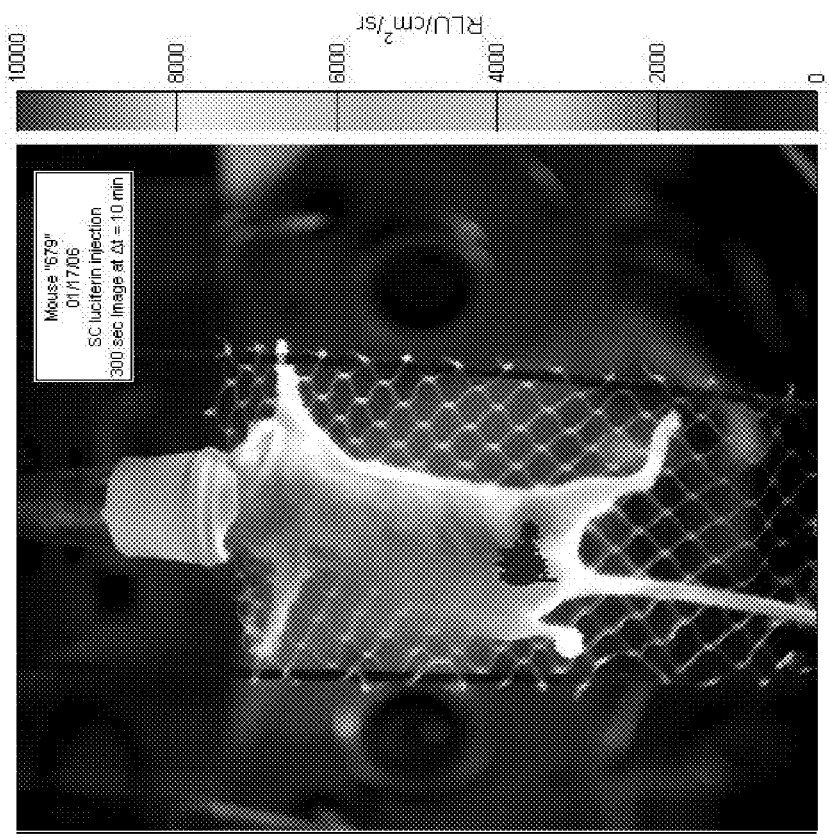
Figure 7B:
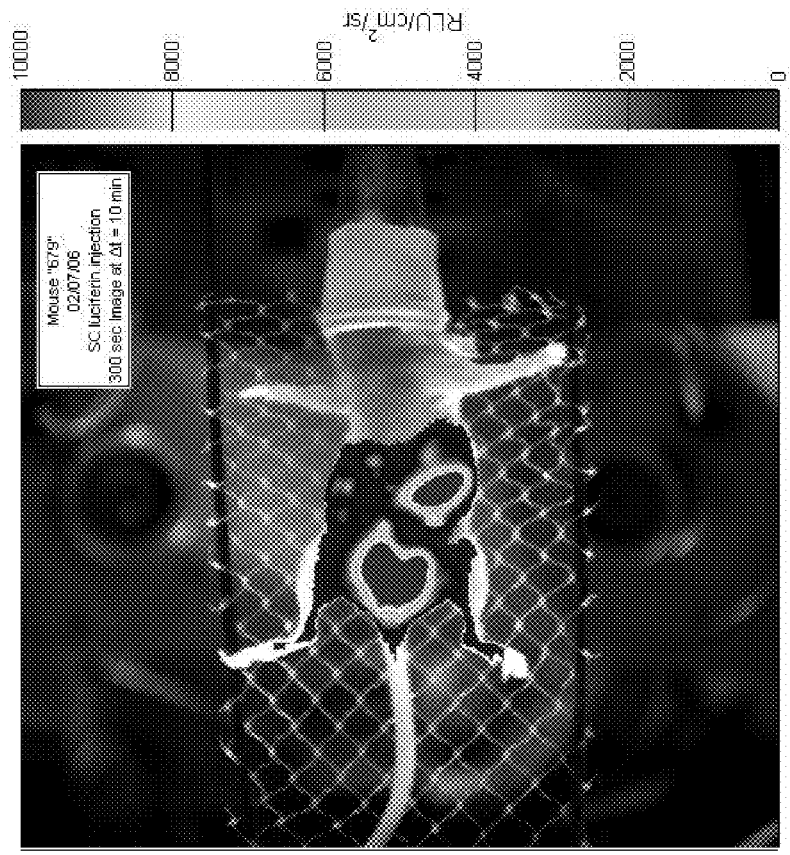
Figure 7B:
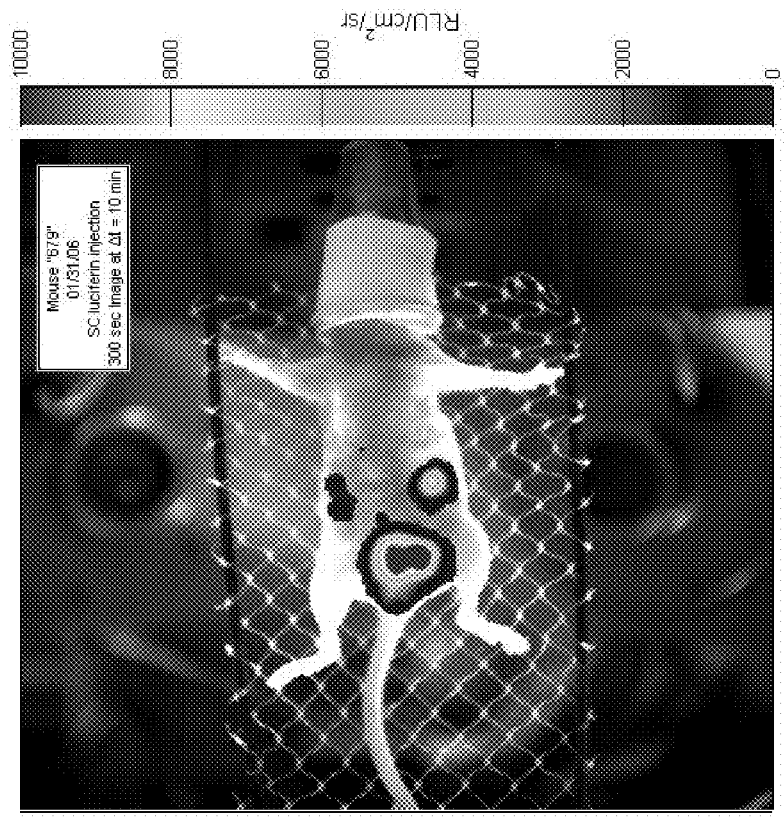
Figure 7B:
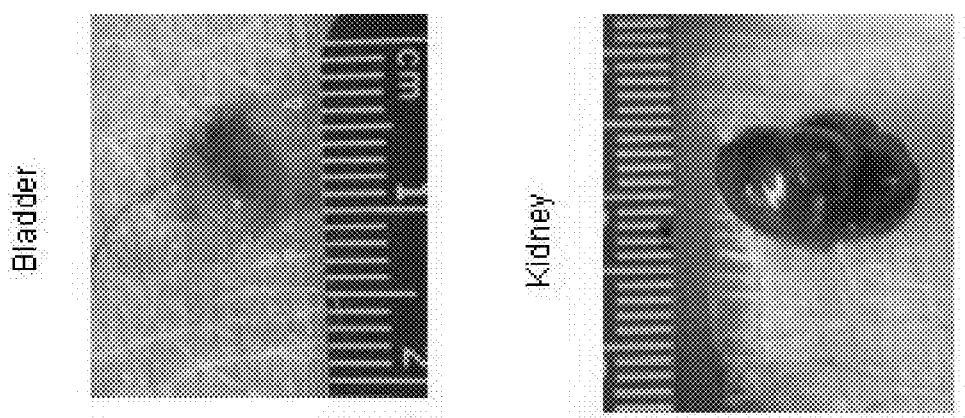

On the other hand, the field of bioluminescence imaging (BLI) has been studied in preclinical oncology research. Nude mice were instilled with luciferase-expressing bladder cancer cells orthotopically (i.e., inside of bladder wall); this model mimics the superficial tumor most frequently diagnosed in Bladder cancer patients. Luciferin (the substrate of luciferase) was then injected, and imaging was performed using an Intensified Charge Coupled Device (ICCD). This device detects the photons produced by the interaction between luciferin and luciferase, which are emitted through the skin. BLI detected a tumor lesion in the bladder 4 to 5 weeks after instillation (FIG. 7A), before any palpable tumor could be identified. After 7 to 8 weeks, distinct light emitting areas were detected in local lymph node or distant visceral organ such as lung. Subsequently, organs with potential metastatic bladder cancer from the mice were harvested for pathologic examination and a small part of these tissues was further dissociated into cell suspension and plated in tissue culture plate under G418 selection. Once tumor cells were established in vitro, these sublines were instilled into bladder again; these cells appeared to be highly tumorigenic (BLI signal was detected in the bladder 2 weeks after instillation) and metastatic (BLI signal was detected in the bladder 4 weeks after instillation) (FIG. 7B). Obviously, BLI is a critical non-invasive detection tool for allowing us to monitor spatio-temporal distribution of tumor cells and greatly reduce the number of animals and surgical procedures to probe tumor metastasis.

Majority of newly diagnosed bladder cancer cases are low grade and noninvasive. For local invasive disease confined to the pelvis, the standard treatment is radical cystectomy or pelvic lymphadenectomy. The cure rate of organ-confined bladder cancer is more than 70%. However, there is a high-grade cancer, which is characterized by rapid progression with local invasion, extension to the adjacent organs, and development of regional and distant metastases. Also, the presence of lymph node metastases increases the chance of recurrence and distant disease, and this group of patients has only 20 to 25% of 5-year survival rate. Preoperative diagnosis of local extension would help to select appropriate bladder-sparing surgery, nerve- or vaginal-sparing operations, or pelvic exenteration. Historically, the staging of bladder cancer with various imaging modalities has been limited. CT scanning can detect only gross tumor extension beyond the bladder wall with an accuracy of 64 to 92%. The accuracy of CT in detecting lymph node metastases ranges from 70 to 90% with false-negative rates as high as 40%. Similarly, MRI has been disappointing for staging with accuracies ranging from 60-75%. The major limitation of these imaging modalities is the dependence on nodal size and anatomical changes to make a diagnosis of cancer. Given the ability of FDG-PET to detect differential metabolic activity, investigators have begun exploring the use of FDG-PET to stage bladder cancer (Schoder and Larson, 2004; Jana and Blaufox, 2006).

PET is a metabolic imaging tool that exploits the higher metabolic rate of cancer cells. The most commonly used clinical tracer is $^{18}$F-fluorodeoxyglucose ($^{18}$F-FDG). The radiotracer is given intravenously and is usually taken up greater by cancer cells because of transporters that are more highly expressed in addition to higher metabolic rate. This modality has met with little success in bladder cancer imaging because the tracer is excreted in the urine, obscuring the view of tumor. Despite this initial shortcoming, PET may potentially be better than CT or MRI for lymph node staging of bladder cancer. It has been reported to have a sensitivity of 67%, a specificity of 86%, and an accuracy of 80% when used in this setting (Schoder and Larson, 2004; Jana and Blaufox, 2006). On the other hand, investigators have attempted to improve the sensitivity of PET by using tracers that are not excreted in the urine. Ahlstrom and coworkers found $_{11}$C-methionine is superior to FDG; however, tumor was identified with a sensitivity of only 78% (18/23) with methionine PET (Ahlstrom et al., 1996). They also reported that tracer uptake was proportional to tumor stage. Moreover, it appears that PET is also useful for the detection of cancer in the pelvis, distinguishing fibrosis from necrosis, and the identification of distant metastasis (Ahlstrom et al., 1996). Further studies using new tracers with a higher sensitivity and specificity are needed in order to allow PET in early detection of metastatic bladder cancer and regional staging.

Example 9

Cell Internalization of CPP'S as Determined by Fluorescence Microscopy

Figure 8:
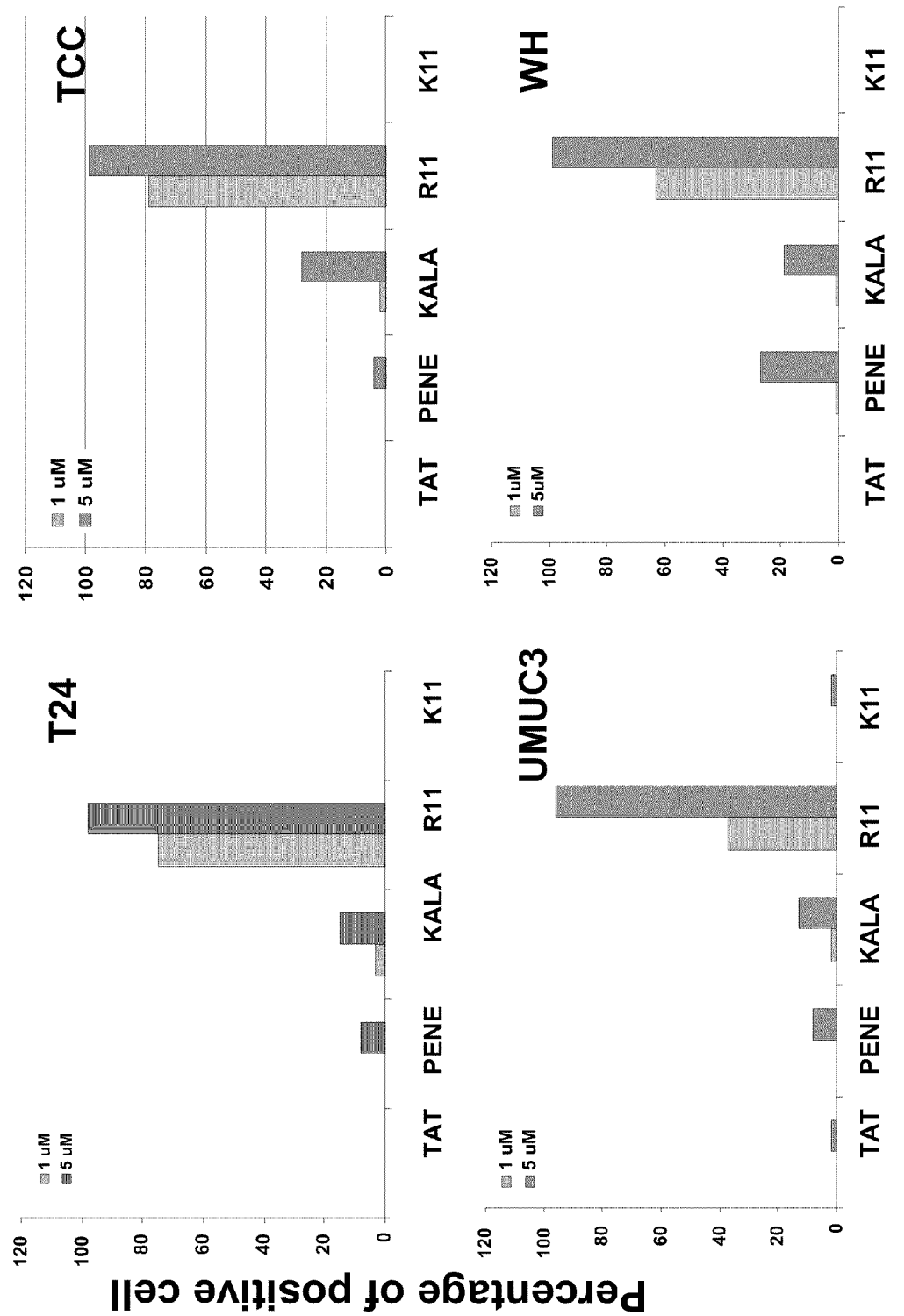
FIG. 8—The uptake of CPPs by bladder cancer cell lines. Different concentrations of each CPP were incubated with cells for 30 min prior to cell harvesting. After gating the fluorescence intensity of no treatment cell as a basal level, the percentage of positive cell was determined from 10,000 cells based on the intensity over the basal level.

Knowing the rapid uptake property of CPP in vitro, CPP becomes a unique delivery vector system compared with current available transfection reagent. However, the cellular uptake of CPP is highly cell type dependent. Thus, the inventors decided to screen a variety of CPPs for optimal intracellular delivery into bladder cancer cells. Five peptides representing different class of CPP were chosen: TAT (GRKKRRQRRR (SEQ ID NO:7)), PENE (G-RQIKIW-FQNRRMKWKK (SEQ ID NO:8)), KALA (G-KLALKLA-LKALKAALKLA (SEQ ID NO:9)), homopolymers of L-arginine R11 (G-R11), and homopolymers of L-lysine K11 (G-$K_{11}$) by automated peptide synthesis using the standard solid phase chemistry. The CPPs were purified by reverse phase HPLC and analyzed by mass spectrometry. The amount of peptide was determined by mass spectrometry and normalized by fluorescence intensity. To determine the uptake efficiency of each CPP, different concentrations (0.1, 1, 5 µM) of FITC-tagged peptides were incubated with cells for 30 minutes (or different times for the time course study) then cells were washed twice with PBS and trypsinized. After washing with PBS twice, the total cell number was determined and cells were lysed in Tris Buffer (50 mM Tris-HCl, pH 7.5, 150 mM NaCl, 5 mM EDTA, 1% Triton X100). The number of positive cell was determined by fluorescence-activated cell sorting technique (excitation 490-500 nm; emission 515-525 nm). A dose-dependent CPP uptake by four different bladder cancer cells (T24, TCC, UMUC3 and WH) was observed. Among the five CPPs, R11 exhibited the highest uptake (at least 6-fold higher) in these four bladder cancer cell lines. In addition, R11 at 5 µM could give rise to almost 100% cells with uptake compared with the other four CPPs (FIG. 8), indicating that R11 is an efficient delivery vehicle for a variety of bladder cancer cells.

Example 10

Figure 9A:
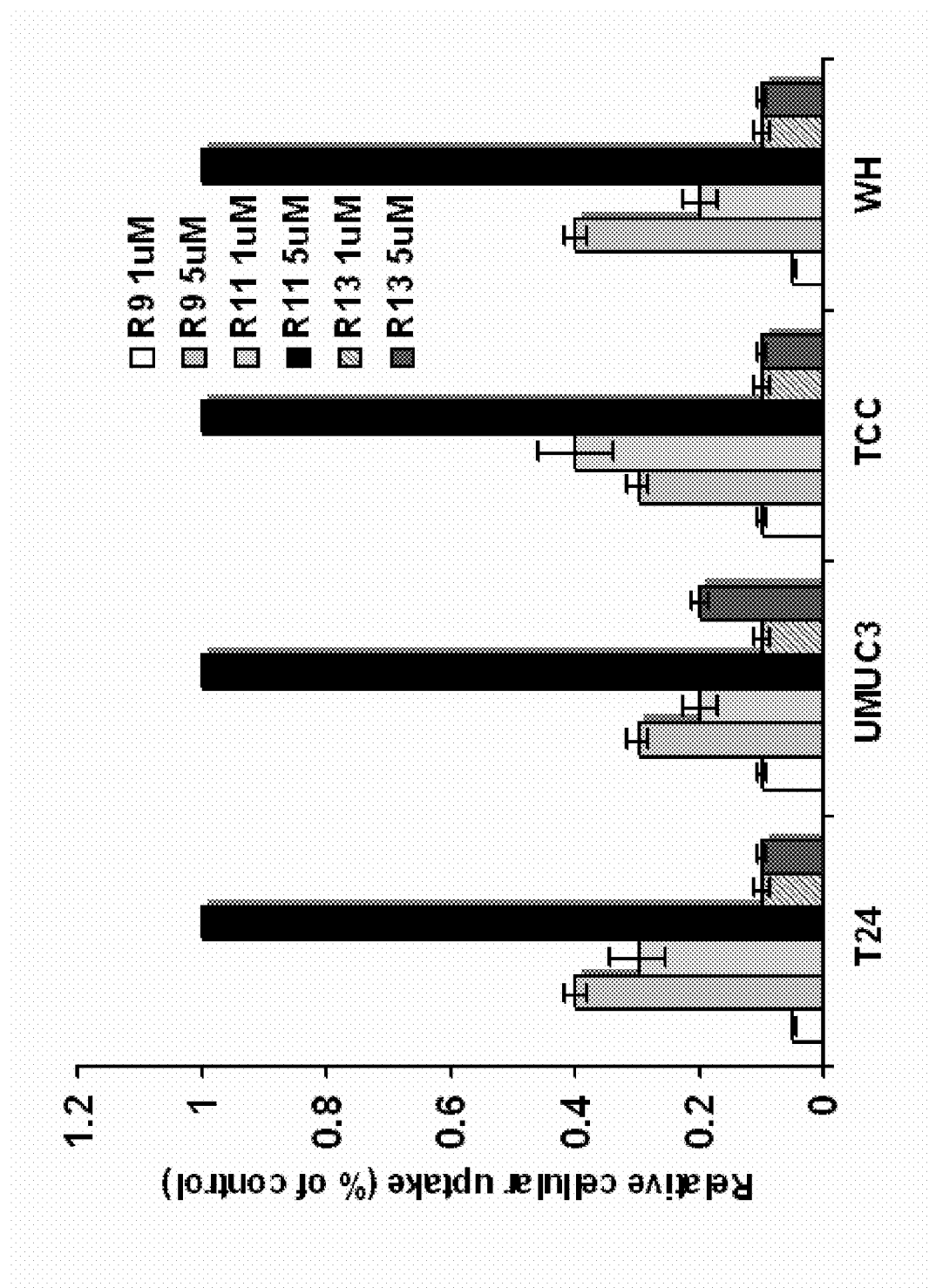
FIGS. 9A-C—Comparison of delivery efficiency between different length of polyarginines.
Figure 9B:
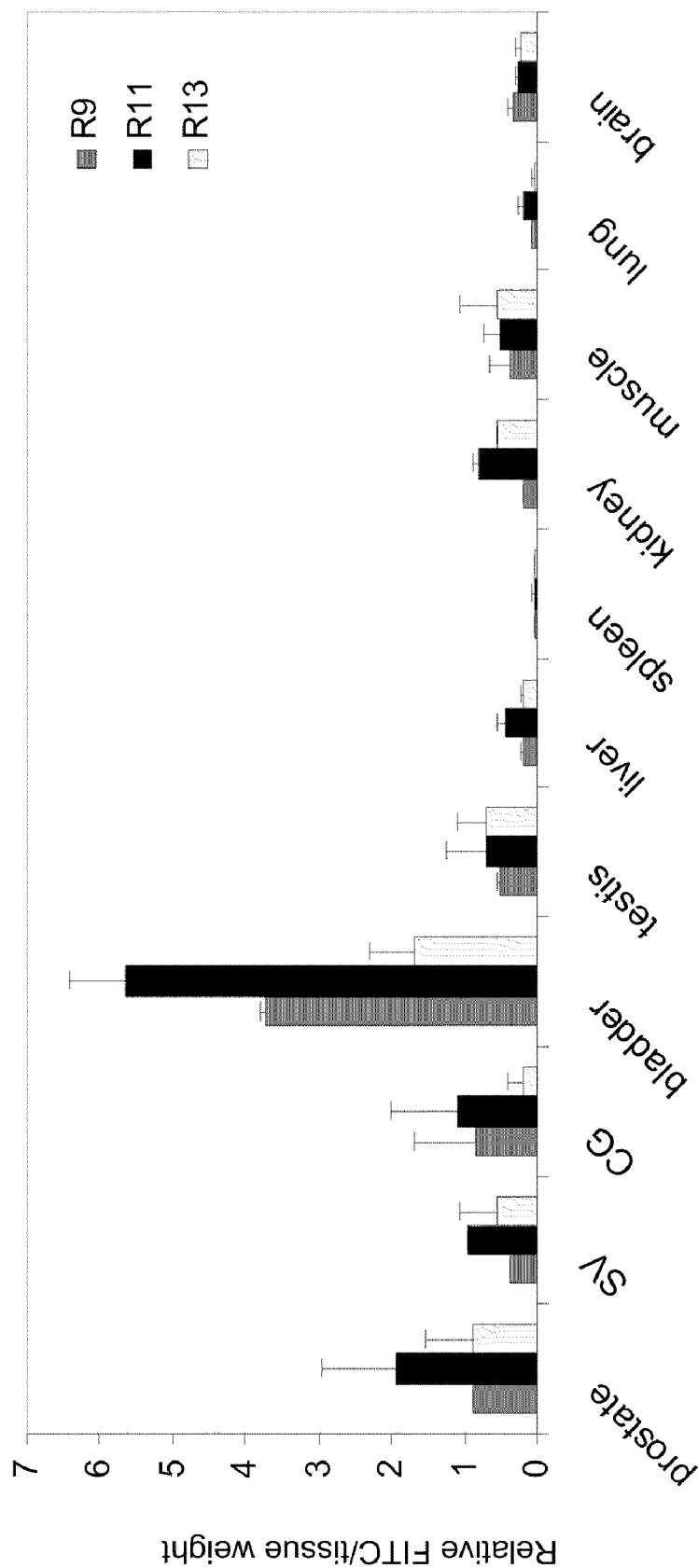
Figure 9C:
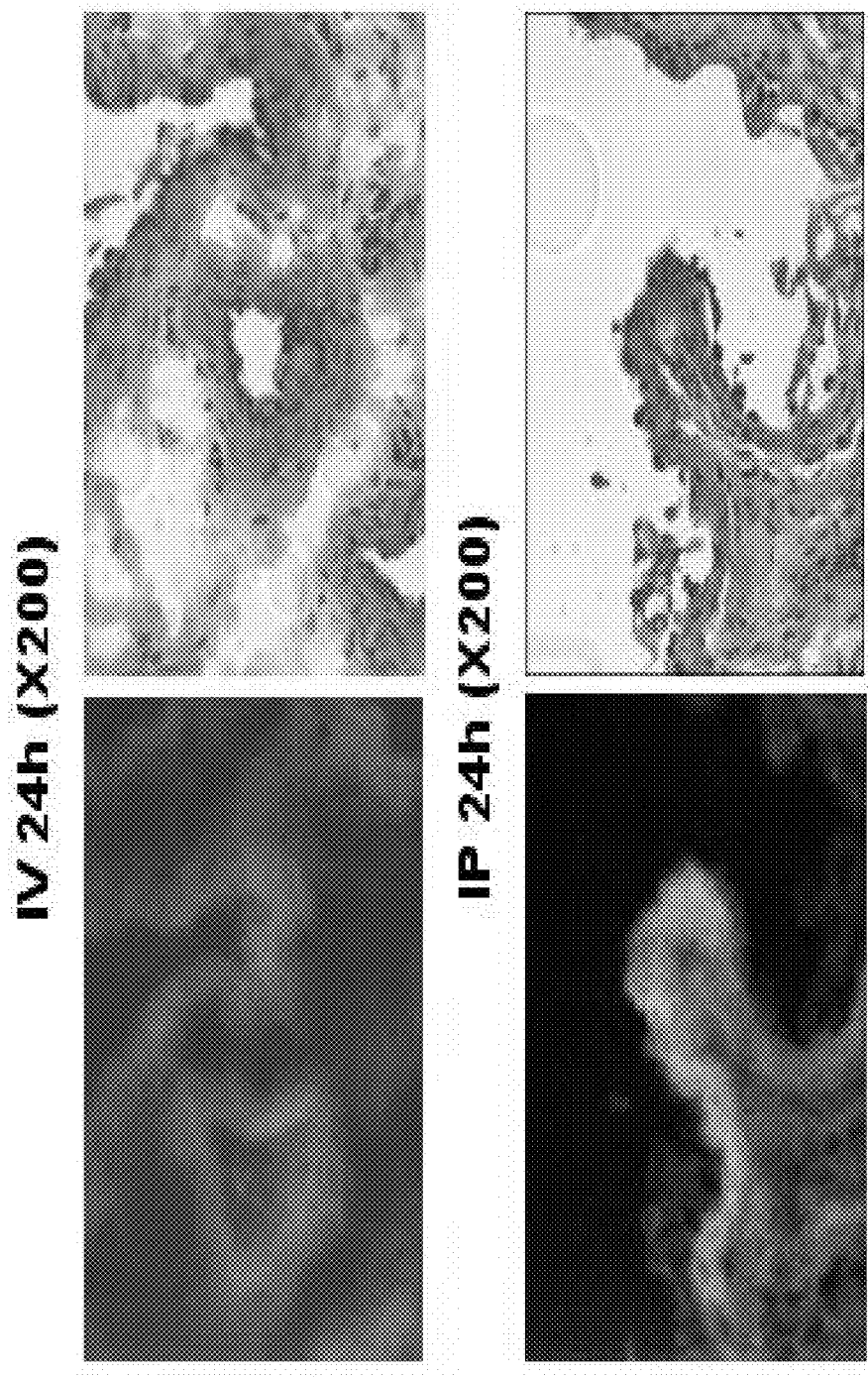

High Efficiency R11 Uptake Compared with R9 or R13 in Bladder Cancer Cells and Tissue Although the cellular uptake mechanism of CPPs is not completely understood, they were not supposed to have cell specificity. Also, the efficiency of CPPs delivery varies among different species and length. For example, Mai et al. (2002) has reported that the 8-mer and 10-mer of polylysine have higher cell permeable efficiency for a broad range of cell types than polyarginine does. However, the inventors observed that polyarginine is more efficiency than polylysine in bladder cancer cells (FIG. 9A). In order to further determine whether R11 is the best polyarginine for bladder cancer cells, the inventors examined the uptake efficiency using different lengths of polyarginine. Data from in vitro uptake (FIG. 9A) clearly indicated that R11 has the highest efficiency than R9 and R13. Similarly, from the in vivo evaluation of tissue distribution of these three polyarginines in nude mice, they were able to confirm that the R11 is better than R9 or R13 and it exhibits a organ-specific uptake in bladder and prostate tissues at 24 h after either intravenous (FIG. 9B), while its accumulation in other organs was much lower (FIG. 9B). To rule out the possible artifact due to urine excretion, histologic examination was performed to show the presence of R11 in both transitional and stromal cell compartments of bladder (FIG. 9C).

Example 11

Possible Mechanism of R11 Uptake by Bladder Cancer Cells

In order to define R11 as a bladder-specific molecular probe, it is critical to unveil the mechanism of R11 uptake.

Figure 10A:
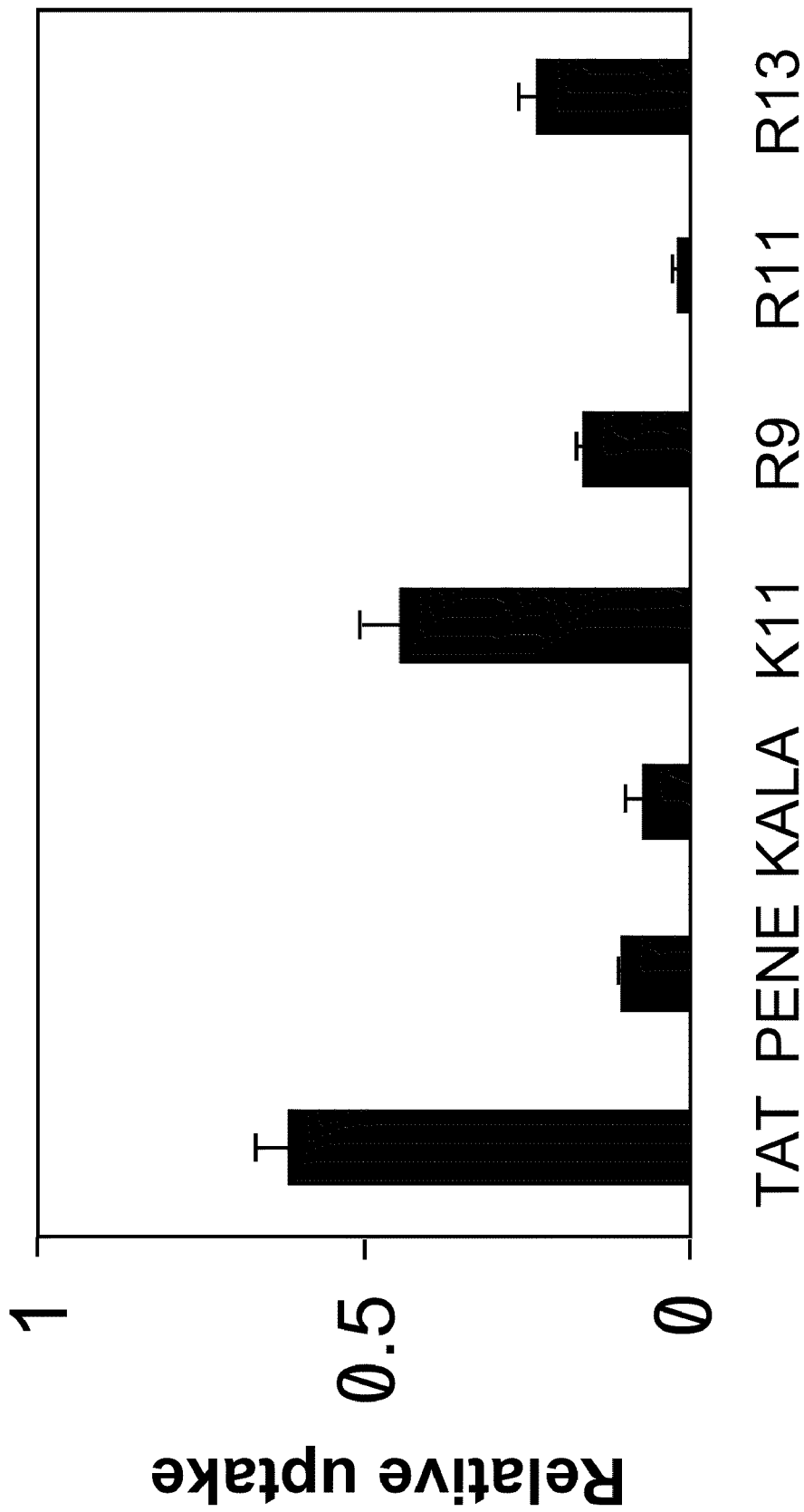
FIGS. 10A-C—Determination of primary interaction molecule for R11 uptake in several bladder cancer cells. Human bladder cancer cells were pre-treated with various inhibitors (FIG. 10A: EIPA.
Figure 10B:
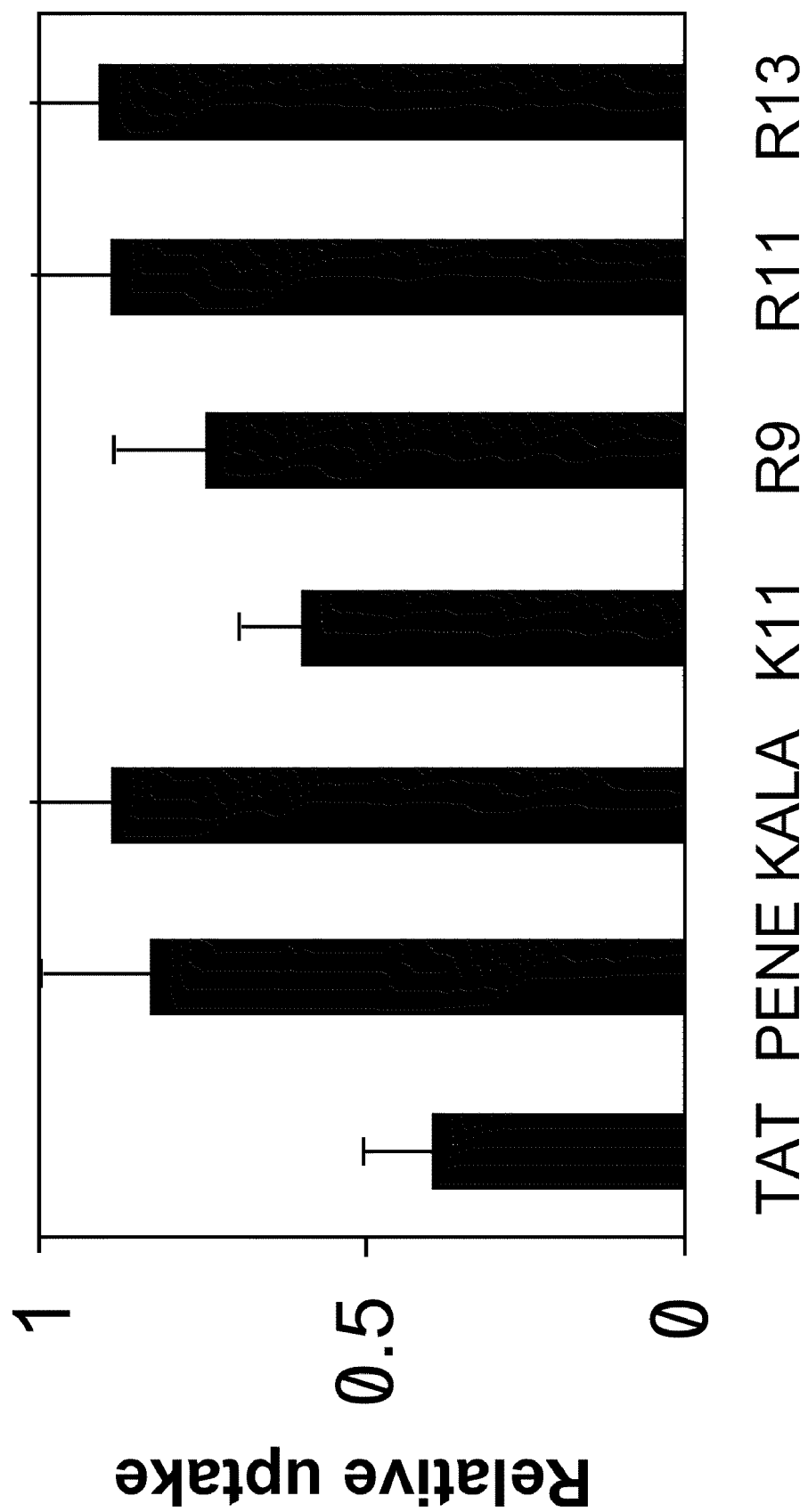
Figure 10C:
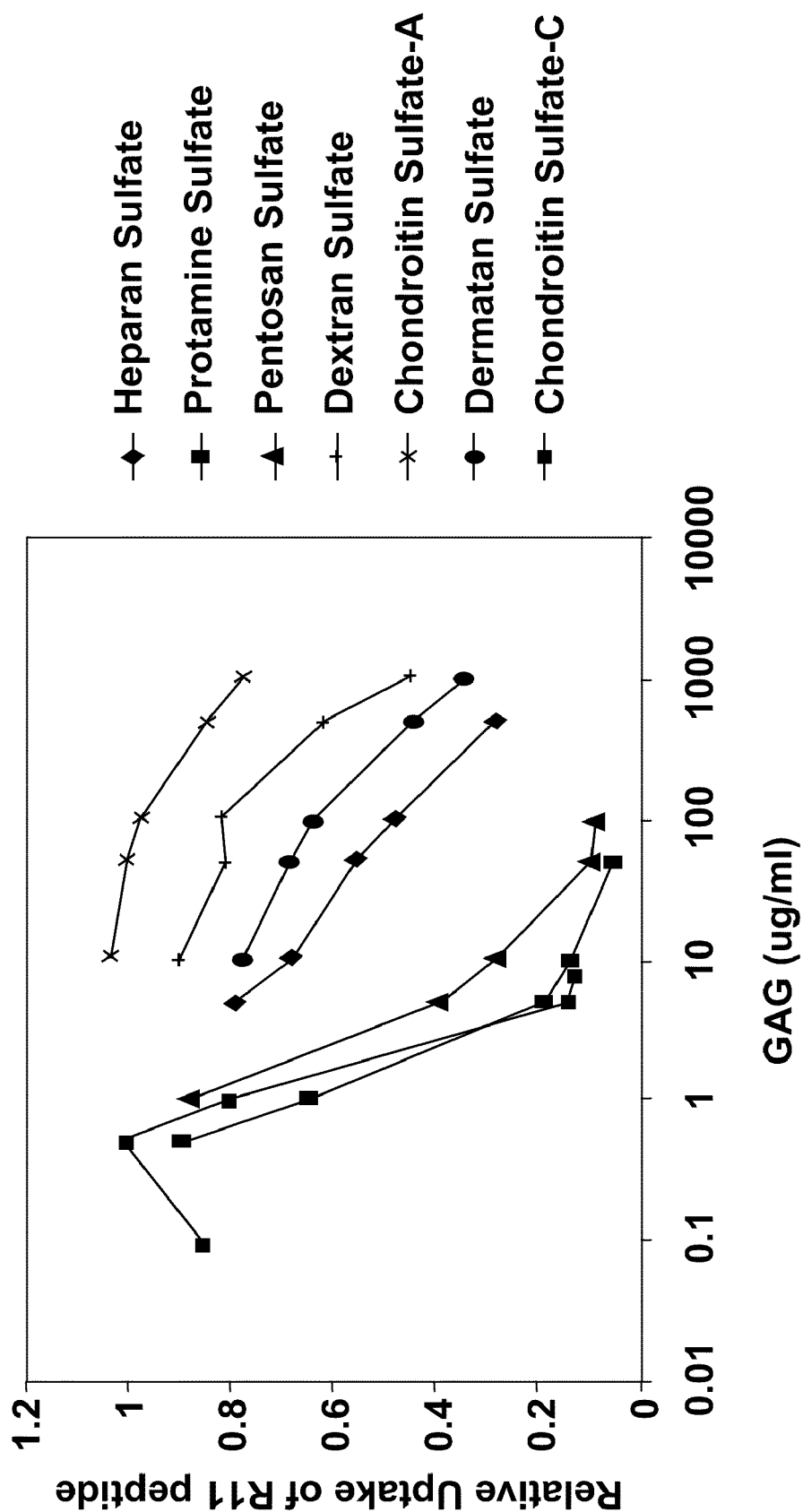

The inventors examined the effect of inhibitors for macropinocytosis-EIPA (FIG. 10A; 10, 11) that can effectively diminish R11 uptake and it can affect other CPPs in a less extend. Interestingly, they found that Rac inhibitor-Toxin B (12) does not alter R11 uptake, suggesting that CPP uptake may be mediated Rac-independent macropinocytosis. Furthermore, they examined a variety of glycosaminoglycans (GAGs) commonly detected in bladder wall (De Klerk, 1985) for their abilities to block the R11 uptake. As shown in FIGS. 10C-D, it appears that pentosan sulfate, protamine sulfate and dextran sulfate can effectively compete the uptake of R11 in several bladder cancer cell lines, indicating that these three GAGs have higher affinity to R11 than other GAGs tested in this experiment. These data further supported by a study that altered GAG expression associated with bladder carcinogenesis (Hurst and Zebrowski, 1994).

Example 12

Ex Vivo FTIC-R11 Imaging Using Xenograft Animal Model

Figure 11:
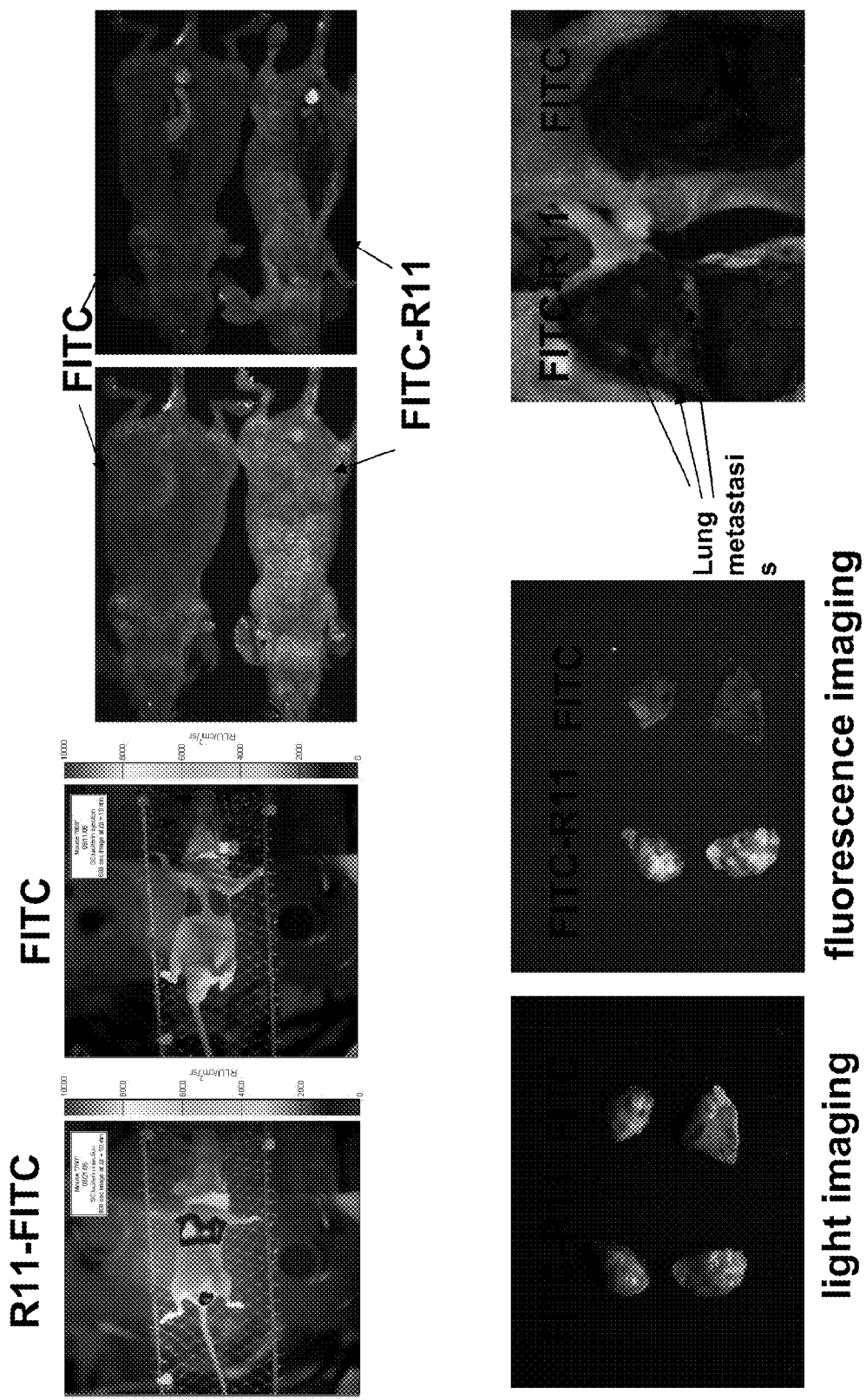
FIG. 11—Fluorescence imaging of R11 from lung metastasis nodule of T24 bladder cancer. Top right panel, athymic nude mice were chosen based on a similar size of lung metastasis of bladder cancer from BLI were IV injected with 5 nmole FITC-R11 (left) or FITC (right) per gram body weight. Twenty-four hours after injection, whole body imaging (top left panel) or ex vivo imaging (bottom middle and right panel) of lung was carried out with Maestro In-vivo Imaging System (CRI, Inc.). The image shown is one of the representative experiments.

To evaluate whether FITC-R11 peptide can be used as an imaging probe to detect distant metastasis of bladder cancer, the inventors injected FITC-R11 or FITC intravenously into mice carrying a similar size of lung metastatic nodules (Top right panel in FIG. 11). From the whole body imaging, a clear signal is detected in the bladder of mouse injected with FITC-R11 but no signal from lung is visible due to the high background of autofluorescence. By excising lung, a clear fluorescence signal is visualized in the ex vivo tumor lesion from FITC-R11-injected mice compared with control lung, which is further confirmed by determining specific uptake per gram tissue (data not sown). These data suggest R11 is a potential molecular probe for detecting distant metastasis of bladder cancer. However, due to a high fluorescence background and the hemoglobin absorbance, exploring other imaging modality is warranted.

Example 12

Figure 12:
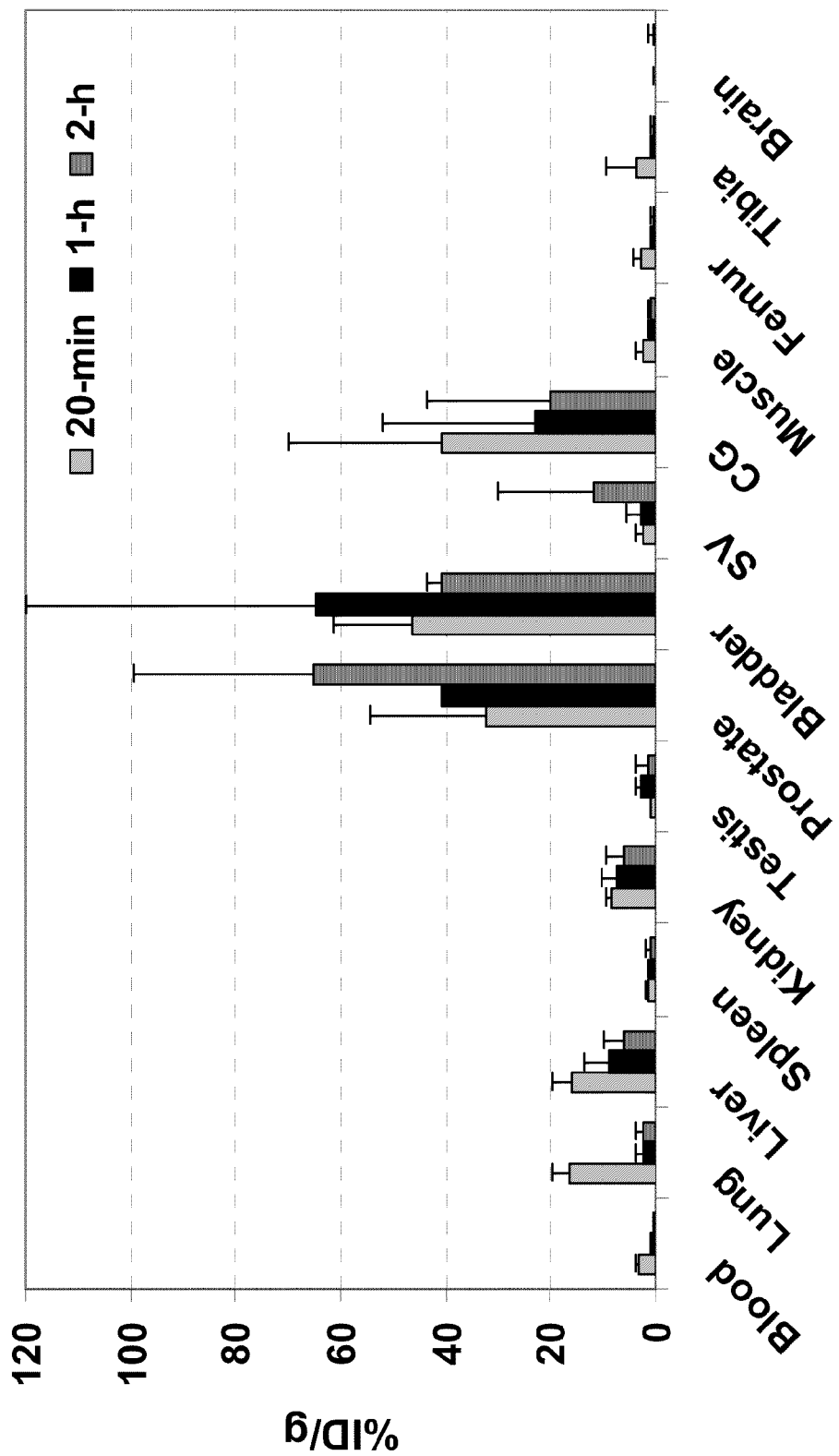
FIG. 12—Biodistribution data of $^{64}$Cu-DOTA-R11 in normal nude mice (n=4). Data are presented as % ID/g±s.d. SV: seminal vesicle; CG: coagulation gland.

Biodistribution and Pet Imaging of $^{64}$Cu-Labeled DOTA-R11 in Tumor-Bearing Mice In order to explore the application of R11 for the detection of bladder cancer metastasis via PET, the inventors conjugated this peptide with a bifunctional chelator, DOTA (1,4,7,10-tetraazacyclododecane-1,4,7,10-tetraacetic acid), so that R11 could be radiolabeled with $^{64}$Cu. The conjugation was carried out by automated peptide synthesizer and the conjugate, DOTA-G-RRRRRRRRRRR (DOTA-R11), was purified by reverse phase HPLC and characterized by mass spectrometry. DOTA-R11 was then radiolabeled with $^{64}$Cu (MDS Nordion, Canada) in 0.1 M NH$_4$OAc buffer (pH 7.5) at high radiochemical yields (>80%) after 2 hr incubation at RT. The radiolabeled peptide was purified via a C-18 cartridge (Millipore) to have >95% radiochemical purity as determined by radio-TLC and HPLC prior to the biodistribution and PET imaging studies. The highest specific activity of $^{64}$Cu-DOTA-R11 achieved was ~650 µCi/nmol. To determine the biodistribution of $^{64}$Cu-DOTA-R11 5-10 µCi was injected into normal healthy nude mice. The animals were sacrificed at specific time points (n=4 at each time point). Organs of interest were removed, weighed, and counted. Standards were prepared and counted along with the samples to calculate the percent injected dose per gram tissue (% ID/g). It is apparent that $^{64}$Cu-DOTA-R11 has a strong tendency to accumulate in prostate and bladder (FIG. 12), despite the large standard deviations likely representing animal individual difference. Further, this peptide exhibited remarkably low uptake by other organs (e.g., blood, lungs, liver, spleen, kidneys, and muscle). This confirms the observation using FITC tagged R11 in the same animal model and demonstrates that R11 could be a novel organ specific probe for the development of a new PET imaging agent. In addition, the pharmacokinetics of the $^{64}$Cu-labeled peptide was also evaluated by using a two-compartment model. Its half-life of $^{64}$Cu-DOTA-R11 in the blood (the primary compartment) was about 10.7 min ($t_{1/2N}$); and the elimination half-life from other organs (the secondary compartment) was 17.2 h ($t_{1/2N}$).

Figure 13:
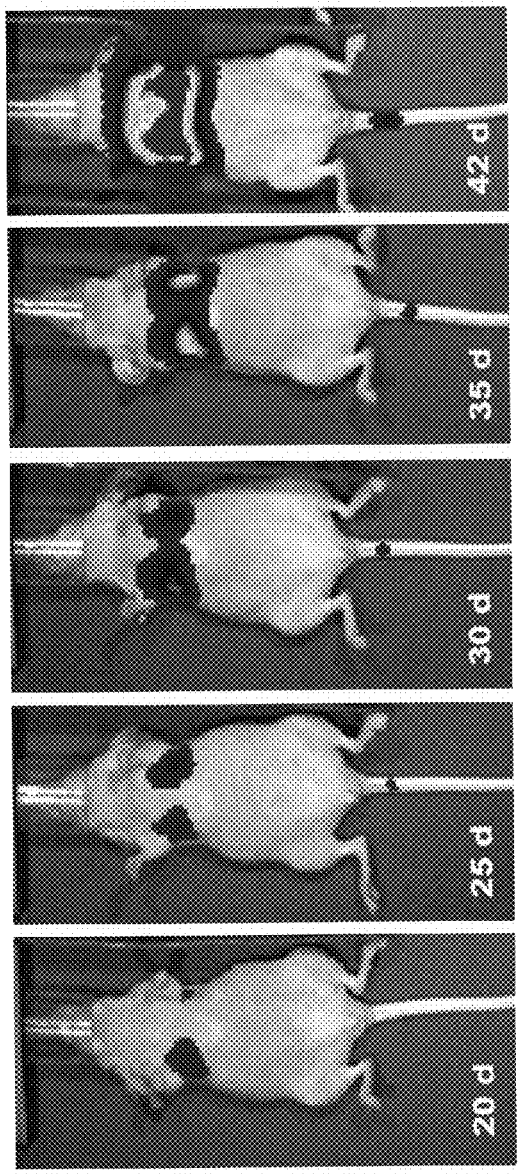
FIG. 13—BLI imaging of lung metastases.
Figure 13:
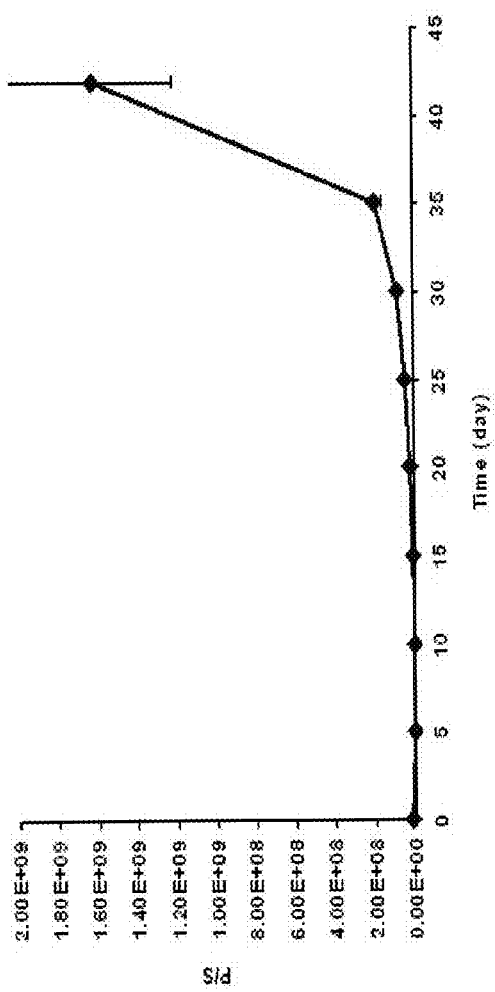

The tumor-bearing animal model was established by injecting into the left flank of each nude mouse subcutaneously with human T24 cell suspension (2×10$^6$ cells in 100-µL of medium). The tumors were allowed to grow for 42 days prior to PET imaging. The T24 lung metastases were monitored by BLI out to 42 days after the inoculation of tumor cells (FIG. 13). The microPET imaging studies were performed using the microPETR4 rodent scanner (Concorde Microsystems, Knoxville, Tenn.). The scanner provides a 10×8 cm field of view, and the scanner is currently capable of an axial and transaxial resolution of 2 mm, with an absolute sensitivity of 900 counts per second per µCi. Images were reconstructed using Fourier rebinning followed by two-dimensional filtered back projection. A T24 lung metastases bearing mouse and a control nude mouse were injected with ca. 200 µCi of $^{64}$Cu-DOTA-R11 in 100 µL saline via the tail vein. At 15 min, 60 min, and 4 hr post injection (p.i.), the mice were anesthetized and immobilized in a supine position on a support bed with attached anesthetic gas nose cones for data collection. The imaging collection time was 10 min. The lungs of T24 bearing animal were clearly imaged at 15-min p.i. with $^{64}$Cu-DOTA-R11 at 5-7% ID/g, while the uptake of control lungs was <4% ID/g. However, at 60 min and 4 hr p.i., no significant difference was observed. This is likely due to the rapid washout of $^{64}$Cu-DOTA-R11 from the lung metastases.

Figure 14:
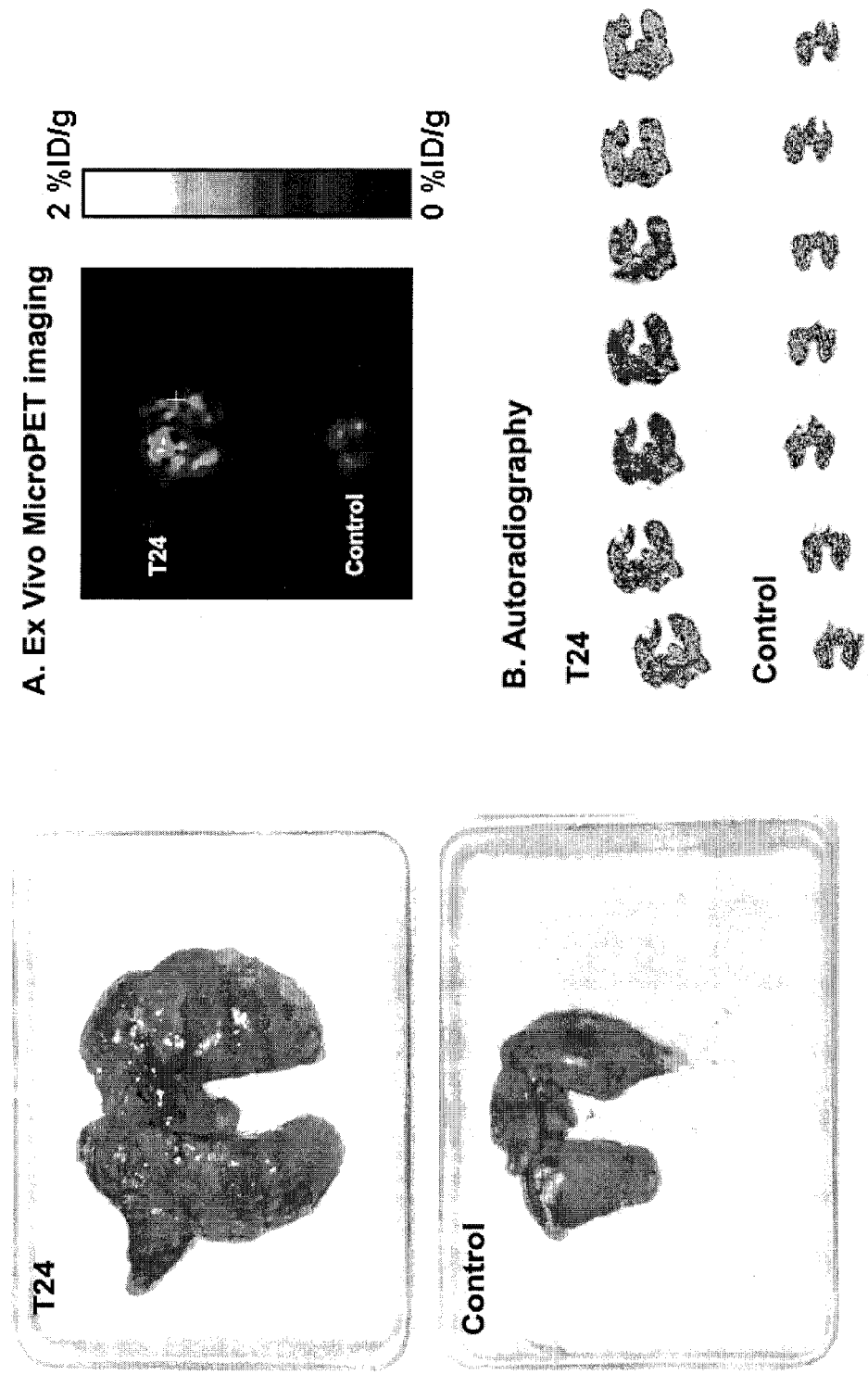
FIG. 14—Left: harvested lungs after 4 hr microPET imaging; Right upper: ex vivo microPET imaging of the harvested lungs; Right lower: autoradiography images of sliced lungs.

After the 4-hr microPET imaging, the animals were sacrificed. The lungs were removed from both mice. The lung metastases were present in the whole lungs of the T24 bearing mouse, inflating the lungs significantly. The harvested lungs were imaged by microPET again. The ex vivo microPET (FIG. 14A) and autoradiography images (FIG. 14B) clearly exhibited the elevated uptake of $^{64}$Cu-DOTA-R11 in the lungs with T24 metastases. Furthermore, a biodistribution study was conducted in two nude mice bearing T24 subcutaneous tumor in the left flank. The results revealed that the uptake ratio of tumor to muscle was greater than 8 and nearly identical in both animals.

**************

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 5,397,987
U.S. Pat. No. 5,399,363
U.S. Pat. No. 5,466,468
U.S. Pat. No. 5,543,158
U.S. Pat. No. 5,580,579
U.S. Pat. No. 5,629,001
U.S. Pat. No. 5,641,515
U.S. Pat. No. 5,641,515
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 6,610,657
U.S. Pat. No. 6,613,308
U.S. Pat. No. 6,7537,514
Ahlstrom et al., *Acta Radiol*, 37:180-185, 1996.
Alavi et al., *Radiol. Clin. North Am.*, 42:983-1001, 2004.
Alavi et al., *Semin. Nucl. Med.*, 34:56-69, 2004.
Albert et al., *Life Sci.*, 53:517-525, 1993.
Bender et al., *Anticancer Res.*, 17:1655-1660, 1997.
Benedetti et al., *BioDrugs*, 18:279-295, 2004.
Bloomberg et al., *Tetrahedron Lett.*, 34:4709-4712, 1993.
Borley et al., *Scand. J. Urol. Nephrol.*, 37:382-386, 2003.
Boswell et al., *J. Med. Chem.*, 47:1465-1474, 2004.
Brady and Dodson, *Nature*, 368:692-693, 1994.
Bruchovsky et al., *Cancer Res.*, 50:2275-2282, 1990.
Bure et al., *Rapid Commun. Mass Spectrom.*, 14:2158-64, 2000.
Carter et al., *Radiology*, 178:523-525, 1991.
Chang, *Curr. Opin. Investig. Drugs*, 5:611-615, 2004.
Chavez et al. *Org. Lett.*, 6:2889-2891, 2004.
Chen et al., *J. Biol. Chem.*, 273:17618-17625, 1998.
Chen et al., *J. Nucl. Med.*, 45:1390-1397, 2004.
Cole et al., *Am. J. Med. Sci.*, 319:118-122, 2000.
Coleman, *Cancer Treat. Rev.*, 27:165-176, 2001.
Daldrup-Link et al., *Curr. Pharm. Des.*, 12(21):2661-2672, 2006.
Datta et al., *Cancer Res.*, 61:1768-1775, 2001.
De Klerk, *J. Urol.*, 134:978-981, 1985.
Denoyer et al., *Curr. Cancer Drug Targets*, 6(3):181-196, 2006.
Derossi et al., *Trends in Cell Biol.*, 8:84-87, 1998.
Deshayes et al., *Cell Mol. Life. Sci.*, 62:1839-1849, 2005.
Dimitrakopoulou-Strauss and Strauss, *J. Nucl. Med.*, 44:556-558, 2003.
Downer et al., *Appl. Radiat. Isot.*, 48:907-916, 1997.
Drin et al., *AAPS PharmSci.*, 4(4):26, 2002.
El-Andaloussi et al., *Curr. Pharm. Des.*, 11:3597-3611, 2005.
Engelhardt et al., *J. Nucl. Med.*, 43:837-850, 2002.
Ferrari, *Nature Reviews*, 5:161-171, 2005.
Fischer et al., *J. Biol. Chem.*, 279:12625-12635, 2004.
Fogelman et al., *Semin. Nucl. Med.*, 35:135-142, 2005.
Fricke et al., *Eur. J. Nucl. Med. Mol. Imaging*, 30:607-611, 2003.
Futaki et al., *J. Biol. Chem.*, 276:5836-5840, 2001.
Futaki et al., *J. Mol. Recognit.*, 18:169-174, 2005.

Ghosh and Heston, *J. Cell Biochem.*, 91:528-539, 2004.
Gioeli et al., *Cancer Res.*, 59:279-284, 1999.
Goodman & Gilman's The Pharmacological Basis of Therapeutics
Green and Loewenstein, *Cell*, 55:1179-1188, 1988.
Gupta et al., *Biomaterials*, 26:3995-4021, 2005.
Hain and Maisey, *BJU Int.*, 92:159-64, 2003.
Hamilton and Mestler, *J. Gerontol.*, 24:395-411, 1969.
Hamma and Miller, *Bioconjug. Chem.*, 14:320-330, 2003.
Harbour et al., *Arch. Opthalmol.*, 120:1341-1346, 2002.
Haubner and Wester, *Curr. Pharm. Des.*, 10:1439-1455, 2004.
Haubner et al., *Bioconjug. Chem.*, 15:61-69, 2004.
Hautzel et al., *Urologe*, A41:569-576, 2002.
Herman et al., *Nucl. Med. Biol.*, 21:1005-1010, 1994.
Hersh et al., *Cancer Control*, 11:353-357, 2004.
Hofer et al., *Eur. Urol.*, 40:481-487, 2001.
Hoh et al., *J. Urol.*, 159:347-356, 1998.
Horowitz, In: *MRI Physics for Radiologists: A Visual Approach*, 1995.
Hricak et al., *Semin. Oncol.*, 30:616-634, 2003.
Huang et al., *Prostate*, 61:1-11, 2004.
Huggins and Hodges, *CA Cancer J. Clin.*, 22:232-240, 1972.
Huggins and Hodges, *Cancer Res.*, 1:293-297, 1941.
Huggins and Hodges, *J. Urol.*, 167:948-951, 2002.
Huggins and Hodges, *J. Urol.*, 168:9-12, 2002.
Hurst and Zebrowski, *J. Urol*, 152:1641-1645, 1994.
Hwang et al., *Crit. Rev. Ther. Drug Carrier Syst.*, 15(3):243-284, 1998.
Jager et al., *Radiology*, 215:445-451, 2000.
Jagoda et al., *Mol. Imaging. Biol.*, 4:369-379, 2002.
Jameson et al., *Nature*, 368:744-746, 1994.
Jana and Blaufox, *Semin. Nucl. Med.*, 36:51-72, 2006.
Johnson et al., In: *Biotechnology And Pharmacy*, Pezzuto et al. (Eds.), Chapman and Hall, NY, 1993.
Karam et al., *J. Cell Biochem.*, 90:473-483, 2003.
Kilbourn et al., *J. Nucl. Med.*, 28:462-470, 1987.
King and Feener, *Adv. Drug Deliv. Rev.*, 29:197-213, 1998.
Kotzerke et al., *Nuklearmedizin*, 42:25-30, 2003.
Kumar et al., *Radiol. Clin. North Am.*, 42:1141-1153, 2004.
Kwee et al., *J. Urol.*, 173:252-5, 2005.
Kyte and Doolittle, *J. Mol. Biol.*, 157(1):105-132, 1982.
Lamb and Faulds, *Drugs Aging*, 12:293-304, 1998.
Lang and Eckelman, *Appl. Radiat. Isot.*, 45:1155-1163, 1994.
Lang and Eckelman, *Appl. Radiat. Isot.*, 48:169-173, 1997.
Lange, *Urology*, 57:402-406, 2001.
Langsteger et al., *Semin. Nucl. Med.*, 36:73-92, 2006.
Lee et al., *Cancer Metastasis, Rev.*, 12:21-28, 1993.
Lin et al., *Prostate*, 47:212-221, 2001.
Lipsett, *Cancer*, 43:1967-1981, 1979.
Liu et al., *Cancer Res.*, 57:3629-3634, 1997.
Liu et al., *Prostate*, 60:98-108, 2004.
Lucia et al., *Prostate*, 36:49-55, 1998.
Maecke et al., *J. Nucl. Med.*, 46:172 S-178S, 2005.
Mai et al., *J. Biol. Chem.*, 277:30208-30218, 2002.
Mathews and Oz, *Curr. Opin. Urol.*, 12:381-385, 2002.
Mathiowitz et al., *Nature*, 386(6623):410-414, 1997.
Matthies et al., *Eur. J. Nucl. Med. Mol. Imaging*, 31:797, 2004.
Mayer, *J. Cell Sci.*, 114:1253-1263, 2001.
Meyer et al., *Eur. J. Nucl. Med. Mol. Imaging*, 31:1097-1104, 2004.
Miyamoto et al., *Prostate*, 61:332-353, 2004.
Murphy et al., *J. Urol.*, 160:2396-2401, 1998.
Noble, *Cancer Res.*, 37:1929-1933, 1977.
Noguchi et al., *Nat. Med.*, 10:305-309, 2004.
Oyama et al., *J. Nucl. Med.*, 43:181-186, 2002.
Oyama et al., *J. Nucl. Med.*, 44:549-555, 2003.
Oyama et al., *J. Nucl. Med.*, 45:519-525, 2004.
Oyama et al., *Nucl. Med. Biol.*, 29:783-790, 2002.
Oyen et al., *Expert Rev. Anticancer. Ther.*, 4:561-567, 2004.
Physicians Desk Reference
Poethko et al., *J. Nucl. Med.*, 45:892-902, 2004.
Pollard and Luckert, *Prostate*, 5:661-668, 1984.
Pollard and Luckert, *Prostate*, 6:389-393, 1985.
Pollard, *Prostate*, 1:203-213, 1980.
Pooga et al., *FASEB J.*, 12:67-77, 1998.
Price et al., *J. Urol.*, 162:1537-42, 1999.
Quinn et al., *Radiology*, 190:323-327, 1994.
Remington's: The Science and Practice of Pharmacy, 21th Ed. Lippincott Williams & Wilkins, 2005
Remington's Pharmaceutical Sciences, 15th Edition, pages 1035-1038 and 1570-1580, 1980.
Remington's Pharmaceutical Sciences, 18th Ed. Mack Printing Company, 1289-1329, 1990.
Renaudet and Dumy, *Org. Lett.*, 5:243-246, 2003.
Riccabona and Decristoforo, *Cancer Biother. Radiopharm.*, 18:675-687, 2003.
Rogers et al., *Bioconjug. Chem.*, 14:756-763, 2003.
Saar et al., *Anal. Biochem.*, 345:55-65, 2005.
Sanz et al., *World J. Urol.*, 22:351-352, 2004.
Scheffel and Pomper, *J. Nucl. Med.*, 45:1277-1278, 2004.
Schoder and Larson, *Semin. Nucl. Med.*, 34:274-292, 2004.
Schottelius et al., *Clin. Cancer Res.*, 10:3593-3606, 2004.
Schwarze et al., *Science*, 285:1569-1572, 1999.
Selivanova et al., *Nat. Med.*, 3:632-638, 1997.
Sewald and Jakubke, In: *Peptides: Chemistry and Biology*, Wiley-VCH, D-69469, Weinheim, Germany, 2002.
Shvarts et al., *Cancer Control*, 9:335-342, 2002.
Smith-Jones et al., *J. Nucl. Med.*, 44:610-617, 2003.
Snyder and Kilbourn, In: *Handbook of Radiopharmaceuticals*, Welch and Redvanly (Eds.), John Wiley & Sons Ltd., 195-227, Chochester, UK, 2003.
Sumers, *Radiology*, 187:875, 1993.
Sun and Anderson, *Methods Enzymol.*, 386:237-261, 2004.
Sun et al. *J. Med. Chem.*, 45:469-477, 2002.
Sun et al., *Bioconjug. Chem.*, 17:109-113, 2006.
Sun et al., *Eur. J. Nucl. Med. Mol. Imaging*, 32:15-22, 2005.
Sun et al., *J. Biol. Inorg. Chem.*, 8:217-225, 2003.
Sun et al., *Nucl. Med. Biol.*, 31:1051-1059, 2004.
Takenage et al., *J. Control Release*, 52(1-2):81-87, 1998.
The American Cancer Society, Cancer Facts and Figures, 2006.
The Merck Index, Eleventh Edition
Thumshirn et al., *Chem. Eur. J.*, 9:2717-2725, 2003.
Torchilin, *Adv. Drug Deliv. Rev.*, 57:95-109, 2005.
Toth et al., *J. Urol.*, 173:66-69, 2005.
Turner et al., *Nucleic Acids Res.*, 33:6837-6849, 2005.
Vaidyanathan and Zalutsky, *Bioconjug. Chem.*, 5:352-356, 1994.
Vaidyanathan and Zalutsky, *Int. J. Rad. Appl. Instrum.*, 19:275-281, 1992.
Vaidyanathan and Zalutsky, *Nucl. Med. Biol.*, 22:759-764, 1995.
Vaidyanathan and Zalutsky, *Nucl. Med. Biol.*, 24:171-178, 1997.
Vaidyanathan et al., *Clin. Cancer Res.*, 9:1868-1876, 2003.
Varagnolo et al., *Nucl. Med. Biol.*, 27:103-112, 2000.
Vidal et al., *Crit. Rev. Oncol. Hematol.*, 40:175-186, 2001.
Vives et al., *J. Biol. Chem.*, 272:16010-16017, 1997.
Wadia and Dowdy, *Adv. Drug Deliv. Rev.*, 57:579-596, 2005.
Wagenseil, *Zeitschriftfur morphologie und anthropologie*, 32:416-468, 1933.
Webbe et al., *Prostate*, 29:386-394, 1996.

Webber et al., *Prostate*, 30:136-142, 1997a.
Webber et al., *Prostate*, 30:58-64, 1997b.
Wender et al., *Proc. Natl. Acad. Sci. USA*, 97:13003-13008, 2000.
Wester et al., *Cancer Biother. Radiopharm.*, 19:231-244, 2004.
Wester et al., *Nucl. Med. Biol.*, 23:365-372, 1996.
Wester et al., *Nucl. Med. Biol.*, 24:275-286, 1997.
Xie et al., *Hepatobiliary Pancreat Dis. Int.*, 4:90-93, 2005.
Yeh et al., *Proc. Natl. Acad. Sci. USA*, 95:5527-5532, 1998.
Zatsepin et al., *Bioconjug. Chem.*, 13:822-830, 2002.
Zheng et al., *Bioorg. Med. Chem.*, 12:2887-2893, 2004.
Zhou and Hsieh, *J. Biol. Chem.*, 276:27793-27798, 2001.
Zhou et al., *Cancer & Met. Rev.*, 20:351-362, 2001.
Zhou et al., *Cancer Res.*, 65:9906-9913, 2005.
Zhou et al., *J. Biol. Chem.*, 278: 6936-6941, 2003.
Ziegler et al., *Biochemistry*, 44:138-148, 2005.

What is claimed is:

1. A pharmaceutical composition comprising R11 (SEQ ID NO: 6) conjugated to a Disabled Homolog 2 (DOC/DAB2) peptide.

2. The composition of claim 1, wherein the DOC/DAB2 peptide comprises the sequence of SEQ ID NO:5.

3. The composition of claim 2, wherein the DOC/DAB2 peptide consists essentially of the sequence of SEQ ID NO:5.

* * * * *

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Gly Arg Lys Lys Arg Arg Gln Arg Arg Arg
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide

<400> SEQUENCE: 2

Gly Arg Gln Ile Lys Ile Trp Phe Gln Asn Arg Arg Met Lys Trp Lys
1               5                   10                  15

Lys

<210> SEQ ID NO 3
<211> LENGTH: 19
<212> TYPE: PRT
<213> ORGANISM: Artificial Sequence
<220> FEATURE:
<223> OTHER INFORMATION: Synthetic peptide

<400> SEQUENCE: 3

Gly Lys Leu Ala Leu Lys Leu Ala Leu Lys Ala Leu Lys Ala Ala Leu
1               5                   10                  15

Lys Leu Ala

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Phe Gln Leu Arg Gln Ala Ala Leu Val Ala Ser Arg Lys Gly Glu
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 5

Phe Gln Leu Arg Gln Pro Pro Leu Val Pro Ser Arg Lys Gly Glu
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Arg Arg Arg Arg Arg Arg Arg Arg Arg Arg Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Gly Arg Lys Lys Arg Arg Gln Arg Arg Arg
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Gly Arg Gln Ile Lys Ile Trp Phe Gln Asn Arg Arg Met Lys Trp Lys
1               5                   10                  15

Lys

<210> SEQ ID NO 9
<211> LENGTH: 19
<212> TYPE: PRT
<213> ORGANISM: Artificial Sequence
<220> FEATURE:
<223> OTHER INFORMATION: Synthetic peptide

<400> SEQUENCE: 9

Gly Lys Leu Ala Leu Lys Leu Ala Leu Lys Ala Leu Lys Ala Ala Leu
1               5                   10                  15

Lys Leu Ala

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide

<400> SEQUENCE: 10

Arg Arg Arg Arg Arg Arg Arg Arg Arg Arg Arg Ala Leu Leu
1               5                   10

<210> SEQ ID NO 11
<211> LENGTH: 29
<212> TYPE: PRT
<213> ORGANISM: Artificial Sequence
<220> FEATURE:
```

-continued

```
<223> OTHER INFORMATION: Synthetic peptide

<400> SEQUENCE: 11

Gly Arg Arg Arg Arg Arg Arg Arg Arg Arg Arg Gly Gly Phe Gln
1               5                   10                  15

Leu Arg Gln Ala Ala Leu Val Ala Ser Arg Lys Gly Glu
            20                  25

<210> SEQ ID NO 12
<211> LENGTH: 28
<212> TYPE: PRT
<213> ORGANISM: Artificial Sequence
<220> FEATURE:
<223> OTHER INFORMATION: Synthetic peptide

<400> SEQUENCE: 12

Gly Arg Arg Arg Arg Arg Arg Arg Arg Arg Arg Gly Gly Phe Gln
1               5                   10                  15

Leu Arg Gln Pro Pro Leu Pro Ser Arg Lys Gly Glu
            20                  25
```